(12) United States Patent
Millan et al.

(10) Patent No.: US 10,695,384 B2
(45) Date of Patent: Jun. 30, 2020

(54) FEED ADDITIVE COMPOSITION

(71) Applicant: DUPONT NUTRITION BIOSCIENCES APS, Copenhagen (DK)

(72) Inventors: Luis Fernando Romero Millan, Wilshire (GB); Gregory Ross Siragusa, Waukesha, WI (US); Mari Ellen Davis, Waukesha, WI (US); Alexandra Helena Smith, Greendale, WI (US)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 0 days.

(21) Appl. No.: 16/181,427

(22) Filed: Nov. 6, 2018

(65) Prior Publication Data
US 2019/0076488 A1 Mar. 14, 2019

Related U.S. Application Data

(63) Continuation of application No. 13/985,863, filed as application No. PCT/GB2012/050124 on Jan. 19, 2012, now abandoned.

(30) Foreign Application Priority Data

Feb. 18, 2011 (GB) .................................. 1102857.8

(51) Int. Cl.
| | |
|---|---|
| *A61K 35/741* | (2015.01) |
| *C12N 1/20* | (2006.01) |
| *A23K 20/189* | (2016.01) |
| *C12R 1/125* | (2006.01) |
| *A23K 40/10* | (2016.01) |
| *A23K 40/30* | (2016.01) |
| *A23K 10/18* | (2016.01) |
| *A23K 50/75* | (2016.01) |
| *A61K 35/742* | (2015.01) |
| *A61K 38/46* | (2006.01) |
| *A61K 38/47* | (2006.01) |
| *A61K 38/48* | (2006.01) |

(52) U.S. Cl.
CPC ............ *A61K 35/741* (2013.01); *A23K 10/18* (2016.05); *A23K 20/189* (2016.05); *A23K 40/10* (2016.05); *A23K 40/30* (2016.05); *A23K 50/75* (2016.05); *A61K 35/742* (2013.01); *A61K 38/465* (2013.01); *A61K 38/47* (2013.01); *A61K 38/48* (2013.01); *C12N 1/20* (2013.01); *C12R 1/125* (2013.01); *C12Y 301/03* (2013.01); *C12Y 302/01* (2013.01); *C12Y 304/00* (2013.01)

(58) Field of Classification Search
CPC .. A61K 35/741; A61K 35/742; A61K 38/465; A61K 38/47; A61K 38/48; C12N 1/20; C12N 1/125
See application file for complete search history.

(56) References Cited

U.S. PATENT DOCUMENTS

| | | | |
|---|---|---|---|
| 4,683,202 | A | 7/1987 | Mullis et al. |
| 6,221,406 | B1 | 4/2001 | Meschonat et al. |
| 6,287,841 | B1 | 9/2001 | Mulleners et al. |
| 6,500,426 | B1 | 12/2002 | Barendse et al. |
| 6,562,340 | B1 | 4/2003 | Bedford et al. |
| 6,805,886 | B2 | 10/2004 | Slaugh |
| 2005/0255092 | A1 | 11/2005 | Rehberger et al. |
| 2007/0202088 | A1 | 8/2007 | Baltzley et al. |
| 2008/0263688 | A1 | 10/2008 | Lassen et al. |
| 2009/0280090 | A1 | 11/2009 | Rehberger et al. |

FOREIGN PATENT DOCUMENTS

| | | | |
|---|---|---|---|
| CN | 101181016 | 5/2008 | |
| EP | 120 693 | 10/1984 | |
| GB | 1011513 | 12/1965 | |
| WO | WO 1989/06270 | 7/1989 | |
| WO | WO 1989/06279 | 7/1989 | |
| WO | WO 1991/04669 | 4/1991 | |
| WO | WO-9206209 A1 * | 4/1992 | ......... C11D 3/38645 |
| WO | WO 1992/012645 | 8/1992 | |
| WO | WO 1992/19729 | 11/1992 | |
| WO | WO 1994/25583 | 11/1994 | |
| WO | WO 1997/016076 | 5/1997 | |

(Continued)

OTHER PUBLICATIONS

IUBMB Enzyme Nomenclature, EC.3.2.1.8 (Year: 2019).*
Altschul et al, "Basic local alignment search tool," J. Mol. Biol. 403-410, (1990).
Awad et al., "Effects of dietary inclusion . . . broiler chickens," Poult Sci 88 (1) 49-56, (2009).
Bailey et al., "Interlaboratory testing of methods for assay of xylanase activity," Journal of Biotechnology, vol. 23, (3), May 1992, 257-270).
Beucage S.L. et al., "Dexoynucleoside phosphoramidites—a new class of key intermediates for dexopolynucleotide synthesis," Tetrahedron Letters 22, p. 1859-1869, (1981).

(Continued)

*Primary Examiner* — Ruth A Davis

(57) ABSTRACT

A feed additive composition comprising a direct fed microbial in combination with a protease, a xylanase, an amylase and a phytase, and a method for improving the performance of a subject or for improving digestibility of a raw material in a feed (e.g. nutrient digestibility, such as amino acid digestibility), or for improving nitrogen retention, or for avoiding the negative effects of necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject, which method comprising administering to a subject a direct fed microbial in combination with a protease, a xylanase, an amylase and a phytase.

20 Claims, 18 Drawing Sheets

Specification includes a Sequence Listing.

(56) References Cited

FOREIGN PATENT DOCUMENTS

| | | |
|---|---|---|
| WO | WO 1998/20115 | 5/1998 |
| WO | WO 2003/062409 | 7/2003 |
| WO | WO 2004/085638 | 10/2004 |
| WO | WO 2005/123034 | 12/2005 |
| WO | WO 2006/037327 | 4/2006 |
| WO | WO 2006/037328 | 4/2006 |
| WO | WO 2006/038062 | 4/2006 |
| WO | WO 2006/038128 | 4/2006 |
| WO | WO 2006/043178 | 4/2006 |
| WO | WO 2007/044968 | 4/2007 |
| WO | WO 2007/112739 | 10/2007 |
| WO | WO 2008/016214 | 2/2008 |
| WO | WO 2008/092901 | 8/2008 |
| WO | WO 2008/097619 | 8/2008 |
| WO | WO 2009/129489 | 10/2009 |
| WO | PCT/IB2010/051804 | 10/2010 |
| WO | WO 2011/117396 | 9/2011 |
| WO | PCT/IB2011/053018 | 1/2012 |

OTHER PUBLICATIONS

Caruthers MH et al., "New chemical methods for synthesizing polynucleotides," Nuc Acids Res Symp Ser 215-23, (1980).
Chomczynski et al., "Single-step method of RNA . . . extraction," Anal. Biochem. 162:156-9, (1987).
Dowd et al., Evaluation of the bacterial diversity . . . pyrosequencing (bTEFAP), BMC Microbiology, 2008; 8, 125.
Druyan et al., "Growth rate of ascites-resistant . . . lines," Poult. Sci. 87: 2418-29, (2008).
Tatusova et al., "BLAST 2 sequences, a new tool . . . sequences," FEMS Microbiol Lett 174(2): 247-50, (1999).
Tatusova et al., "Erratum to "BLAST 2 sequences, a new tool . . . sequences ,"" FEMS Microbiol Lett 177(1): 187-8, (1999).
Garosi et al., "Defining best practice for microarray analyses in nutrigenomic studies," Br. J. Nutr. 93: 425-32, (2005).
Higgins DG et al.,, "CLUSTAL: a package for performing multiple sequence alignment on a microcomputer," Gene 73(1), 237-244, (1988).
Hill et al., "Comparison of metabolizable . . . chicks," J. Nutr. 64: 587-603, (1958).
Hofacre et al., "Using competitive exclusion . . . Necrotic enteritis," J. Appl. Poult. Res. 12:60-64, (2003).
Horn T et al., "Synthesis of oligonucleotides . . . Polypeptide (GIP)," Nuc Acids Res Symp Ser 225-232, (1980).
Matthes et al., "Simultaneous rapid chemical shnthesis of over one hundred oligonucleotides on a microscale," EMBO J. 3, p. 801-805, (1984).
Ravindran, et al., "Response of broiler chickens to microbial phytase supplementation as influenced by dietary phytic acid and non-phytate phosphorous levels II. Effects on apparent metabolisable energy, nutrient digestability and nutrient retention", British Poultry Science, vol. 41, Issue 2, pp. 193-200, (2000).
Rudrappa et al., "Energy metabolism in developing chicken . . . transition,", J. Nutr. 137: 427-432, (2007).
Saiki R K et al., "Primer-directed enzymatic amplification of DNA with a thermostable DNA polymerase," Science 239, pp. 487-491, (1988).
Wang, et al., "Beneficial effects of Versazyme, a keratinase feed additive, on body weight, feed conversion, and breast yield of broiler chickens", Journal of Applied Poultry Research, vol. 15, No. 4, p. 544, (2006).
Chen et al., Purification and characterization of a xylanase from Trichoderma longibrachiatum for xylooligosaccharide production, Enzyme and Microbiology Technology, 1997, pp. 91-96, vol. 21.
International Search Report and Written Opinion—PCT/GB2012/050124 —dated Aug. 16, 2012.

* cited by examiner

```
1    anlngtlmqy fewympndgq hwkrlqndsa ylaehgitav wippaykgts qadvgygayd  60
61   lydlgefhqk gtvrtkygtk gelqsaiksl hsrdinvygd vvinhkggad atedvtavev 120
121  dpadrnrvis gehlikawth fhfpgrgsty sdfkwhwyhf dgtdwdesrk lnriykfqgk 180
181  awdwevsnen gnydylmyad idydhpdvaa eikrwgtwya nelqldgfrl davkhikfsf 240
241  lrdwvnhvre ktgkemftva eywqndlgal enylnktnfn hsvfdvplhy qfhaastqgg 300
301  gydmrkllng tvvskhplks vtfvdnhdtq pgqslestvq twfkplayaf iltresgypq 360
361  vfygdmygtk gdsqreipal khkiepilka rkqyaygaqh dyfdhhdivg wtregdssva 420
421  nsglaalitd gpggakrmyv grqnagetwh ditgnrsepv vinsegwgef hvnggsvsiy 480
481  vqr
```

FIG. 11

```
gcaaatcttaatgggacgctgatgcagtattttgaatggtacatgcccaatgacggccaacattggaa
gcgtttgcaaaacgactcggcatatttggctgaacacggtattactgccgtctggattcccccggcat
ataagggaacgagccaagcggatgtgggctacggtgcttacgacctttatgatttaggggagtttcat
caaaagggacggttcggacaaagtacggcacaaaggagagctgcaatctgcgatcaaaagtcttca
ttcccgcgacattaacgtttacggggatgtggtcatcaaccacaaaggcggcgctgatgcgaccgaag
atgtaaccgcggttgaagtcgatcccgctgaccgcaaccgcgtaatttcaggagaacacctaattaaa
gcctggacacattttcattttccggggcgcggcagcacatacagcgatttttaaatggcattggtacca
ttttgacggaaccgattgggacgagtcccgaaagctgaaccgcatctataagtttcaaggaaaggctt
gggattgggaagtttccaatgaaaacggcaactatgattatttgatgtatgccgacatcgattatgac
catcctgatgtcgcagcagaaattaagagatggggcacttggtatgccaatgaactgcaattggacgg
tttccgtcttgatgctgtcaaacacattaaattttctttttttgcgggattgggttaatcatgtcaggg
aaaaaacggggaaggaaatgtttacggtagctgaatattggcagaatgacttgggcgcgctggaaaac
tatttgaacaaaacaaattttaatcattcagtgtttgacgtgccgcttcattatcagttccatgctgc
atcgacacagggaggcggctatgatatgaggaaattgctgaacggtacggtcgtttccaagcatccgt
tgaaatcggttacatttgtcgataaccatgatacacagccggggcaatcgcttgagtcgactgtccaa
acatggtttaagccgcttgcttacgcttttattctcacaagggaatctggatacctcaggttttcta
cggggatatgtacgggacgaaaggagactcccagcgcgaaattcctgccttgaaacacaaaattgaac
cgatcttaaaagcgagaaacagtatgcgtacggagcacagcatgattatttcgaccaccatgacatt
gtcggctggacaagggaaggcgacagctcggttgcaaattcaggtttggcggcattaataacagacgg
acccggtggggcaaagcgaatgtatgtcggccggcaaaacgccggtgagacatggcatgacattaccg
gaaaccgttcggagccggttgtcatcaattcggaaggctggggagagtttcacgtaaacggcgggtcg
gtttcaatttatgttcaaagatga
```

FIG. 12

```
1    MKLRYALPLL LQLSLPVLSA DTAAWRSRTI YFALTDRIAR GSGDTGGSAC GNLGDYCGGT  60
61   FQGLESKLDY IKGMGFDAIW ITPVVTSDDG GYHGYWAEDI DSINSHYGSA DDLKSLVNAA 120
121  HSKGFYMMVD VVANHMGYAN ISDDSPSPLN QASSYHPECD IDYNNQTSVE NCWISGLPDL 180
181  NTQSSTIRSL YQDWVSNLVS TYGFDGVRID TVKHVEQDYW PGFVNATGVY CIGEVFDGDP 240
241  NYLLPYASLM PGLLNYAIYY PMTRFFLQQG SSQDMVNMHD QIGSMFPDPT ALGTFVDNHD 300
301  NPRFLSIKND TALLKNALTY TILSRGIPIV YYGTEQAFSG GNDPANREDL WRSGFNAQSD 360
361  MYDAISKLTY AKHAVGGLAD NDHKHLYVAD TAYAFSRAGG NMVALTTNSG SGSSAQHCFG 420
421  TQVPNGRWQN VFDEGNGPTY SADGNGQLCL NVSNGQPIVL LSS
```

FIG. 13

```
atgaagctccggtacgctctcccgctgctcttgcagctctctttgccggtcctctccgcagacaccgc
cgcctggaggtcccgcaccatctactttgccctgacagaccgcatcgctcgtggaagcggtgacacgg
ggggcagtgcgtgtgggaacctgggggactactgcggtggcacgttccagggcttggagagcaagttg
gactacatcaagggcatgggattcgatgccatctggatcacacctgttgtgacgagtgatgatggggg
ctaccatggctattgggcggaggacatcgactccatcaactctcattatggctctgcggacgatctca
agagtctcgtcaacgccgcgcatagcaagggcttctatatgatggtggacgtcgtggccaaccacatg
ggctacgccaatatctctgacgatagtccctctccactgaaccaggcctcgtcgtatcaccccgagtg
tgatatcgactacaacaaccaaaccagcgtcgagaactgctggatcagcggcctcccggatctcaaca
cgcagagctcaaccatccgcagcctctaccaggactgggtctccaacctcgtgtccacgtacggcttc
gacggcgtccgcatcgacaccgtcaagcacgtcgagcaagactactggcccggcttcgtcaacgccac
cggcgtctactgcatcggcgaggtctttgacggagacccaaactacctgctgccctacgccagcctca
tgccgggcctgctcaactacgccatctactaccccatgacgcgcttcttcctccagcagggctcctcg
caggacatggtcaacatgcacgaccagatcggcagcatgttccccgacccgaccgcgctcggcacctt
tgtcgacaaccacgacaacccgcgcttcctgagcatcaagaacgacacggccctgctcaagaacgcgc
tgacgtacaccatcctctcgcgcggcatccccatcgtctactacggcaccgagcaggccttctcgggc
ggcaacgacccggccaacagggaggacctctggcgcagcggcttcaacgcccagtccgacatgtacga
cgccatctccaagctcacctacgccaagcacgccgtcggcggcctcgccgacaacgaccacaagcacc
tgtacgtcgccgacacggcctacgccttcagccgcgccggcggcaacatggtggccctgaccaccaac
agcggcagcgggagctcggcccagcactgcttcggcacgcaggtgcccaacggccgctggcagaatgt
ctttgacgagggcaatgggccgacgtattccgccgacggcaacggccagctttgcttgaatgtgtcca
acggtcagcccattgtcttgctgtcttcgtga
```

FIG. 14

SEQUENCE LISTING

<160> NUMBER OF SEQ ID NOS: 6

<210> SEQ ID NO 1
<211> LENGTH: 483
<212> TYPE: PRT
<213> ORGANISM: Bacillus licheniformis

<400> SEQUENCE: 1

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 2
<211> LENGTH: 1452
<212> TYPE: DNA
<213> ORGANISM: Bacillus licheniformis

<400> SEQUENCE: 2

```
gcaaatctta atgggacgct gatgcagtat tttgaatggt acatgcccaa tgacggccaa      60
cattggaagc gtttgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttca ggagaacacc taattaaagc ctggacacat     420
tttcattttc cggggcgcgg cagcacatac agcgatttta atggcattg gtaccatttt     480
gacggaaccg attgggacga gtcccgaaag ctgaaccgca tctataagtt tcaaggaaag     540
gcttgggatt gggaagtttc caatgaaaac ggcaactatg attatttgat gtatgccgac     600
atcgattatg accatcctga tgtcgcagca gaaattaaga gatggggcac ttggtatgcc     660
aatgaactgc aattggacgg tttccgtctt gatgctgtca acacattaa attttctttt     720
ttgcgggatt gggttaatca tgtcagggaa aaaacgggga aggaaatgtt tacggtagct     780
gaatattggc agaatgactt gggcgcgctg gaaaactatt tgaacaaaac aaattttaat     840
cattcagtgt ttgacgtgcc gcttcattat cagttccatg ctgcatcgac acaggaggc     900
ggctatgata tgaggaaatt gctgaacggt acggtcgttt ccaagcatcc gttgaaatcg     960
gttacatttg tcgataacca tgatacacag ccggggcaat cgcttgagtc gactgtccaa    1020
acatggttta gccgcttgc ttacgctttt attctcacaa gggaatctgg atacctcag    1080
gttttctacg gggatatgta cgggacgaaa ggagactccc agcgcgaaat tcctgccttg    1140
aaacacaaaa ttgaaccgat cttaaaagcg agaaaacagt atgcgtacgg agcacagcat    1200
gattatttcg accaccatga cattgtcggc tggacaaggg aaggcgacag ctcggttgca    1260
aattcaggtt tggcggcatt aataacagac ggacccggtg gggcaaagcg aatgtatgtc    1320
ggccggcaaa acgccggtga gacatggcat gacattaccg gaaaccgttc ggagccggtt    1380
gtcatcaatt cggaaggctg gggagagttt cacgtaaacg gcgggtcggt ttcaatttat    1440
```

```
gttcaaagat ga                                                      1452
```

<210> SEQ ID NO 3
<211> LENGTH: 463
<212> TYPE: PRT
<213> ORGANISM: Trichoderma reesei

<400> SEQUENCE: 3

| Met | Lys | Leu | Arg | Tyr | Ala | Leu | Pro | Leu | Leu | Gln | Leu | Ser | Leu | Pro |
| 1 | | | | 5 | | | | | 10 | | | | | 15 |

| Val | Leu | Ser | Ala | Asp | Thr | Ala | Ala | Trp | Arg | Ser | Arg | Thr | Ile | Tyr | Phe |
| | | | 20 | | | | | 25 | | | | | 30 | | |

| Ala | Leu | Thr | Asp | Arg | Ile | Ala | Arg | Gly | Ser | Gly | Asp | Thr | Gly | Gly | Ser |
| | | | 35 | | | | | 40 | | | | | 45 | | |

| Ala | Cys | Gly | Asn | Leu | Gly | Asp | Tyr | Cys | Gly | Thr | Phe | Gln | Gly | Leu |
| | 50 | | | | | 55 | | | | | 60 | | | |

| Glu | Ser | Lys | Leu | Asp | Tyr | Ile | Lys | Gly | Met | Gly | Phe | Asp | Ala | Ile | Trp |
| 65 | | | | | 70 | | | | | 75 | | | | | 80 |

| Ile | Thr | Pro | Val | Val | Thr | Ser | Asp | Asp | Gly | Tyr | His | Gly | Tyr | Trp |
| | | | | 85 | | | | | 90 | | | | | 95 |

| Ala | Glu | Asp | Ile | Asp | Ser | Ile | Asn | Ser | His | Tyr | Gly | Ser | Ala | Asp | Asp |
| | | | 100 | | | | | 105 | | | | | 110 | | |

| Leu | Lys | Ser | Leu | Val | Asn | Ala | Ala | His | Ser | Lys | Gly | Phe | Tyr | Met | Met |
| | | | 115 | | | | | 120 | | | | | 125 | | |

| Val | Asp | Val | Val | Ala | Asn | His | Met | Gly | Tyr | Ala | Asn | Ile | Ser | Asp | Asp |
| | 130 | | | | | 135 | | | | | 140 | | | |

| Ser | Pro | Ser | Pro | Leu | Asn | Gln | Ala | Ser | Ser | Tyr | His | Pro | Glu | Cys | Asp |
| 145 | | | | | 150 | | | | | 155 | | | | | 160 |

| Ile | Asp | Tyr | Asn | Asn | Gln | Thr | Ser | Val | Glu | Asn | Cys | Trp | Ile | Ser | Gly |
| | | | | 165 | | | | | 170 | | | | | 175 |

| Leu | Pro | Asp | Leu | Asn | Thr | Gln | Ser | Ser | Thr | Ile | Arg | Ser | Leu | Tyr | Gln |
| | | | 180 | | | | | 185 | | | | | 190 | | |

| Asp | Trp | Val | Ser | Asn | Leu | Val | Ser | Thr | Tyr | Gly | Phe | Asp | Gly | Val | Arg |
| | | 195 | | | | | 200 | | | | | 205 | | | |

| Ile | Asp | Thr | Val | Lys | His | Val | Glu | Gln | Asp | Tyr | Trp | Pro | Gly | Phe | Val |
| | 210 | | | | | 215 | | | | | 220 | | | |

| Asn | Ala | Thr | Gly | Val | Tyr | Cys | Ile | Gly | Glu | Val | Phe | Asp | Gly | Asp | Pro |
| 225 | | | | | 230 | | | | | 235 | | | | | 240 |

| Asn | Tyr | Leu | Leu | Pro | Tyr | Ala | Ser | Leu | Met | Pro | Gly | Leu | Leu | Asn | Tyr |
| | | | | 245 | | | | | 250 | | | | | 255 |

| Ala | Ile | Tyr | Tyr | Pro | Met | Thr | Arg | Phe | Phe | Leu | Gln | Gly | Ser | Ser |
| | | | 260 | | | | | 265 | | | | | 270 | |

| Gln | Asp | Met | Val | Asn | Met | His | Asp | Gln | Ile | Gly | Ser | Met | Phe | Pro | Asp |
| | | | 275 | | | | | 280 | | | | | 285 | | |

| Pro | Thr | Ala | Leu | Gly | Thr | Phe | Val | Asp | Asn | His | Asp | Asn | Pro | Arg | Phe |
| | 290 | | | | | 295 | | | | | 300 | | | |

| Leu | Ser | Ile | Lys | Asn | Asp | Thr | Ala | Leu | Leu | Lys | Asn | Ala | Leu | Thr | Tyr |
| 305 | | | | | 310 | | | | | 315 | | | | | 320 |

| Thr | Ile | Leu | Ser | Arg | Gly | Ile | Pro | Ile | Val | Tyr | Tyr | Gly | Thr | Glu | Gln |
| | | | | 325 | | | | | 330 | | | | | 335 |

| Ala | Phe | Ser | Gly | Gly | Asn | Asp | Pro | Ala | Asn | Arg | Glu | Asp | Leu | Trp | Arg |
| | | | 340 | | | | | 345 | | | | | 350 | | |

| Ser | Gly | Phe | Asn | Ala | Gln | Ser | Asp | Met | Tyr | Asp | Ala | Ile | Ser | Lys | Leu |
| | | 355 | | | | | 360 | | | | | 365 | | | |

```
Thr Tyr Ala Lys His Ala Val Gly Gly Leu Ala Asp Asn Asp His Lys
    370             375                 380
His Leu Tyr Val Ala Asp Thr Ala Tyr Ala Phe Ser Arg Ala Gly Gly
385                 390                 395                 400
Asn Met Val Ala Leu Thr Thr Asn Ser Gly Ser Gly Ser Ser Ala Gln
                405                 410                 415
His Cys Phe Gly Thr Gln Val Pro Asn Gly Arg Trp Gln Asn Val Phe
                420                 425                 430
Asp Glu Gly Asn Gly Pro Thr Tyr Ser Ala Asp Gly Asn Gly Gln Leu
                435                 440                 445
Cys Leu Asn Val Ser Asn Gly Gln Pro Ile Val Leu Leu Ser Ser
    450                 455                 460
```

<210> SEQ ID NO 4
<211> LENGTH: 1392
<212> TYPE: DNA
<213> ORGANISM: Trichoderma reesei

<400> SEQUENCE: 4

```
atgaagctcc ggtacgctct cccgctgctc ttgcagctct ctttgccggt cctctccgca    60
gacaccgccg cctggaggtc ccgcaccatc tactttgccc tgacagaccg catcgctcgt   120
ggaagcggtg acacgggggg cagtgcgtgt gggaacctgg gggactactg cggtggcacg   180
ttccagggct tggagagcaa gttggactac atcaagggca tgggattcga tgccatctgg   240
atcacacctg ttgtgacgag tgatgatggg ggctaccatg gctattgggc ggaggacatc   300
gactccatca actctcatta tggctctgcg gacgatctca gagtctcgt caacgccgcg   360
catagcaagg gcttctatat gatggtggac gtcgtggcca accacatggg ctacgccaat   420
atctctgacg atagtccctc tccactgaac caggcctcgt cgtatcaccc cgagtgtgat   480
atcgactaca caaccaaac cagcgtcgag aactgctgga tcagcggcct cccggatctc   540
aacacgcaga gctcaaccat ccgcagcctc taccaggact gggtctccaa cctcgtgtcc   600
acgtacggct tcgacggcgt ccgcatcgac accgtcaagc acgtcgagca agactactgg   660
cccggcttcg tcaacgccac cggcgtctac tgcatcggcg aggtcttga cggagaccca   720
aactacctgc tgccctacgc cagcctcatg ccgggcctgc tcaactacgc catctactac   780
cccatgacgc gcttcttcct ccagcagggc tcctcgcagg acatggtcaa catgcacgac   840
cagatcggca gcatgttccc cgacccgacc gcgctcggca cctttgtcga caaccacgac   900
aacccgcgct tcctgagcat caagaacgac acggccctgc tcaagaacgc gctgacgtac   960
accatcctct cgcgcggcat ccccatcgtc tactacggca ccgagcaggc cttctcgggc  1020
ggcaacgacc cggccaacag ggaggacctc tggcgcagcg gcttcaacgc ccagtccgac  1080
atgtacgacg ccatctccaa gctcacctac gccaagcacg ccgtcggcgg cctcgccgac  1140
aacgaccaca gcacctgta cgtcgccgac acggcctacg ccttcagccg cgccggcggc  1200
aacatggtgg ccctgaccac caacagcggc agcgggagct cggcccagca ctgcttcggc  1260
acgcaggtgc ccaacggccg ctggcagaat gtctttgacg agggcaatgg ccgacgtat   1320
tccgccgacg gcaacggcca gctttgcttg aatgtgtcca acggtcagcc cattgtcttg  1380
ctgtcttcgt ga                                                      1392
```

<210> SEQ ID NO 5
<211> LENGTH: 19
<212> TYPE: DNA
<213> ORGANISM: Artificial Sequence

```
<220> FEATURE:
<223> OTHER INFORMATION: Primer 28F
<220> FEATURE:
<221> NAME/KEY: misc_feature
<222> LOCATION: (11)..(11)
<223> OTHER INFORMATION: n is a, c, g, or t

<400> SEQUENCE: 5
gagtttgatc ntggctcag                                                    19

<210> SEQ ID NO 6
<211> LENGTH: 18
<212> TYPE: DNA
<213> ORGANISM: Artificial Sequence
<220> FEATURE:
<223> OTHER INFORMATION: Primer 519R
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 6
gtnttacngc ggckgctg                                                     18
```

FEED ADDITIVE COMPOSITION

CROSS REFERENCE TO RELATED APPLICATIONS

This application is a continuation of U.S. patent application Ser. No. 13/985,863 filed Aug. 15, 2013, pending, which is a 371 of PCT/GB2012/050124, filed Jan. 19, 2012, expired, which claims the priority benefit of GB 1102857.8 file Feb. 18, 2011, expired, all of which are incorporated by reference in their entirety.

SEQUENCE LISTING

The sequence listing submitted via EFS, in compliance with 37 CFR § 1.52(e), is incorporated by reference. The sequence listing text file submitted via EFS contains the file named "NB31540USPCT_SequenceListing" created on Aug. 15, 2013 which is 13 KB in size.

FIELD OF INVENTION

The present invention relates to methods for improving feed compositions using a direct fed microbial in combination with a specific combination of enzymes, and to a feed additive composition comprising a direct fed microbial in combination with a specific combination of enzymes. The present invention further relates to uses and kits.

BACKGROUND OF THE INVENTION

Supplemental enzymes are used as additives to animal feed, particularly poultry and swine feeds, as a means to improve nutrient utilization and production performance characteristics. Enzyme blends are available to improve the nutritional value of diets containing soybean meal, animal protein meals, or high fibre food by-products.

The concept of direct fed microbials (DFM) involves the feeding of beneficial microbes to animals, such as dairy cattle when they are under periods of stress (disease, ration changes, environmental or production challenges). Probiotics is another term for this category of feed additives. Probiotics or DFM have been shown to improve animal performance in controlled studies. DFM including direct fed bacteria and or yeast-based products.

Although combinations of DFMs with some enzymes have been contemplated, the interaction between DFMs and enzyme has never been fully understood. The present invention relates to novel specific combinations which surprisingly significantly improve production performance characteristics of animals.

SUMMARY OF INVENTION

A seminal finding of the present invention is that a DFM in combination with a protease, xylanase, amylase and phytase has significant beneficial effects on the performance of an animal.

In particular, a seminal finding of the present invention is that a DFM in combination with a protease, xylanase, amylase and phytase has significant beneficial effects on the performance of an animal, including improving one or more of the following: feed conversion ratio (FCR), ability to digest a raw material (e.g. nutrient digestibility, such as amino acid digestibility), nitrogen retention, survival, carcass yield, growth rate, weight gain, feed efficiency animals resistance to necrotic enteritis, immune response of the subject, or the growth of beneficial bacteria in the gastrointestinal tract of a subject.

Another surprising effect of the present invention is that it can reduce nutrient excretion in manure (e.g. reduce nitrogen and phosphorus) content of a subject's manure.

In one aspect, the present invention provides a feed additive composition comprising (or consisting essentially of or consisting of) a direct fed microbial in combination with a protease, a xylanase, an amylase and a phytase.

In another aspect, the present invention provides a method for improving the performance of a subject or for improving digestibility of a raw material in a feed (e.g. nutrient digestibility, such as amino acid digestibility), or for improving nitrogen retention, or for avoiding the negative effects of necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject or for reducing populations of pathogenic bacteria in the gastrointestinal tract of a subject, or for reducing nutrient excretion in manure, which method comprising administering to a subject a direct fed microbial in combination with a protease, a xylanase, an amylase and a phytase.

A yet further aspect of the present invention is use of a direct fed microbial in combination with a protease, a xylanase, an amylase and a phytase for improving the performance of a subject or for improving digestibility of a raw material in a feed (e.g. nutrient digestibility, such as amino acid digestibility) or for improving nitrogen retention) or for avoiding the negative effects of necrotic enteritis or for improving feed conversion ratio (FCR) or for improving weight gain in a subject or for improving feed efficiency in a subject or for modulating (e.g. improving) the immune response of the subject or for promoting the growth of beneficial bacteria in the gastrointestinal tract of a subject or for reducing populations of pathogenic bacteria in the gastrointestinal tract of a subject, or for reducing nutrient excretion in manure.

In a further aspect of the present invention there is provided a kit comprising a direct fed microbial, a protease, a xylanase, an amylase, a phytase (and optionally at least one vitamin and/or optionally at least one mineral) and instructions for administration.

In another aspect the present invention provides a method of preparing a feed additive composition, comprising admixing a direct fed microbial with a protease, a xylanase, an amylase and a phytase and (optionally) packaging.

In a yet further aspect the present invention provides feed or feedstuff comprising a feed additive composition comprising (or consisting essentially of or consisting of) a direct fed microbial in combination with a protease, a xylanase, an amylase and a phytase.

A premix comprising a feed additive composition comprising (or consisting essentially of or consisting of) a direct fed microbial in combination with a protease, a xylanase, an amylase and a phytase, and at least one mineral and/or at least one vitamin.

In another aspect, the present invention provides a method of preparing a feedstuff comprising admixing a feed component with a feed additive composition comprising (or consisting essentially of or consisting of) a direct fed microbial in combination with a protease, a xylanase, an amylase and a phytase.

In a further aspect, the present invention relates to a feed additive composition for preventing and/or treating coccidiosis and/or necrotic enteritis in a subject.

The present invention yet further provides a method of preventing and/or treating necrotic enteritis and/or coccidiosis wherein an effective amount of a feed additive composition according to the present invention is administered to a subject.

BRIEF DESCRIPTION OF THE DRAWINGS

FIG. 11 shows the amino acid sequence (SEQ ID No. 1) of a pepsin resistant alpha amylase from *Bacillus licheniformis*.

FIG. 12 shows the nucleotide sequence (SEQ ID No. 2) of a pepsin resistant alpha amylase from *Bacillus licheniformis*.

FIG. 13 shows the amino acid sequence (SEQ ID No. 3) of a pepsin resistant alpha amylase from *Trichoderma reesei*.

FIG. 14 shows the nucleotide sequence (SEQ ID No. 4) of a pepsin resistant alpha amylase from *Trichoderma reesei*.

Unchallenged control=Unchallenged Control+phytase

CC=Challenged Control+phytase

CC+Amylase=Challenged Control+phytase+amylase

CC+XAP=Challenged Control+phytase+xylanase+amylase+protease

CC+EP=Challenged Control+phytase+Enviva Pro

CC+EP+Amylase=Challenged Control+phytase+amylase+Enviva Pro

CC+EP+XAP=Challenged Control+phytase+xylanase+amylase+protease+Enviva Pro.

Figure 17:
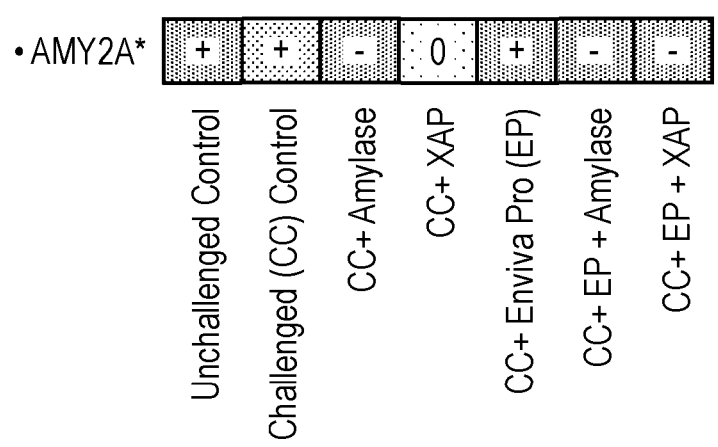

FIG. 17 shows a heat map of expression profile of chicken alpha amylase for all treatments in pancreas at 23 days of age.

Unchallenged control=Unchallenged Control+phytase

CC=Challenged Control+phytase

CC+Amylase=Challenged Control+phytase+amylase

CC+XAP=Challenged Control+phytase+xylanase+amylase+protease

CC+EP=Challenged Control+phytase+Enviva Pro

CC+EP+Amylase=Challenged Control+phytase+amylase+Enviva Pro

CC+EP+XAP=Challenged Control+phytase+xylanase+amylase+protease+Enviva Pro.

Figure 18:
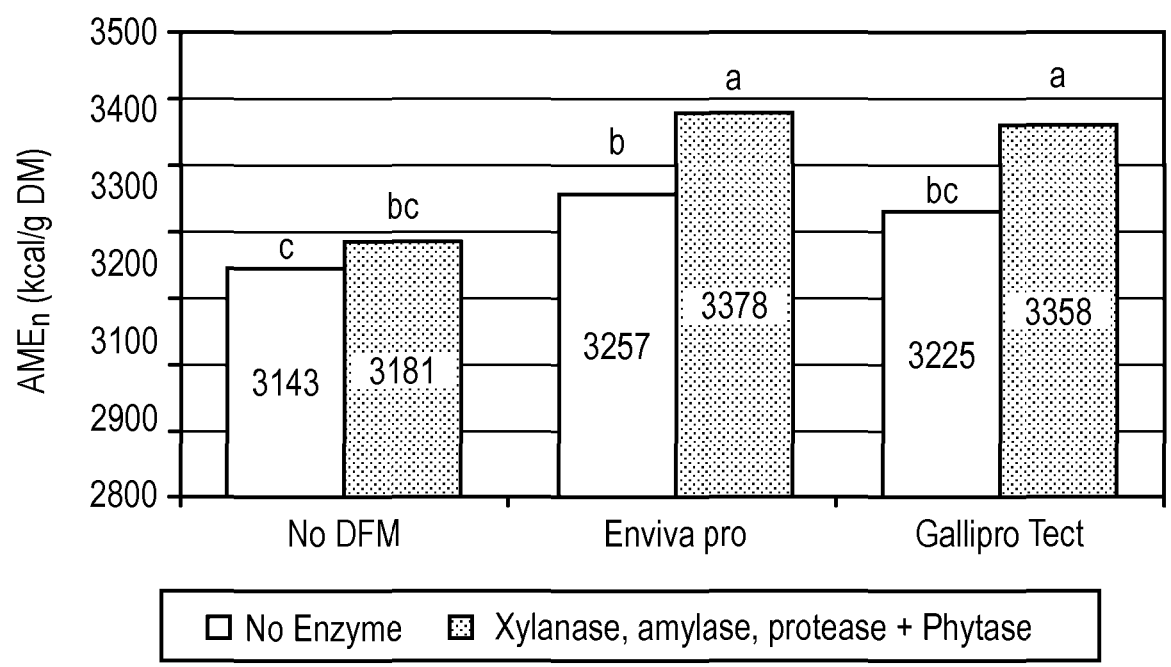

FIG. 18 shows apparent metabolizable energy corrected by nitrogen retention ($AME_n$) of 21 d old broiler chickens. Effect of DFM; P<0.001; Effect of Enzyme; P<0.001; Effect of DFM×Enzyme; P=0.27; Pooled SEM=32 kcal.

Figure 19:
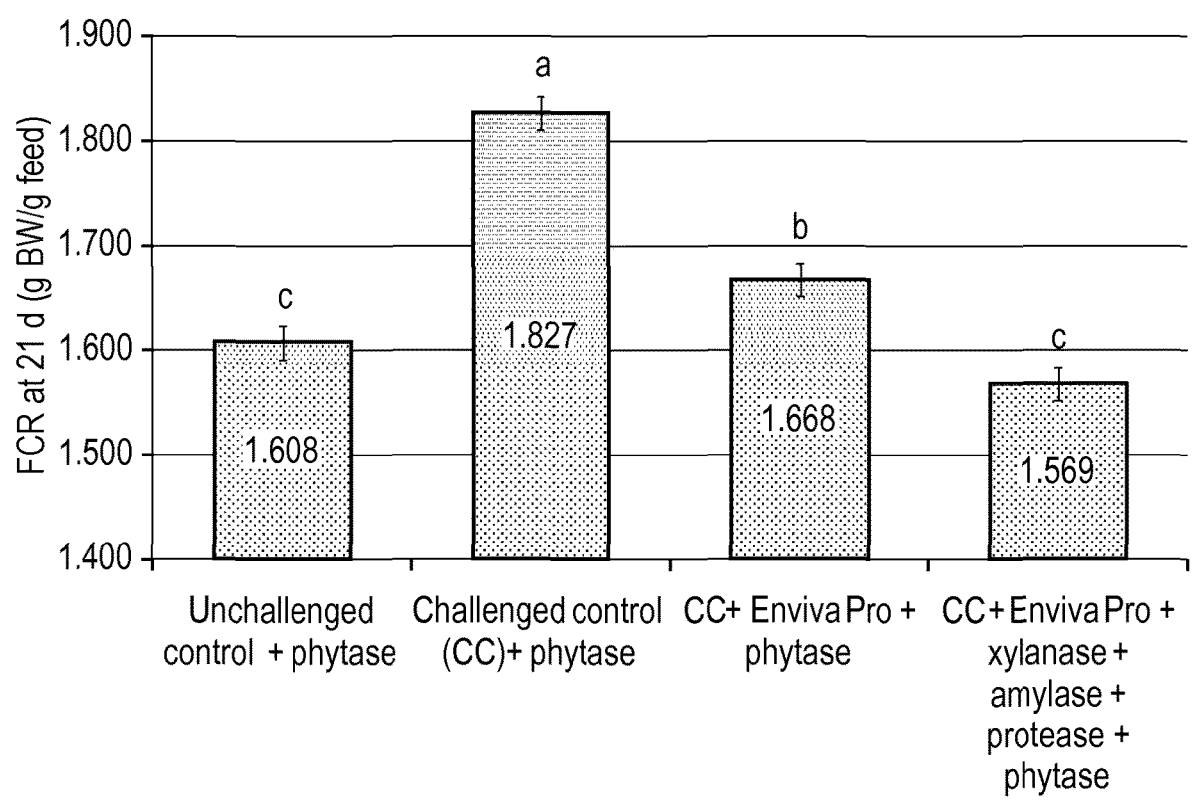

FIG. 19 shows feed conversion ratio (FCR) of broiler chickens in a necrotic enteritis challenge model (Pooled SEM: 0.015).

Figure 20:
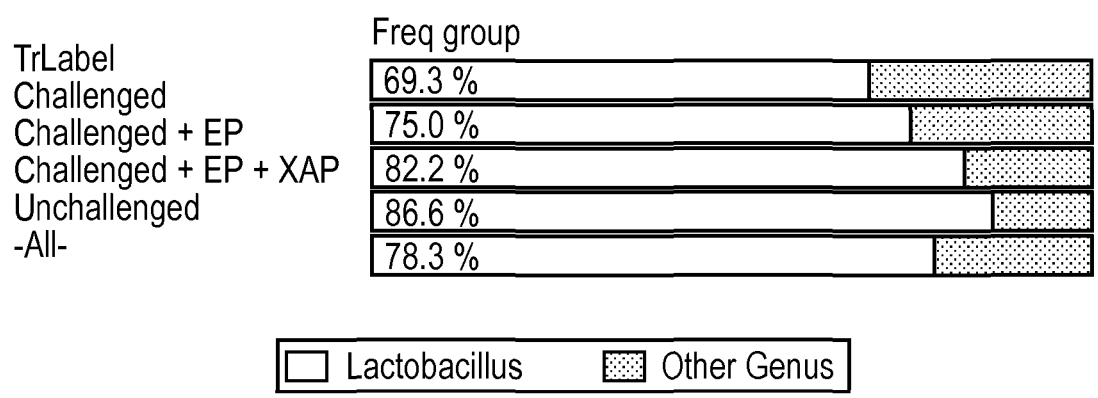

FIG. 20 shows relative proportion of *Lactobacillus* spp. at 21 d in jejunum in broiler chickens, ChSq<0.0001.

DETAILED DESCRIPTION OF THE INVENTION

Preferably each of the enzymes used in the present invention are exogenous to the DFM. In other words the enzymes are preferably added to or admixed with the DFM.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

Direct Fed Microbial (DFM)

The term "microbial" herein is used interchangeably with "microorganism".

Preferably the DFM comprises a viable microorganism. Preferably the DFM comprises a viable bacterium or a viable yeast or a viable fungi.

In one preferred embodiment the DFM comprises a viable bacteria.

The term "viable microorganism" means a microorganism which is metabolically active or able to differentiate.

In one embodiment the DFM may be a spore forming bacterium and hence the term DFM may be comprised of or contain spores, e.g. bacterial spores. Therefore in one embodiment the term "viable microorganism" as used herein may include microbial spores, such as endospores or conidia.

In another embodiment the DFM in the feed additive composition according to the present invention is not comprised of or does not contain microbial spores, e.g. endospores or conidia.

The microorganism may be a naturally occurring microorganism or it may be a transformed microorganism. The microorganism may also be a combination of suitable microorganisms.

In some aspects, the DFM according to the present invention may be one or more of the following: a bacterium, a yeast or a fungi.

Preferably the DFM according to the present invention is a probiotic microorganism.

In the present invention, the term direct fed microbial (DFM) encompasses direct fed bacteria, direct fed yeast, direct fed yeast and combinations thereof.

Preferably the DFM is a direct fed bacterium.

Preferably the DFM is a combination comprising two or more bacteria, e.g. three or more or four or more; or the DFM is a combination comprising two or more bacterial strains, e.g. three or more or four or more.

Preferably the bacterium or bacteria is or are isolated.

Suitably the DFM may comprise a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* and combinations thereof.

In one embodiment the DFM may be selected from the following *Bacillus* spp: *Bacillus subtilis, Bacillus cereus, Bacillus licheniformis* and *Bacillus amyloliquefaciens*.

In one embodiment the DFM may be a combination comprising two or more *Bacillus* strains. In one embodiment the DFM may be a combination of two or more the *Bacillus subtilis* strains 3A-P4 (PTA-6506); 15A-P4 (PTA-6507); 22C-P1 (PTA-6508); 2084 (NRRL B-500130); LSSA01 (NRRL-B-50104); BS27 (NRRL B-50105); BS 18 (NRRL B-50633); and BS 278 (NRRL B-50634).

Strains 3A-P4 (PTA-6506), 15A-P4 (PTA-6507) and 22C-P1 (PTA-6508) are publically available from American Type Culture Collection (ATCC).

Strains 2084 (NRRL B-500130); LSSA01 (NRRL-B-50104); BS27 (NRRL B-50105) are publically available from the Agricultural Research Service Culture Collection (NRRL). Strain *Bacillus subtilis* LSSA01 is sometimes referred to as *B. subtilis* 8.

These strains are taught in U.S. Pat. No. 7,754,469 B2.

*Bacillus subtilis* BS 18 and *Bacillus subtilis* BS 278 were deposited by Andy Madisen of W227 N752 Westmound Dr. Waukesha, Wis. 53186, USA or Danisco USA Inc. of W227 N752 Westmound Dr. Waukesha, Wis. 53186, USA under the Budapest Treaty at the Agricultural Research Service Culture Collection (NRRL) at 1815 North University Street, Peoria, Ill. 61604, United States of America, under deposit numbers NRRL B-50633 and NRRL B-50634, respectively on 9 Jan. 2012.

Andy Madisen of W227 N752 Westmound Dr. Waukesha, Wis. 53186, USA and Danisco USA Inc. of W227 N752 Westmound Dr. Waukesha, Wis. 53186, USA authorise Danisco A/S of Langebrogade 1, PO Box 17, DK-1001, Copenhagen K, Denmark to refer to these deposited biological materials in this patent application and have given unreserved and irrevocable consent to the deposited material being made available to the public.

In some embodiments the DFM may be a combination comprising the *Bacillus subtilis* strains as detailed in the table below:

| *B. subtilis* strain | Bs 2084 | Bs 8 (LSSA01) | Bs 3A-P4 | Bs 15A-P4 | Bs 278 | Bs 18 | Bs 22C-P1 |
|---|---|---|---|---|---|---|---|
| DFM Combination comprises | X | X | X | X | | | |
| | X | X | X | | | | |
| | X | X | | | X | | |
| | X | X | | X | | | |
| | X | | X | X | | | |
| | | X | X | X | | | |
| | X | X | | | | X | |
| | | | X | X | | | X |
| | X | X | | | X | | |

In one embodiment the DFM may be selected from the following *Lactococcus* spp: *Lactococcus cremoris* and *Lactococcus lactis* and combinations thereof.

In one embodiment the DFM may be selected from the following *Lactobacillus* spp: *Lactobacillus buchneri, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus farciminis, Lactobacillus rhamnosus, Lactobacillus crispatus, Lactobacillus gasseri, Lactobacillus johnsonii* and *Lactobacillus jensenii*, and combinations of any thereof.

In one embodiment the DFM may be selected from the following *Bifidobacteria* spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis,* and *Bifidobacterium angulatum*, and combinations of any thereof.

Suitably the DFM may comprise a bacterium from one or more of the following species: *Bacillus subtilis, Bacillus licheniformis, Bacillus amyloliquefaciens, Enterococcus, Enterococcus* spp, and *Pediococcus* spp, *Lactobacillus* spp, *Bifidobacterium* spp, *Lactobacillus acidophilus, Pediococcus acidilactici, Lactococcus lactis, Bifidobacterium bifidum, Bacillus subtilis, Propionibacterium thoenii, Lactobacillus farciminis, Lactobacillus rhamnosus, Megasphaera elsdenii, Clostridium butyricum, Bifidobacterium animalis* ssp. *animalis, Lactobacillus reuteri, Bacillus cereus, Lactobacillus salivarius* ssp. *Salivarius, Propionibacteria* sp and combinations thereof.

The direct fed bacterium used in the present invention may be of the same type (genus, species and strain) or may comprise a mixture of genera, species and/or strains.

Suitably the DFM according to the present invention may be one or more of the products or the microorganisms contained in those products as in the Table below:

| Product Name | Company | Microorganism(s) | Symbiotic ingredients |
|---|---|---|---|
| Enviva Pro ®. (formerly | Danisco A/S | *Bacillus subtilis* strain 2084 Accession No. | |

| Product Name | Company | Microorganism(s) | Symbiotic ingredients |
|---|---|---|---|
| known as Avicorr ®) | | NRRl B-50013, *Bacillus subtilis* strain LSSAO1 Accession No. NRRL B-50104 and *Bacillus subtilis* strain 15A-P4 ATCC Accession No. PTA-6507 | |
| Calsporin ® | Calpis-Japan | *Bacillus subtilis* Strain C3102 | |
| Clostat ® | Kemin Industries Inc. | *Bacillus subtilis* Strain PB6 | |
| Cylactin ® | DSM | *Enterococcus* NCIMB 10415 (SF68) | |
| Gallipro ® & GalliproMax ® | Chr. Hansen A/S | *Bacillus subtilis* Strain C3102 | |
| Gallipro ®Tect ® | Chr. Hansen A/S | *Bacillus licheniformis* | |
| Poultry star ® | Biomin, Inc | *Enterococcus* and *Pediococcus* | Fructo-oligosaccharides |
| Protexin ® | Protexin Int | *Lactobacillus*, *Bifidobacterium* and another | |
| Proflora ® | Alpharma Inc. | *Bacillus subtilis* strain QST 713 | β-Mos β-mannan oligosaccharides and β-glucans |
| Ecobiol ® & Ecobiol ® Plus | Norel S.A. | *Bacillus amyloliquefaciens* CECT-5940 | |
| Fortiflora ® | | *Enterococcus faecium* SF68 | |
| BioPlus2B ® | DSM | *Bacillus subtilis* and *Bacillus licheniformis* | |
| Lactiferm ® | Chr. Hansen | Lactic acid bacteria 7 *Enterococcus faecium* | |
| CSI ® | Danisco A/S | *Bacillus* strain | |
| Yea-Sacc ® | Alltech | *Saccharomyces cerevisiae* | |
| Biomin IMB52 ® | Biomin | *Enterococcus* | |
| Biomin C5 ® | Biomin | *Pediococcus acidilactici, Enterococcus, Bifidobacterium animalis* ssp. *animalis, Lactobacillus reuteri Lactobacillus salivarius* ssp. *salivarius* | |
| Biacton ® | ChemVet | *Lactobacillus farciminis* | |
| Oralin E1707 ® | Chevita GmBH | *Enterococcus* | |
| Probios-pioneer PDFM ® | Chr Hansen | *Enterococcus* (2 strains) *Lactococcus lactis* DSM 11037 | |
| Sorbiflore ® | Danisco Animal Nutrition | *Lactobacillus rhamnosus* and *Lactobacillus farciminis* | |
| Animavit ® | KRKA | *Bacillus subtilis* | |
| Bonvital ® | Lactosan GmbH | *Enterococcus* | |
| Levucell SB 20 ® | Lallemand | *Saccharomyces cerevisiae* | |
| Levucell SC 0 & SC10 ® ME | Lallemand | *Saccharomyces cerevisiae* | |
| Bactocell | Lallemand | *Pediococcus acidilacti* | |
| ActiSaf ® (formerly BioSaf ®) | Le Saffre | *Saccharomyces cerevisiae* | |
| Actisaf ® SC47 | Le Saffre | *Saccharomyces cerevisiae* NCYC Sc47 | |
| Miya-Gold ® | Miyarisan Pharma | *Clostridium butyricum* | |
| Fecinor and Fecinor Plus ® | Norel S.A | *Enterococcus* | |
| InteSwine ® | ntegro Gida ve Ticaret AS represented by RM Associates Ltd | *Saccharomyces cerevisiae* NCYC R-625 | |

-continued

| Product Name | Company | Microorganism(s) | Symbiotic ingredients |
|---|---|---|---|
| BioSprint ® | ProSol SpA | *Saccharomyces cerevisia* | |
| Provita ® | Provita | *Enterococcus* and *Lactobacillus rhamnosus* | |
| PepSoyGen-C ® | Regal BV (Nutraferma) | *Bacillus subtilis* and *Aspergillus oryzae* | |
| Toyocerin ® | Rubinum | *Bacillus cereus* | |
| TOYOCERIN ® | Rubinum | *Bacillus cereus* var. *toyoi* NCIMB 40112/CNCM I-1012 | |

In one embodiment suitably the DFM may be Enviva Pro®. Enviva Pro® is commercially available from Danisco A/S and is a combination of *Bacillus* strain 2084 Accession No. NRR1 B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

Suitably, the DFM may comprise a yeast from the genera: *Saccharomyces* spp.

Preferably the DFM to be used in accordance with the present invention is a microorganism which is generally recognised as safe and, which is preferably GRAS approved.

A skilled person will readily be aware of specific species and or strains of microorganisms from within the genera described herein which are used in the food and/or agricultural industries and which are generally considered suitable for animal consumption.

Preferably, the DFM used in accordance with the present invention is one which is suitable for animal consumption.

Advantageously, where the product is a feed or feed additive composition, the viable DFM should remain effective through the normal "sell-by" or "expiration" date of the product during which the feed or feed additive composition is offered for sale by the retailer. The desired lengths of time and normal shelf life will vary from feedstuff to feedstuff and those of ordinary skill in the art will recognise that shelf-life times will vary upon the type of feedstuff, the size of the feedstuff, storage temperatures, processing conditions, packaging material and packaging equipment.

In some embodiments it is important that the DFM is tolerant to heat, i.e. is thermotolerant. This is particularly the case where the feed is pelleted. Therefore in one embodiment the DFM may be a thermotolerant microorganism, such as a thermotolerant bacteria, including for example *Bacillus* spp.

In some embodiments it may be preferable that the DFM is a spore producing bacteria, such as Bacilli, e.g. *Bacillus* spp. Bacilli are able to from stable endospores when conditions for growth are unfavorable and are very resistant to heat, pH, moisture and disinfectants.

In one embodiment suitably the DFM may decrease or prevent intestinal establishment of pathogenic microorganism (such as *Clostridium perfringens* and/or *E. coli* and/or *Salmonella* spp and/or *Campylobacter* spp.).

The DFM according to the present invention may be any suitable DFM. In one embodiment the following assay "DFM ASSAY" may be used to determine the suitability of a microorganism to be a DFM. For the avoidance of doubt in one embodiment a DFM selected as an inhibitory strain (or an antipathogen DFM) in accordance with the "DFM ASSAY" taught herein is a suitable DFM for use in accordance with the present invention, i.e. in the feed additive composition according to the present invention.

DFM Assay:

Tubes were seeded each with a representative pathogen from a representative cluster.

Supernatant from a potential DFM grown aerobically or anaerobically was added to the seeded tubes and incubated.

After incubation, the optical density (OD) of the control and supernatant treated tubes was measured for each pathogen.

Colonies of (potential DFM) strains that produced a lowered OD compared with the control were classified as an inhibitory strain (or an antipathogen DFM).

The DFM assay as used herein is explained in more detail in US2009/0280090—incorporated herein by reference.

Preferably the representative pathogen used in assay is one (or more) of the following: *Clostridium*, such as *Clostridium perfringens* and/or *Clostridium difficile*, and/or *E. coli* and/or *Salmonella* spp and/or *Campylobacter* spp. In one preferred embodiment the assay is conducted with one or more of *Clostridium perfringens* and/or *Clostridium difficile* and/or *E. coli*, preferably *Clostridium perfringens* and/or *Clostridium difficile*, more preferably *Clostridium perfringens*.

In one embodiment the DFM of the present invention is preferably an antipathogen.

The term "antipathogen" as used herein means the DFM counters an effect (negative effect) of a pathogen.

In one embodiment to determine if a DFM is an antipathogenic DFM the above mentioned DFM assay may be used. A DFM is considered to be an antipathogen or antipathogenic DFM if it is classed as an inhibitory strain in the above mentioned "DFM assay", for example when the pathogen is *Clostridium perfringens*.

In one embodiment the antipathogen DFM may be one or more of the following bacteria:

*Bacillus subtilis* strain 2084 Accession No. NRRL B-50013,
*Bacillus subtilis* strain LSSAO1 Accession No. NRRL B-50104,
*Bacillus subtilis* strain 15A-P4 ATCC Accession No. PTA-6507,
*Bacillus subtilis* strain 3A-P4 ATCC Accession No. PTA-6506, and
*Bacillus subtilis* strain BS27 ATCC Accession No. NRRL B-50105.

For the avoidance of doubt these strains are available and are referred to in U.S. Pat. No. 7,754,459 B.

In one embodiment the DFM used in accordance with the present invention is not *Lactobacillus gasseri* BNR 17 Strain Acc No. KCTC 10902BP as taught in WO2008/016214.

Preferably the DFM is not an inactivated microorganism.

In one embodiment the DFM as used here is a composition comprising one or more DFM microorganisms as described herein. The composition may additionally comprise the enzymes of the present invention. The composition can be fed to an animal as a direct-fed microbial (DFM). One or more carrier(s) or other ingredients can be added to the DFM. The DFM may be presented in various physical forms, for example, as a top dress, as a water soluble concentrate for use as a liquid drench or to be added to a milk replacer, gelatin capsule, or gels. In one embodiment of the top dress form, freeze-dried fermentation product is added to a carrier, such as whey, maltodextrin, sucrose, dextrose, limestone (calcium carbonate), rice hulls, yeast culture, dried starch, and/or sodium silico aluminate. In one embodiment of the water soluble concentrate for a liquid drench or milk replacer supplement, freeze-dried fermentation product is added to a water soluble carrier, such as whey, maltodextrin, sucrose, dextrose, dried starch, sodium silico aluminate, and a liquid is added to form the drench or the supplement is added to milk or a milk replacer. In one embodiment of the gelatin capsule form, freeze-dried fermentation product is added to a carrier, such as whey, maltodextrin, sugar, limestone (calcium carbonate), rice hulls, yeast culture dried starch, and/or sodium silico aluminate. In one embodiment, the bacteria and carrier are enclosed in a degradable gelatin capsule. In one embodiment of the gels form, freeze-dried fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The DFM(s) may optionally be admixed with a dry formulation of additives including but not limited to growth substrates, enzymes, sugars, carbohydrates, extracts and growth promoting micro-ingredients. The sugars could include the following: lactose; maltose; dextrose; maltodextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) or composition comprising same can then be added to animal feed or a feed premix, added to an animal's water, or administered in other ways known in the art (preferably simultaneously with the enzymes of the present invention). A feed for an animal can be supplemented with one or more DFM(s) described herein or with a composition described herein.

By "a mixture of at least two strains," is meant a mixture of two, three, four, five, six or even more strains. In some embodiments of a mixture of strains, the proportions can vary from 1% to 99%. Other embodiments of a mixture of strains are from 25% to 75%. Additional embodiments of a mixture of strains are approximately 50% for each strain. When a mixture comprises more than two strains, the strains can be present in substantially equal proportions or in different proportions in the mixture.

The DFM may be dosed appropriately.

Suitably dosages of DFM in the feed may be between about $1 \times 10^3$ CFU/g feed to about $1 \times 10^9$ CFU/g feed, suitably between about $1 \times 10^4$ CFU/g feed to about $1 \times 10^8$ CFU/g feed, suitably between about $7.5 \times 10^4$ CFU/g feed to about $1 \times 10^7$ CFU/g feed.

In one embodiment the DFM is dosed in the feedstuff at more than about $1 \times 10^3$ CFU/g feed, suitably more than about $1 \times 10^4$ CFU/g feed, suitably more than about $7.5 \times 10^4$ CFU/g feed.

Suitably dosages of DFM in the feed additive composition may be between about $1 \times 10^5$ CFU/g composition to about $1 \times 10^{13}$ CFU/g composition, suitably between about $1 \times 10^6$ CFU/g composition to about $1 \times 10^{12}$ CFU/g composition, suitably between about $3.75 \times 10^7$ CFU/g composition to about $1 \times 10^{11}$ CFU/g composition.

In one embodiment the DFM is dosed in the feed additive composition at more than about $1 \times 10^5$ CFU/g composition, suitably more than about $1 \times 10^6$ CFU/g composition, suitably more than about $3.75 \times 10^7$ CFU/g composition.

In one embodiment the DFM is dosed in the feed additive composition at more than about $2 \times 10^5$ CFU/g composition, suitably more than about $2 \times 10^6$ CFU/g composition, suitably more than about $3.75 \times 10^7$ CFU/g composition.

As used herein the term "CFU" means colony forming units and is a measure of viable cells in which a colony represents an aggregate of cells derived from a single progenitor cell.

Xylanase

Xylanase is the name given to a class of enzymes which degrade the linear polysaccharide beta-1,4-xylan into xylose, thus breaking down hemicellulose, one of the major components of plant cell walls.

The xylanase for use in the present invention may be any commercially available xylanase.

Suitably the xylanase may be an endo-1,4-β-d-xylanase (classified as E.C. 3.2.1.8) or a 1,4 β-xylosidase (classified as E.C. 3.2.1.37).

In one embodiment preferably the xylanase in an endoxylanase, e.g. an endo-1,4-β-d-xylanase. The classification for an endo-1,4-β-d-xylanase is E.C. 3.2.1.8.

In one embodiment the present invention relates to a DFM in combination with an endoxylanase, e.g. an endo-1,4-β-d-xylanase, and another enzyme.

All E.C. enzyme classifications referred to here relate to the classifications provided in Enzyme Nomenclature—Recommendations (1992) of the nomenclature committee of the International Union of Biochemistry and Molecular Biology—ISBN 0-12-226164-3.

Suitably, the xylanase for use in the present invention may be a xylanase from *Bacillus, Trichoderma, Thermomyces, Aspergillus* and *Penicillium*.

In one embodiment the xylanase may be the xylanase in Axtra XAP® or Avizyme 1502®, both commercially available products from Danisco A/S.

In one preferred embodiment the xylanase for use in the present invention may be one or more of the xylanases in one or more of the commercial products below:

| Commercial Name ® | Company | Xylanase type | Xylanase source |
|---|---|---|---|
| Allzyme PT | Alltech | endo-1,4-β-xylanase | *Aspergillus Niger* |
| Amylofeed | Andrés Pintaluba S.A | endo-1,4-β-xylanase | *Aspergillus Niger* (phoenicis) |
| Avemix 02 CS | Aveve | endo-1,4-β-xylanase | *Trichoderma reesei* |
| AveMix XG 10 | Aveve, NL | endo-1,4-β-xylanase | *Trichoderma reesei* |
| Avizyme 1100 | Danisco | endo-1,4-β-xylanase | *Trichoderma longibrachiatum* |
| Avizyme 1110 | Danisco | endo-1,4-β-xylanase | *Trichoderma longibrachiatum* |
| Avizyme 1202 | Danisco | endo-1,4-β-xylanase | *Trichoderma longibrachiatum* |
| Avizyme 1210 | Danisco | endo-1,4-β-xylanase | *Trichoderma longibrachiatum* |
| Avizyme 1302 | Danisco | endo-1,4-β-xylanase | *Trichoderma longibrachiatum* |
| Avizyme 1500 | Danisco | endo-1,4-β-xylanase | *Trichoderma longibrachiatum* |
| Avizyme 1505 | Danisco | endo-1,4-β-xylanase | *Trichoderma longibrachiatum* |
| Avizyme SX | Danisco | endo-1,4-β-xylanase | *Trichoderma longibrachiatum* |
| Belfeed MP100 | Beldem | endo-1,4-β-xylanase | *Bacillus subtilis* |
| Biofeed Plus | DSM | endo-1,4-β-xylanase | *Humicola insolens* |
| Danisco Glycosidase (TPT/L) | Danisco Animal Nutrition | endo-1,4-β-xylanase | *Trichoderma reesei* |
| Danisco Xylanase | Danisco | endo-1,4-β-xylanase | *Trichoderma reesei* |
| Econase XT | AB Vista | endo-1,4-β-xylanase | *Trichoderma reesei* |
| Endofeed ® DC | Andres Pintaluba S.A. | endo-1,4-β-xylanase | *Aspergillus Niger* |
| Feedlyve AXL | Lyven | endo-1,4-β-xylanase | *Trichoderma longibrachiatum* |
| Grindazym GP | Danisco | endo-1,4-β-xylanase | *Aspergillus Niger* |
| Grindazym GV | Danisco | endo-1,4-β-xylanase | *Aspergillus Niger* |
| Hostazym X | Huvepharma | endo-1,4-β-xylanase | *Trichoderma longibrachiatum* |
| Kemzyme Plus Dry | Kemin | endo-1,4-β-xylanase | *Trichoderma viride* |
| Kemzyme Plus Liquid | Kemin | endo-1,4-β-xylanase | *Trichoderma viride* |
| Kemzyme W dry | Kemin | endo-1,4-β-xylanase | *Trichoderma viride* |
| Kemzyme W liquid | Kemin | endo-1,4-β-xylanase | *Trichoderma viride* |
| Natugrain | BASF | endo-1,4-β-xylanase | *Trichoderma longibrachiatum* |
| Natugrain TS Plus | BASF | endo-1,4-β-xylanase | *Aspergillus Niger* |
| Natugrain Wheat | BASF | endo-1,4-β-xylanase | *Aspergillus Niger* |
| Natugrain ® TS/L | BASF | endo-1,4-β-xylanase | *Aspergillus Niger* |
| Natuzyme | Bioproton | endo-1,4-β-xylanase | *Trichoderma longibrachiatum/ Trichoderma reesei* |
| Porzyme 8100 | Danisco | endo-1,4-β-xylanase | *Trichoderma longibrachiatum* |
| Porzyme 8300 | Danisco | endo-1,4-β-xylanase | *Trichoderma longibrachiatum* |
| Porzyme 9102 | Danisco | endo-1,4-β-xylanase | *Trichoderma longibrachiatum* |
| Porzyme 9310/Avizyme 1310 | Danisco | endo-1,4-β-xylanase | *Trichoderma longibrachiatum* |
| Porzyme tp100 | Danisco | endo-1,4-β-xylanase | *Trichoderma longibrachiatum* |
| Ronozyme AX | DSM | endo-1,4-β-xylanase | *Thermomyces lanuginosus* gene expressed in *Aspergillus oryzae* |
| Ronozyme WX | DSM/ Novozymes | endo-1,4-β-xylanase | *Thermomyces lanuginosus* gene expressed in *Aspergillus oryzae* |
| Rovabio Excel | Adi sseo | endo-1,4-β-xylanase | *Penicillium funiculosum* |
| Roxazyme G2 | DSM/Novozymes | endo-1,4-β-xylanase | *Trichoderma longibrachiatum* |
| Safizym X | Le Saffre | endo-1,4-β-xylanase | *Trichoderma longibrachiatum* |
| Xylanase | Lyven | endo-1,4-β-xylanase | *Trichoderma longibrachiatum* |

Preferably, the xylanase is present in the feedstuff in range of about 500 XU/kg to about 16,000 XU/kg feed, more preferably about 750 XU/kg feed to about 8000 XU/kg feed, and even more preferably about 1000 XU/kg feed to about 4000 XU/kg feed In one embodiment the xylanase is present in the feedstuff at more than about 500 XU/kg feed, suitably more than about 600 XU/kg feed, suitably more than about 700 XU/kg feed, suitably more than about 800 XU/kg feed, suitably more than about 900 XU/kg feed, suitably more than about 1000 XU/kg feed.

In one embodiment the xylanase is present in the feedstuff at less than about 16,000 XU/kg feed, suitably less than about 8000 XU/kg feed, suitably less than about 7000 XU/kg feed, suitably less than about 6000 XU/kg feed, suitably less than about 5000 XU/kg feed, suitably less than about 4000 XU/kg feed.

Preferably, the xylanase is present in the feed additive composition in range of about 100 XU/g to about 320,000 XU/g composition, more preferably about 300 XU/g composition to about 160,000 XU/g composition, and even more preferably about 500 XU/g composition to about 50,000 XU/g composition, and even more preferably about 500 XU/g composition to about 40,000 XU/g composition.

In one embodiment the xylanase is present in the feed additive composition at more than about 100 XU/g composition, suitably more than about 200 XU/g composition, suitably more than about 300 XU/g composition, suitably more than about 400 XU/g composition, suitably more than about 500 XU/g composition.

In one embodiment the xylanase is present in the feed additive composition at less than about 320,000 XU/g composition, suitably less than about 160,000 XU/g composition, suitably less than about 50,000 XU/g composition, suitably less than about 40,000 XU/g composition, suitably less than about 30000 XU/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from a oat-spelt-xylan substrate per min at pH 5.3 and 50° C. (Bailey, M. J. Biely, P. and Poutanen, K., Journal of Biotechnology, Volume 23, (3), May 1992, 257-270).

In one embodiment suitably the enzyme is classified using the E.C. classification above, and the E.C. classification designates an enzyme having that activity when tested in the assay taught herein for determining 1 XU.

Amylase

Amylase is the name given to a class of enzymes capable of hydrolysing starch to shorter-chain oligosaccharides such as maltose. The glucose moiety can then be more easily transferred from maltose to a monoglyceride or glycosyl-monoglyceride than from the original starch molecule.

The term amylase includes α-amylases (E.C. 3.2.1.1), G4-forming amylases (E.C. 3.2.1.60), β-amylases (E.C. 3.2.1.2) and γ-amylases (E.C. 3.2.1.3).

In one embodiment preferably the amylase is an α-amylase. α-Amylases are classified as (E.C. 3.2.1.1).

These can include amylases of bacterial or fungal origin, chemically modified or protein engineered mutants are included.

In one embodiment preferably the amylase may be an amylase, e.g. an α-amylase, from *Bacillus licheniformis* and/or an amylase, e.g. an α-amylase, from *Bacillus amyloliquefaciens*.

In one embodiment the α-amylase may be the α-amylase in Axtra XAP® or Avizyme 1502®, both commercially available products from Danisco A/S.

In another embodiment the amylase may be a pepsin resistant α-amylase, such as a pepsin resistant *Trichoderma* (such as *Trichoderma reesei*) alpha amylase. A suitably pepsin resistant α-amylase is taught in UK application number 1011513.7 (which is incorporated herein by reference) and PCT/IB2011/053018 (which is incorporated herein by reference).

In one embodiment the amylase may be a pepsin resistant α-amylase comprising or consisting of an amino acid sequence:
  i) as set forth in SEQ ID No. 1 or SEQ ID No. 3;
  ii) as set forth in SEQ ID No. 1 or SEQ ID No. 3 except for one or several amino acid additions/insertions, deletions or substitutions;
  iii) having at least 85% (preferably, at least 90%, 95%, 97%, 98% or 99%) identity to SEQ ID No. 1 or at least 70% (preferably, at least 75%, 80%, 85%, 90%, 95%, 97%, 98% or 99%) identity to SEQ ID No. 3;
  iv) which is produced by expression of a nucleotide sequence comprising the sequence of SEQ ID No. 2 or SEQ ID No. 4;
  v) which is produced by expression of a nucleotide sequence which differs from SEQ ID No. 2 or SEQ ID No. 4 due to the degeneracy of the genetic code;
  vi) which is produced by expression of a nucleotide sequence which differs from SEQ ID No. 2 or SEQ ID No. 4 by one or several nucleotide additions/insertions, deletions or substitutions; or
  vii) which is produced by expression of a nucleotide sequence which has at least 70% (preferably, at least 75%, 80%, 85%, 90%, 95%, 97%, 98% or 99%) identity to SEQ ID No. 2 or SEQ ID No. 4.

The pepsin resistant alpha amylase may also be encoded by a nucleotide sequence which hybridises to SEQ ID No. 2 or SEQ ID No. 4 under stringent or highly stringent conditions.

In one preferred embodiment the amylase for use in the present invention may be one or more of the amylases in one or more of the commercial products below:

| Commercial product ® | Company | Amylase type | Amylase source |
| --- | --- | --- | --- |
| Amylofeed | Andrés Pintaluba S.A | alpha amylase | *Aspergillus oryzae* |
| Avizyme 1500 | Danisco | alpha amylase | *Bacillus amyloliquefaciens* |
| Avizyme 1505 | Danisco | alpha amylase | *Bacillus amyloliquefaciens* |
| Kemzyme Plus Dry | Kemin | alpha-amylase | *Bacillus amyloliquefaciens* |
| Kemzyme Plus Liquid | Kemin | alpha-amylase | *Bacillus amyloliquefaciens* |
| Kemzyme W dry | Kemin | alpha-amylase | *Bacillus amyloliquefaciens* |
| Kemzyme W liquid | Kemin | alpha-amylase | *Bacillus amyloliquefaciens* |
| Natuzyme | Bioproton | alpha-amylase | *Trichoderma longibrachiatum/ Trichoderma reesei* |
| Porzyme 8100 | Danisco | alpha-amylase | *Bacillus amyloliquefaciens* |
| Porzyme tp100 | Danisco | alpha-amylase | *Bacillus amyloliquefaciens* |
| Ronozyme A | DSM/Novozymes | alpha-amylase | *Bacillus amyloliquefaciens* |
| Ronozyme AX | DSM | alpha-amylase | *Bacillus amyloliquefaciens* |
| Ronozyme® RumiStar (L/CT) | DSM/ Novozymes | alpha-amylase | *Bacillus stearothermophilus* expressed in *Bacillus licheniformis* |

In one embodiment the amylase may be a maltogenic alpha-amylase from *Bacillus* (see EP 120 693). This amylase is commercially available under the trade name Novamyl™ (Novo Nordisk A/S, Denmark). Novamyl is described in detail in International Patent Publication WO 91/104669.

Preferably, the amylase is present in the feedstuff in range of about 50 AU/kg to about 10,000 AU/kg feed, more preferably about 70 AU/kg feed to about 7500 AU/kg feed, more preferably about 70 AU/kg feed to about 5000 AU/kg feed and even more preferably about 100 AU/kg feed to about 2000 AU/kg feed.

In one embodiment the amylase is present in the feedstuff at more than about 50 AU/kg feed, suitably more than about 60 AU/kg feed, suitably more than about 70 AU/kg feed, suitably more than about 80 AU/kg feed, suitably more than about 90 AU/kg feed, suitably more than about 100 AU/kg feed.

In one embodiment the amylase is present in the feedstuff at less than about 10,000 AU/kg feed, suitably less than about 8000 AU/kg feed, suitably less than about 7000 AU/kg feed, suitably less than about 5000 AU/kg feed, suitably less than about 4000 AU/kg feed, suitably less than about 3000 AU/kg feed, suitably less than about 2000 AU/kg feed.

Preferably, the amylase is present in the feed additive composition in range of about 10 AU/kg to about 200,000

AU/g composition, more preferably about 30 AU/g composition to about 100,000 AU/g composition, and even more preferably about 40 AU/g composition to about 50,000 AU/g composition, and even more preferably about 50 AU/g composition to about 20,000 AU/g composition.

In one embodiment the amylase is present in the feed additive composition at more than about 10 AU/g composition, suitably more than about 20 AU/g composition, suitably more than about 30 AU/g composition, suitably more than about 40 AU/g composition, suitably more than about 50 AU/g composition.

In one embodiment the amylase is present in the feed additive composition at less than about 200,000 AU/g composition, suitably less than about 100,000 AU/g composition, suitably less than about 50,000 AU/g composition, suitably less than about 40,000 AU/g composition, suitably less than about 30000 AU/g composition, suitably less than about 20000 AU/g composition.

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

1 TAU (α-amylase activity) is the amount of enzyme required to release (in the presence of excess α-glucosidase) 0.20 μmol of glucosidic linkages (expressed as p-nitrophenol equivalents) from a maltoheptaoside substrate per minute at pH 8.0 and 40° C. This may be referred to herein as the assay for determining 1 TAU unit.

In one embodiment suitably the enzyme is classified using the E.C. classification above, and the E.C. classification designates an enzyme having that activity when tested in the assay taught herein for determining 1 AU.

Protease

The term protease as used herein is synonymous with peptidase or proteinase.

The protease for use in the present invention may be a subtilisin (E.C. 3.4.21.62) or a bacillolysin (E.C. 3.4.24.28) or an alkaline serine protease (E.C. 3.4.21.x) or a keratinase (E.C. 3.4.x.x).

Preferably the protease in accordance with the present invention is a subtilisin.

Suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In one preferred embodiment the protease for use in the present invention may be one or more of the proteases in one or more of the commercial products below:

| Commercial product ® | Company | Protease type | Protease source |
|---|---|---|---|
| Avizyme 1100 | Danisco A/S | Subtilisin | *Bacillus subtilis* |
| Avizyme 1202 | Danisco A/S | Subtilisin | *Bacillus subtilis* |
| Avizyme 1302 | Danisco A/S | Subtilisin | *Bacillus subtilis* |

-continued

| Commercial product ® | Company | Protease type | Protease source |
|---|---|---|---|
| Avizyme 1500 | Danisco A/S | Subtilisin | *Bacillus subtilis* |
| Avizyme 1505 | Danisco A/S | Subtilisin | *Bacillus subtilis* |
| Kemzyme Plus Dry | Kemin | Bacillolysin | *Bacillus amyloliquefaciens* |
| Kemzyme W dry | Kemin | Bacillolysin | *Bacillus amyloliquefaciens* |
| Natuzyme | Bioproton | Protease | *Trichoderma longibrachiatum/ Trichoderma reesei* |
| Porzyme 8300 | Danisco | Subtilisin | *Bacillus subtilis* |
| Ronozyme ProAct | DSM/ Novozymes | Alkaline serine protease | *Nocardiopsis prasina* gene expressed in *Bacillus licheniformis* |
| Versazyme/ Cibenza DP100 | Novus | Keratinase | *Bacillus licheniformis* |

In one embodiment the protease may be a protease from *B. subtilis*.

In one embodiment the protease may be a *Nocardiopsis* protease available from Novozymes A/S.

Preferably, the protease is present in the feedstuff in range of about 1000 U/kg to about 20,000 PU/kg feed, more preferably about 1500 PU/kg feed to about 10000 PU/kg feed, more preferably about 2000 PU/kg feed to about 6000 PU/kg feed.

In one embodiment the protease is present in the feedstuff at more than about 1000 PU/kg feed, suitably more than about 1500 PU/kg feed, suitably more than about 2000 PU/kg feed.

In one embodiment the protease is present in the feedstuff at less than about 20,000 PU/kg feed, suitably less than about 10000 PU/kg feed, suitably less than about 7000 PU/kg feed, suitably less than about 6000 PU/kg feed.

Preferably, the protease is present in the feed additive composition in range of about 200 PU/g to about 400,000 PU/g composition, more preferably about 300 PU/g composition to about 200,000 PU/g composition, and even more preferably about 5000 PU/g composition to about 100,000 PU/g composition, and even more preferably about 700 PU/g composition to about 70,000 PU/g composition, and even more preferably about 1000 PU/g composition to about 60,000 PU/g composition.

In one embodiment the protease is present in the feed additive composition at more than about 200 PU/g composition, suitably more than about 300 PU/g composition, suitably more than about 400 PU/g composition, suitably more than about 500 PU/g composition, suitably more than about 750 PU/g composition, suitably more than about 1000 PU/g composition.

In one embodiment the protease is present in the feed additive composition at less than about 400,000 PU/g composition, suitably less than about 200,000 PU/g composition, suitably less than about 100,000 PU/g composition, suitably less than about 80,000 PU/g composition, suitably less than about 70000 PU/g composition, suitably less than about 60000 PU/g composition.

It will be understood that one protease unit (PU) is the amount of enzyme that liberates from the substrate (0.6% casein solution) one microgram of phenolic compound (expressed as tyrosine equivalents) in one minute at pH 7.5 (40 mM Na$_2$PO$_4$/lactic acid buffer) and 40° C. This may be referred to as the assay for determining 1 PU.

In one embodiment suitably the enzyme is classified using the E.C. classification above, and the E.C. classification designates an enzyme having that activity when tested in the assay taught herein for determining 1 PU.

Phytase

The phytase for use in the present invention may be classified a 6-phytase (classified as E.C. 3.1.3.26) or a 3-phytase (classified as E.C. 3.1.3.8).

In one embodiment the phytase may be a 6-phytase (E.C. 3.1.3.26).

In one preferred embodiment the phytase for use in the present invention may be one or more of the phytases in one or more of the commercial products below:

| Commercial product ® | Company | Phytase type | Phytase source |
|---|---|---|---|
| Finase | ABVista | 3-phytase | *Trichoderma reesei* |
| Finase EC | ABVista | 6-phytase | *E. coli* gene expressed in *Trichoderma reesei* |
| Natuphos | BASF | 3-phytase | *Aspergillus Niger* |
| Natuzyme | Bioproton | phytase (type not specified) | *Trichoderma longibrachiatum/ Trichoderma reesei* |
| OPTIPHOS ® | Huvepharma AD | 6-phytase | *E. coli* gene expressed in *Pichia pastoris* |
| Phytase sp1002 | DSM | 3-phytase | A consensus gene expressed in *Hansenula polymorpha* |
| Phyzyme XP | Danisco | 6-phytase | *E. coli* gene expressed in *Schizosaccahomyces pombe* |
| Quantum 2500D, 5000L | ABVista | 6-phytase | *E. coli* gene expressed in *Pichia pastoris* or *Trichoderma* |
| Ronozyme Hi-Phos (M/L) | DSM/ Novozymes | 6-phytase | *Citrobacter braakii* gene expressed in *Aspergillus oryzae* |
| Ronozyme NP | DSM/ Novozymes | 6-phytase | *Peniphora lycii* gene expressed in *Aspergillus oryzae* |
| Ronozyme P | DSM/ Novozymes | 6-phytase | *Peniphora lycii* gene expressed in *Aspergillus oryzae* |
| Rovabio PHY | Adisseo | 3-phytase | *Penicillium funiculosum* |

The term consensus gene as used herein means that the DNA vector used to transform the organism contains a synthetic phytase gene based on a consensus sequence, a URA gene from the non-pathogenic yeast *Saccharomyces cerevisiae* and the origin of replication of the *Escherichia coli* plasmid pBR322.

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter braakii* YH-15 as disclosed in WO 2004/085638, *Citrobacter braakii* ATCC 51113 as disclosed in WO2006/037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius*, *Citrobacter koseri*, *Citrobacter murliniae*, *Citrobacter rodentium*, *Citrobacter sedlakii*, *Citrobacter werkmanii*, *Citrobacter youngae*, *Citrobacter* species polypeptides or variants thereof.

In one embodiment the phytase may be a phytase from *Citrobacter*, e.g. from *Citrobacter freundii*, such as the phytase enzyme(s) taught in WO2006/038128, which reference is incorporated herein by reference.

In preferred embodiments, the phytase is preferably *E. coli* phytase marketed under the name Phyzyme XP™ by Danisco A/S.

Alternatively the phytase may be a *Buttiauxella* phytase, e.g. a *Buttiauxella agrestis* phytase, for example, the phytase enzymes taught in WO 2006/043178, WO 2008/097619, WO2009/129489, WO2008/092901, PCT/US2009/41011 or PCT/IB2010/051804, all of which are incorporated herein by reference.

In one embodiment the phytase may be a phytase from *Hafnia*, e.g. from *Hafnia alvei*, such as the phytase enzyme(s) taught in US2008263688, which reference is incorporated herein by reference.

In one embodiment the phytase may be a phytase from *Aspergillus*, e.g. from *Aspergillus oryzae*.

In one embodiment the phytase may be a phytase from *Penicillium*, e.g. from *Penicillium funiculosum*.

Preferably, the phytase is present in the feedstuff in range of about 200 FTU/kg to about 1000 FTU/kg feed, more preferably about 300 FTU/kg feed to about 750 FTU/kg feed, more preferably about 400 FTU/kg feed to about 500 FTU/kg feed.

In one embodiment the phytase is present in the feedstuff at more than about 200 FTU/kg feed, suitably more than about 300 FTU/kg feed, suitably more than about 400 FTU/kg feed.

In one embodiment the phytase is present in the feedstuff at less than about 1000 FTU/kg feed, suitably less than about 750 FTU/kg feed.

Preferably, the phytase is present in the feed additive composition in range of about 40 FTU/g to about 40,000 FTU/g composition, more preferably about 80 FTU/g composition to about 20,000 FTU/g composition, and even more preferably about 100 FTU/g composition to about 10,000 FTU/g composition, and even more preferably about 200 FTU/g composition to about 10,000 FTU/g composition.

In one embodiment the phytase is present in the feed additive composition at more than about 40 FTU/g composition, suitably more than about 60 FTU/g composition, suitably more than about 100 FTU/g composition, suitably more than about 150 FTU/g composition, suitably more than about 200 FTU/g composition.

In one embodiment the phytase is present in the feed additive composition at less than about 40,000 FTU/g composition, suitably less than about 20,000 FTU/g composition, suitably less than about 15,000 FTU/g composition, suitably less than about 10,000 FTU/g composition.

It will be understood that as used herein 1 FTU (phytase unit) is defined as the amount of enzyme required to release 1 µmol of inorganic orthophosphate from a substrate in one minute under the reaction conditions defined in the ISO 2009 phytase assay—A standard assay for determining phytase activity and 1 FTU can be found at International Standard ISO/DIS 30024: 1-17, 2009.

In one embodiment suitably the enzyme is classified using the E.C. classification above, and the E.C. classification designates an enzyme having that activity when tested in the assay taught herein for determining 1 FTU.

Advantages

The interaction of DFMs with enzymes is complicated and without wishing to be bound by theory, it is very surprising that we can see an improvement in the subject's resistance to necrotic enteritis, e.g. that we see a reduction in lesion scores for instance. Prior to the present invention the combination of DFMs and enzymes (e.g. as taught herein) had not been taught for this specific purpose.

One advantage of the present invention is that the feed additive composition according to the present invention can avoid the negative effects of necrotic enteritis or can be used for improving the subject's resistance to necrotic enteritis.

Without wishing to be bound by theory, phytase catalyses the sequential hydrolysis of phytate, a principal storage form of phosphorus in cereals and legumes, to less phosphorylated myo-inositol derivatives with concomitant release of inorganic phosphate. Hydrolysis of phytate causes a reduction of endogenous losses of amino acids to the intestinal lumen. A reduction of endogenous amino acid losses in the intestine reduces the availability of nitrogen for bacterial growth, which helps the activity of DFMs on inhibition of *C. perfringens* and other pathogenic bacteria.

Without wishing to be bound in theory proteases cause non-specific hydrolysis of dietary protein yielding a variety of polypeptides in the intestinal lumen. Animals finalise protein hydrolysis and absorb such amino acids. However, in the case of enteric pathogenic challenges, pathogenic bacteria may take advantage of higher peptide availability in the lumen of jejunum and ileum. DFMs inhibit the growth of entero-pathogens by for example competing for N sources, as well as by direct inhibition.

In addition, xylanase degrades the linear polysaccharide beta-1,4-xylan into xylose. Without wishing to be bound by theory, the inventors herein have shown that the increased energy digestibility with the combination of DFMs and enzymes is not explained by starch, fat or protein, therefore it must be explained by non-starch polysaccharides.

Amylase activity hydrolyses alpha-bonds of large alpha-linked polysaccharides such as starch yielding dextrins and oligosaccharides, which are mainly absorbed in the small intestine after hydrolysis to maltose and glucose in the gut wall. Surprisingly, rapid starch hydrolysis in the foregut and greater absorption of glucose in the duodenum deprives pathogenic bacteria from an important energy source (glucose) in the jejunum and ileum, which improves the DFM activity because of a competitive advantage against pathogens that cannot use pentoses as efficiently.

In combination the four enzymes and DFMs surprisingly provide a significant improvement on the pathogen reduction and/or resistance to necrotic enteritis compared with other DFM and enzyme combinations and/or DFMs alone and/or enzyme(s) alone.

The specific combination of DFMs and the enzymes taught herein may advantageously lead to reduced mucin secretion. Without wishing to be bound by theory this reduced mucin secretion may result in a reduction of endogenous amino acid losses, and/or may be responsible for improved performance.

The specific combination of DFMs and the enzymes taught herein may advantageously reduce inflammation in the ileum. This can be seen by the downregulation of IFR-g expression in the ileum. The inventors have shown that modulation of immune response may improve performance.

Formulation of the DFM with the Enzymes

The DFM and the enzymes may be formulated in any suitable way to ensure that the formulation comprises viable DFMs and active enzymes.

In one embodiment the DFM and enzymes may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the DFM and/or the enzyme(s) may be coated, for example encapsulated. Suitably the DFM and enzymes may be formulated within the same coating or encapsulated within the same capsule. Alternatively one or two or three or four of the enzymes may be formulated within the same coating or encapsulated within the same capsule and the DFM could be formulated in a coating separate to the one or more or all of the enzymes. In some embodiments, such as where the DFM is capable of producing endospores, the DFM may be provided without any coating. In such circumstances, the DFM endospores may be simply admixed with one or two or three or four enzymes. In the latter case, the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment all four enzymes may be coated, e.g. encapsulated, together.

In one embodiment the coating protects the enzymes from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95'C for up to several minutes.

In some embodiments the DFM (e.g. DFM endospores for example) may be diluted using a diluent, such as starch powder, lime stone or the like.

In one embodiment, the composition is in a liquid formulation suitable for consumption preferably such liquid consumption contains one or more of the following: a buffer, salt, sorbitol and/or glycerol.

In another embodiment the feed additive composition may be formulated by applying, e.g. spraying, the enzyme(s) onto a carrier substrate, such as ground wheat for example.

In one embodiment the feed additive composition according to the present invention may be formulated as a premix. By way of example only the premix may comprise one or more feed components, such as one or more minerals and/or one or more vitamins.

In one embodiment the DFM and/or enzymes for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the feed additive composition and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Feed

The feed additive composition of the present invention may be used as—or in the preparation of—a feed.

The term "feed" is used synonymously herein with "feedstuff".

The feed may be in the form of a solution or as a solid—depending on the use and/or the mode of application and/or the mode of administration.

When used as—or in the preparation of—a feed—such as functional feed—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes hay, straw, silage, compressed and pelleted feeds, oils and mixed rations, and also sprouted grains and legumes.

Fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

A feedstuff of the present invention may contain at least 30%, at least 40%, at least 50% or at least 60% by weight corn and soybean meal or corn and full fat soy, or wheat meal or sunflower meal.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In the present invention the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

The term feed in the present invention also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed in the present invention also encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term feed in the present invention also encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the composition of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The feed additive compositions of the present invention may be applied to intersperse, coat and/or impregnate a product (e.g. feedstuff or raw ingredients of a feedstuff) with a controlled amount of DFM and enzymes.

The DFM and enzymes may be used simultaneously (e.g. when they are in admixture together or even when they are delivered by different routes) or sequentially (e.g. they may be delivered by different routes). In one embodiment preferably the DFM and enzymes are applied simultaneously. Preferably the DFM and enzymes are admixed prior to being delivered to a feedstuff or to a raw ingredient of a feedstuff.

The DFM in feed additive compositions according to the present invention—can be added in suitable concentrations—such as for example in concentrations in the final feed product which offer a daily dose of between about $2 \times 10^5$ CFU to about $2 \times 10^{11}$ CFU, suitably between about $2 \times 10^6$ to about $1 \times 10^{10}$, suitably between about $3.75 \times 10^7$ CFU to about $1 \times 10^{10}$ CFU.

Preferably, the feed additive composition of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components and/or DFM that were present/active in the additive before heating to the specified temperature are still present/active after it cools to room temperature. Preferably, at least about 80% of the enzyme components and/or DFM that were present and active in the additive before heating to the specified temperature are still present and active after it cools to room temperature.

In a particularly preferred embodiment the feed additive composition is homogenized to produce a powder.

In an alternative preferred embodiment, the feed additive composition is formulated to granules as described in WO2007/044968 (referred to as TPT granules) incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme and/or DFM.

Preferably, the salt used for the salt coating has a water activity greater than 0.25 or constant humidity greater than 60% at 20° C.

Preferably, the salt coating comprises a $Na_2SO_4$.

The method of preparing a feed additive composition may also comprise the further step of pelleting the powder. The powder may be mixed with other components known in the art.

The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the feed additive composition of the present invention is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

As used herein, the term "feedstuff" refers to a feed material to which one or more feed additive compositions have been added.

It will be understood by the skilled person that different animals require different feedstuffs, and even the same animal may require different feedstuffs, depending upon the purpose for which the animal is reared.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

In one embodiment the feedstuff is not for a layer.

By way of example only a feedstuff for chickens, e.g. broiler chickens may be comprises of one or more of the ingredients listed in the table below, for example in the % ages given in the table below:

| Ingredients | Starter (%) | Finisher (%) |
| --- | --- | --- |
| Maize | 46.2 | 46.7 |
| Wheat Middlings | 6.7 | 10.0 |
| Maize DDGS | 7.0 | 7.0 |
| Soyabean Meal 48% CP | 32.8 | 26.2 |
| An/Veg Fat blend | 3.0 | 5.8 |
| L-Lysine HCl | 0.3 | 0.3 |
| DL-methionine | 0.3 | 0.3 |
| L-threonine | 0.1 | 0.1 |
| Salt | 0.3 | 0.4 |
| Limestone | 1.1 | 1.1 |
| Dicalcium Phosphate | 1.2 | 1.2 |
| Poultry Vitamins and Micro-minerals | 0.3 | 0.3 |

By way of example only the diet specification for chickens, such as broiler chickens, may be as set out in the Table below:

| Diet specification | | |
| --- | --- | --- |
| Crude Protein (%) | 23.00 | 20.40 |
| Metabolizable Energy Poultry (kcal/kg) | 2950 | 3100 |
| Calcium (%) | 0.85 | 0.85 |
| Available Phosphorus (%) | 0.38 | 0.38 |
| Sodium (%) | 0.18 | 0.19 |
| Dig. Lysine (%) | 1.21 | 1.07 |
| Dig. Methionine (%) | 0.62 | 0.57 |
| Dig. Methionine + Cysteine (%) | 0.86 | 0.78 |
| Dig. Threonine (%) | 0.76 | 0.68 |

By way of example only a feedstuff laying hens may be comprises of one or more of the ingredients listed in the table below, for example in the % ages given in the table below:

| Ingredient | Laying phase (%) |
| --- | --- |
| Maize | 10.0 |
| Wheat | 53.6 |
| Maize DDGS | 5.0 |
| Soybean Meal 48% CP | 14.9 |
| Wheat Middlings | 3.0 |
| Soybean Oil | 1.8 |
| L-Lysine HCl | 0.2 |
| DL-methionine | 0.2 |
| L-threonine | 0.1 |
| Salt | 0.3 |
| Dicalcium Phosphate | 1.6 |
| Limestone | 8.9 |
| Poultry Vitamins and Micro-minerals | 0.6 |

By way of example only the diet specification for laying hens may be as set out in the Table below:

| Diet specification | |
| --- | --- |
| Crude Protein (%) | 16.10 |
| Metabolizable Energy Poultry (kcal/kg) | 2700 |
| Lysine (%) | 0.85 |
| Methionine (%) | 0.42 |
| Methionine + Cysteine (%) | 0.71 |
| Threonine (%) | 0.60 |
| Calcium (%) | 3.85 |
| Available Phosphorus (%) | 0.42 |
| Sodium (%) | 0.16 |

By way of example only a feedstuff for turkeys may be comprises of one or more of the ingredients listed in the table below, for example in the % ages given in the table below:

| Ingredient | Phase 1 (%) | Phase 2 (%) | Phase 3 (%) | Phase 4 (%) |
| --- | --- | --- | --- | --- |
| Wheat | 33.6 | 42.3 | 52.4 | 61.6 |
| Maize DDGS | 7.0 | 7.0 | 7.0 | 7.0 |
| Soyabean Meal 48% CP | 44.6 | 36.6 | 27.2 | 19.2 |
| Rapeseed Meal | 4.0 | 4.0 | 4.0 | 4.0 |
| Soyabean Oil | 4.4 | 4.2 | 3.9 | 3.6 |
| L-Lysine HCl | 0.5 | 0.5 | 0.4 | 0.4 |
| DL-methionine | 0.4 | 0.4 | 0.3 | 0.2 |
| L-threonine | 0.2 | 0.2 | 0.1 | 0.1 |
| Salt | 0.3 | 0.3 | 0.3 | 0.3 |
| Limestone | 1.0 | 1.1 | 1.1 | 1.0 |
| Dicalcium Phosphate | 3.5 | 3.0 | 2.7 | 2.0 |

| Ingredient | Phase 1 (%) | Phase 2 (%) | Phase 3 (%) | Phase 4 (%) |
|---|---|---|---|---|
| Poultry Vitamins and Micro-minerals | 0.4 | 0.4 | 0.4 | 0.4 |

By way of example only the diet specification for turkeys may be as set out in the Table below:

| Diet specification | | | | |
|---|---|---|---|---|
| Crude Protein (%) | 29.35 | 26.37 | 22.93 | 20.00 |
| Metabolizable Energy Poultry (kcal/kg) | 2.850 | 2.900 | 2.950 | 3.001 |
| Calcium (%) | 1.43 | 1.33 | 1.22 | 1.02 |
| Available Phosphorus (%) | 0.80 | 0.71 | 0.65 | 0.53 |
| Sodium (%) | 0.16 | 0.17 | 0.17 | 0.17 |
| Dig. Lysine (%) | 1.77 | 1.53 | 1.27 | 1.04 |
| Dig. Methionine (%) | 0.79 | 0.71 | 0.62 | 0.48 |
| Dig. Methionine + Cysteine (%) | 1.12 | 1.02 | 0.90 | 0.74 |
| Dig. Threonine (%) | 1.03 | 0.89 | 0.73 | 0.59 |

By way of example only a feedstuff for piglets may be comprises of one or more of the ingredients listed in the table below, for example in the % ages given in the table below:

| Ingredient | Phase 1 (%) | Phase 2 (%) |
|---|---|---|
| Maize | 20.0 | 7.0 |
| Wheat | 25.9 | 46.6 |
| Rye | 4.0 | 10.0 |
| Wheat middlings | 4.0 | 4.0 |
| Maize DDGS | 6.0 | 8.0 |
| Soyabean Meal 48% CP | 25.7 | 19.9 |
| Dried Whey | 10.0 | 0.0 |
| Soyabean Oil | 1.0 | 0.7 |
| L-Lysine HCl | 0.4 | 0.5 |
| DL-methionine | 0.2 | 0.2 |
| L-threonine | 0.1 | 0.2 |
| L-tryptophan | 0.03 | 0.04 |
| Limestone | 0.6 | 0.7 |
| Dicalcium Phosphate | 1.6 | 1.6 |
| Swine Vitamins and Micro-minerals | 0.2 | 0.2 |
| Salt | 0.2 | 0.4 |

By way of example only the diet specification for piglets may be as set out in the Table below:

| Diet specification | | |
|---|---|---|
| Crude Protein (%) | 21.50 | 20.00 |
| Swine Digestible Energy (kcal/kg) | 3380 | 3320 |
| Swine Net Energy (kcal/kg) | 2270 | 2230 |
| Calcium (%) | 0.80 | 0.75 |
| Digestible Phosphorus (%) | 0.40 | 0.35 |
| Sodium (%) | 0.20 | 0.20 |
| Dig. Lysine (%) | 1.23 | 1.14 |
| Dig. Methionine (%) | 0.49 | 0.44 |
| Dig. Methionine + Cysteine (%) | 0.74 | 0.68 |
| Dig. Threonine (%) | 0.80 | 0.74 |

By way of example only a feedstuff for grower/finisher pigs may be comprises of one or more of the ingredients listed in the table below, for example in the % ages given in the table below:

| Ingredient | Grower/Finisher (%) |
|---|---|
| Maize | 27.5 |
| Soyabean Meal 48% CP | 15.4 |
| Maize DDGS | 20.0 |
| Wheat bran | 11.1 |
| Rice bran | 12.0 |
| Canola seed meal | 10.0 |
| Limestone | 1.6 |
| Dicalcium phosphate | 0.01 |
| Salt | 0.4 |
| Swine Vitamins and Micro-minerals | 0.3 |
| Lysine-HCl | 0.2 |
| Vegetable oil | 0.5 |

By way of example only the diet specification for grower/finisher pigs may be as set out in the Table below:

| Diet specification | |
|---|---|
| Crude Protein (%) | 22.60 |
| Swine Metabolizable Energy (kcal/kg) | 3030 |
| Calcium (%) | 0.75 |
| Available Phosphorus (%) | 0.29 |
| Digestible Lysine (%) | 1.01 |
| Dig. Methionine + Cysteine (%) | 0.73 |
| Digestible Threonine (%) | 0.66 |

Forms

The feed additive composition of the present invention and other components and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, DFM or feed additive compositions of the present invention may be mixed with feed or administered in the drinking water. In one embodiment the dosage range for inclusion into water is about $1 \times 10^3$ CFU/animal/day to about $1 \times 10^{10}$ CFU/animal/day, and more preferably about $1 \times 10^7$ CFU/animal/day.

Suitable examples of forms include one or more of: powders, pastes, boluses, pellets, tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Non-hydroscopic whey is often used as a carrier for DFMs (particularly bacterial DFMs) and is a good medium to initiate growth.

Bacterial DFM containing pastes may be formulated with vegetable oil and inert gelling ingredients.

Fungal products may be formulated with grain by-products as carriers.

In one embodiment preferably the feed additive composition according to the present invention is not in the form of a microparticle system, such as the microparticle system taught in WO2005/123034.

Dosing

The DFM and/or feed additive composition according to the present invention may be designed for one-time dosing or may be designed for feeding on a daily basis.

The optimum amount of the composition (and each component therein) to be used in the combination of the present invention will depend on the product to be treated and/or the method of contacting the product with the composition and/or the intended use for the same.

The amount of DFM and enzymes used in the compositions should be a sufficient amount to be effective and to remain sufficiently effective in improving the performance of the animal fed feed products containing said composition. This length of time for effectiveness should extend up to at least the time of utilisation of the product (e.g. feed additive composition or feed containing same).

The ratio of DFM to each enzyme in the feed can be in the ranges given below:

DFM:phytase (CFU/FTU): In range from $5.0 \times 10^2$ CFU DFM:1 FTU enzyme to $5.0 \times 10^9$ CFU:1 FTU enzyme; preferably in the range from $7.5 \times 10^4$ CFU DFM:1 FTU enzyme to $2.5 \times 10^7$ CFU:1 FTU enzyme.

DFM:xylanase (CFU/XU): In range from $6.25 \times 10^1$ CFU DFM:1 XU enzyme to $2.0 \times 10^9$ CFU:1 XU enzyme; preferably in the range from $1.88 \times 10^4$ CFU DFM:1 XU enzyme to $1.0 \times 10^7$ CFU:1 XU enzyme.

DFM:amylase (CFU/AU): In range from $1.0 \times 10^2$ CFU DFM:1 AU enzyme to $2.0 \times 10^{10}$ CFU:1 AU enzyme; preferably in the range from $3.7 \times 10^4$ CFU DFM:1 AU enzyme to $1.0 \times 10^8$ CFU:1 AU enzyme.

DFM:protease (CFU/PU): In range from $5.0 \times 10^1$ CFU DFM:1 PU enzyme to $1.0 \times 10^9$ CFU:1 PU enzyme; preferably in the range from $1.25 \times 10^4$ CFU DFM:1 PU enzyme to $5.0 \times 10^6$ CFU:1 PU enzyme.

In one embodiment preferably the feedstuff comprises the following:
a protease at at least 4000 PU/kg of feed;
a xylanase at at least 1000 XU/kg to 2000 XU/kg of feed (e.g. Avizyme at 1000 XU/kg of feed or Axtra XAP at at least 2000 XU/kg of feed);
an amylase; at least 1800 AU/kg or 200 TAU/kg of feed (e.g. Avizyme at 1800 AU/kg or Axtra XAP at at least 200 TAU/kg of feed);
a phytase at at least 500 FTU/kg of feed; and
Envivo Pro (DFM) at at least 75,000 CFU/g to 150,000 CFU/g of feed.

In one embodiment preferably the feedstuff comprises the following:
a protease at 4000 PU/kg of feed;
a xylanase at 1000 XU/kg to 2000 XU/kg of feed (e.g. Avizyme at 1000 XU/kg of feed or Axtra XAP at 2000 XU/kg of feed);
an amylase; 1800 AU/kg or 200 TAU/kg of feed (e.g. Avizyme at 1800 AU/kg or Axtra XAP at 200 TAU/kg of feed);
a phytase at 500 FTU/kg of feed; and
Envivo Pro (DFM) at 75,000 CFU/g to 150,000 CFU/g of feed.

In one embodiment preferably the feedstuff comprises the following:
a protease at 5000 PU/kg of feed;
a xylanase at 1250 XU/kg to 2500 XU/kg of feed (e.g. Avizyme at 1000 XU/kg of feed or Axtra XAP at 2500 XU/kg of feed);
an amylase; 2250 AU/kg or 250 TAU/kg of feed (e.g. Avizyme at 1800 AU/kg or Axtra XAP at 250 TAU/kg of feed);
a phytase at 625 FTU/kg of feed; and
Envivo Pro (DFM) at 75,000 CFU/g to 150,000 CFU/g of feed.

In another embodiment the feedstuff comprises the following:
a protease at 2000 PU/kg of feed;
a xylanase at 500 XU/kg to 1000 XU/kg of feed (e.g. Avizyme at 500 XU/kg of feed or Axtra XAP at 1000 XU/kg of feed);
an amylase; 900 AU/kg or 100 TAU/kg of feed (e.g. Avizyme at 900 AU/kg or Axtra XAP at 100 TAU/kg of feed);
a phytase at 500 FTU/kg of feed; and
Envivo Pro (DFM) at 37,500 CFU/g to 75,000 CFU/g of feed.

In a preferred embodiment the feed additive composition comprises sufficient enzyme and DFMs to dose the feedstuff as follows:
a protease at 4000 PU/kg of feed;
a xylanase at 1000 XU/kg to 2000 XU/kg of feed (e.g. Avizyme at 1000 XU/kg of feed or Axtra XAP at 2000 XU/kg of feed);
an amylase; 1800 AU/kg or 200 TAU/kg of feed (e.g. Avizyme at 1800 AU/kg or Axtra XAP at 200 TAU/kg of feed);
a phytase at 500 FTU/kg of feed; and
Envivo Pro (DFM) at 75,000 CFU/g to 150,000 CFU/g of feed.

In a preferred embodiment the feed additive composition comprises sufficient enzyme and DFMs to dose the feedstuff as follows:
a protease at 2000 PU/kg of feed;
a xylanase at 500 XU/kg to 1000 XU/kg of feed (e.g. Avizyme at 500 XU/kg of feed or Axtra XAP at 1000 XU/kg of feed);
an amylase; 900 AU/kg or 100 TAU/kg of feed (e.g. Avizyme at 900 AU/kg or Axtra XAP at 100 TAU/kg of feed);
a phytase at 500 FTU/kg of feed; and
Envivo Pro (DFM) at 37,500 CFU/g to 75,000 CFU/g of feed.

Combination with Other Components

The DFM and enzyme(s) for use in the present invention may be used in combination with other components. Thus, the present invention also relates to combinations. The DFM in combination with a protease, xylanase, amylase and phytase may be referred to herein as "the feed additive composition of the present invention".

The combination of the present invention comprises the feed additive composition of the present invention (or one or more of the constituents thereof) and another component which is suitable for animal consumption and is capable of providing a medical or physiological benefit to the consumer.

In one embodiment preferably the "another component" is not a further enzyme or a further DFM.

The components may be prebiotics. Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Suitable prebiotics include palatinoseoligosaccharide, soybean oligosaccharide, alginate, xanthan, pectin, locust bean gum (LBG), inulin, guar gum, galacto-oligosaccharide (GOS), fructo-oligosaccharide (FOS), non-degradable starch, lactosaccharose, lactulose, lactitol, maltitol, maltodextrin, polydextrose (i.e. Litesse®), lactitol, lactosucrose, soybean oligosaccharides, palatinose, isomalto-oligosaccharides, gluco-oligosaccharides and xylo-oligosaccharides, pectin fragments, dietary fibres, mannan-oligosaccharides.

Dietary fibres may include non-starch polysaccharides, such as arabinoxylans, cellulose and many other plant components, such as resistant dextrins, inulin, lignin, waxes, chitins, pectins, beta-glucans and oligosaccharides.

In one embodiment the present invention relates to the combination of the feed additive composition (or one or more of the constituents thereof) according to the present invention with a prebiotic. In another embodiment the present invention relates to a feed additive composition comprising (or consisting essentially of or consisting of) a DFM in combination with a xylanase, an amylase, a phytase, a protease and a prebiotic.

The prebiotic may be administered simultaneously with (e.g. in admixture together with or delivered simultaneously by the same or different routes) or sequentially to (e.g. by the same or different routes) the feed additive composition (or constituents thereof) according to the present invention.

Other components of the combinations of the present invention include polydextrose, such as Litesse®, and/or a maltodextrin and/or lactitol. These other components may be optionally added to the feed additive composition to assist the drying process and help the survival of DFM.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one embodiment the DFM and/or enzymes may be encapsulated. In one embodiment the feed additive composition and/or DFM and/or enzymes is/are formulated as a dry powder or granule as described in WO2007/044968 (referred to as TPT granules)—reference incorporated herein by reference.

In one preferred embodiment the DFM and/or enzymes for use in the present invention may be used in combination with one or more lipids.

For example, the DFM and/or enzymes for use in the present invention may be used in combination with one or more lipid micelles. The lipid micelle may be a simple lipid micelle or a complex lipid micelle.

The lipid micelle may be an aggregate of orientated molecules of amphipathic substances, such as a lipid and/or an oil.

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

"Carriers" or "vehicles" mean materials suitable for administration of the DFM and/or enzymes and include any such material known in the art such as, for example, any liquid, gel, solvent, liquid diluent, solubilizer, or the like, which is non-toxic and which does not interact with any components of the composition in a deleterious manner.

The present invention provides a method for preparing a feed additive composition comprising admixing a DFM, a xylanase, a protease, a phytase and a amylase with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Concentrates

The DFMs for use in the present invention may be in the form of concentrates. Typically these concentrates comprise a substantially high concentration of a DFM.

Feed additive compositions according to the present invention may have a content of viable cells (colony forming units, CFUs) which is in the range of at least $10^4$ CFU/g (suitably including at least $10^5$ CFU/g, such as at least $10^6$ CFU/g, e.g. at least $10^7$ CFU/g, at least $10^8$ CFU/g, e.g. at least $10^9$ CFU/g) to about $10^{10}$ CFU/g (or even about $10^{11}$ CFU/g or about $10^{12}$ CFU/g).

When the DFM is in the form of a concentrate the feed additive compositions according to the present invention may have a content of viable cells in the range of at least $10^9$ CFU/g to about $10^{12}$ CFU/g, preferably at least $10^{10}$ CFU/g to about $10^{12}$ CFU/g.

Powders, granules and liquid compositions in the form of concentrates may be diluted with water or resuspended in water or other suitable diluents, for example, an appropriate growth medium such as milk or mineral or vegetable oils, to give compositions ready for use.

The DFM or feed additive composition of the present invention or the combinations of the present invention in the form of concentrates may be prepared according to methods known in the art.

In one aspect of the present invention the enzymes or feed is contacted by a composition in a concentrated form.

The compositions of the present invention may be spray-dried or freeze-dried by methods known in the art.

Typical processes for making particles using a spray drying process involve a solid material which is dissolved in an appropriate solvent (e.g. a culture of a DFM in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Subject

The term "subject", as used herein, means an animal that is to be or has been administered with a feed additive composition according to the present invention or a feedstuff comprising said feed additive composition according to the present invention.

The term "subject", as used herein, means an animal. Preferably, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of cows or bulls (including calves), poultry, pigs (including piglets), poultry (including broilers, chickens and turkeys), birds, fish (including freshwater fish, such as salmon, cod, trout and carp, e.g. koi carp, and marine fish, such as sea bass), crustaceans (such as shrimps, mussels and scallops), horses (including race horses), sheep (including lambs).

In one embodiment the term livestock and/or poultry and/or chickens does not include egg layers.

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

In one embodiment the subject may be challenged by an enteric pathogen.

By way of example a subject may have one or more enteric pathogens present in its gut or digestive tract. For example a subject may have one or more enteric pathogens in its gut or digestive tract at a level which:

i) results in loss of performance of the animal and/or ii) is at clinically relevant levels; or iii) is at sub-clinical levels.

The enteric pathogen may be *Clostridium perfringens* for example.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen Retention

Nitrogen retention as used herein means as subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

Survival

The term survival as used herein means the number of subject remaining alive. The term "improved survival" may be another way of saying "reduced mortality".

Carcass Yield and Meat Yield

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

Weight Gain

The present invention further provides a method of increasing weight gain in a subject, e.g. poultry or swine, comprising feeding said subject a feedstuff comprising a feed additive composition according to the present invention.

An "increased weight gain" refers to an animal having increased body weight on being fed feed comprising a feed additive composition compared with an animal being fed a feed without said feed additive composition being present.

Necrotic Enteritis

Necrotic enteritis is an acute or chronic enterotoxemia seen in chickens, turkeys and ducks worldwide, caused by *Clostridium perfringens*. Necrotic enteritis is often characterised by a fibrino-necrotic enteritis, usually of the mid-small intestine. Mortality may be 5-50%, usually around 10%. Infection occurs by faecal-oral transmission. Spores of the causative organism are highly resistant. Predisposing factors include coccidiosis/coccidiasis, diet (high protein), in ducks possibly heavy strains, high viscosity diets (often associated with high rye and wheat inclusions in the diet), contaminated feed and/or water, other debilitating diseases.

The present invention relates to increasing the subject's resistance to necrotic enteritis. In other words, the present invention relates to avoiding or reducing the negative effect of necrotic enteritis.

The term "resistance to" as used herein may encompasses the term "tolerance of". Therefore in one embodiment the subject may not be resistant to necrotic enteritis but the subject may be able to tolerate the necrotic enteritis, i.e. without negative effects on performance of the subject.

In one embodiment the present invention relates to a feed additive composition according to the present invention for treating or preventing necrotic enteritis in a subject. Typically the subject will be one which has been or will be challenged with *Clostridium perfringens* and/or *Eimeria* species. Such challenge may come from the environment, or the application of live microorganisms in the feed or drinking water, e.g. when live coccidia vaccines are used.

In another embodiment the present invention relates to a feed additive composition for preventing and/or treating coccidiosis and/or necrotic enteritis in a subject.

The present invention yet further provides a method of preventing and/or treating necrotic enteritis and/or coccidiosis wherein an effective amount of a feed additive composition according to the present invention is administered to a subject.

Immune Response

Immune response as used herein means one of the multiple ways in which DFMs modulate the immune system of animals, including increased antibody production, up-regulation of cell mediated immunity, up-regulation of pro-inflammatory cytokines, and augmented toll-like receptor signalling. It is understood that immuno-stimulation of the gastro intestinal tract by DFMs may be advantageous to protect the host against disease, and that immuno-suppression of the gastro intestinal tract may be advantageous to the host because less nutrients and energy are used to support the immune function.

Preferably the immune response is a cellular immune response.

Preferably immune response is measure by looking at immune markers.

Pathogenic Bacteria

The term pathogenic bacteria as used herein means for example toxigenic clostridia species, e.g. *Clostridium perfringens* and/or *E. coli* and/or *Salmonella* spp and/or *Campylobacter* spp. In one embodiment the pathogenic bacteria may be Avian pathogenic *E. coli* species.

The present invention may reduce populations of pathogenic bacteria in the gastrointestinal tract of a subject.

Nutrient Excretion

In one embodiment the present invention relates to reducing nutrient excretion in manure. This has positive effects on reducing environmental hazards. For example, in a preferred embodiment the present invention relates to reducing nitrogen and/or phosphorus content in the subject's manure. This, therefore, reduces the amount of nitrogen and/or phosphorus in the environment, which can be beneficial.

Probiotic

For some applications, it is believed that the DFM in the composition of the present invention can exert a probiotic culture effect. It is also within the scope of the present invention to add to the composition of the present invention further probiotic and/or prebiotics.

Here, a prebiotic is:

"a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut.

Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

Isolated

In one aspect, suitably the enzyme or DFM used in the present invention may be in an isolated form. The term "isolated" means that the enzyme or DFM is at least substantially free from at least one other component with which the enzyme or DFM is naturally associated in nature and as found in nature. The enzyme or DFM of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the enzyme and/or DFM according to the present invention is in a purified form. The term "purified" means that the enzyme and/or DFM is present at a high level. The enzyme and/or DFM is desirably the predominant component present in a composition. Preferably, it is present at a level of at least about 90%, or at least about 95% or at least about 98%, said level being determined on a dry weight/dry weight basis with respect to the total composition under consideration.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

Nucleotide Sequence

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by the scope of the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein encompassed in the present invention may be used in conjunction with other proteins, particularly enzymes. Thus the present invention also covers a combination of proteins wherein the combination comprises the protein/enzyme of the present invention and another protein/enzyme, which may be another protein/enzyme according to the present invention.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, complementary sequences are those capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, complementary sequences are those that are capable of hybridising under high stringency conditions (e.g. 65° C. and 0.1×SSC {1×SSC=0.15 M NaCl, 0.015 M Na$_3$citrate pH 7.0}) to the nucleotide sequences presented herein.

In a more preferred aspect, the present invention covers nucleotide sequences that can hybridise to the nucleotide sequence of the present invention, or the complement thereof, under high stringent conditions (e.g. 65° C. and 0.1×SSC).

EXAMPLES

Example 1

Materials and Methods

Three thousand six hundred one-day-old Cobb male chicks were purchased from a commercial hatchery. At study initiation, fifty males were allocated to each treatment pen by blocks. The study consisted of the following treatments (Table 1):

TABLE 1

Experimental design of Example 1.

| Treatment | Clostridium perfringens Challenge | Phytase[1] | Additional enzyme[2] | DFM[3] |
|---|---|---|---|---|
| 1 | No  | 500 FTU/kg | None | None |
| 2 | Yes | 500 FTU/kg | None | None |
| 3 | Yes | 500 FTU/kg | Amylase (200 u/kg) | None |
| 4 | Yes | 500 FTU/kg | Protease (5000 u/kg) | None |
| 5 | Yes | 500 FTU/kg | Xylanase[4] (2000 u/kg) Amylase[4] (200 u/kg) Protease[4] (5000 u/kg) | None |
| 6 | Yes | 500 FTU/kg | None | Enviva Pro ($7.5 \times 10^4$ CFU/g) |
| 7 | Yes | 500 FTU/kg | Amylase (200 u/kg) | Enviva Pro ($7.5 \times 10^4$ CFU/g) |
| 8 | Yes | 500 FTU/kg | Protease (5000 u/kg) | Enviva Pro ($7.5 \times 10^4$ CFU/g) |
| 9 | Yes | 500 FTU/kg | Xylanase[4] (2000 u/kg) Amylase[4] (200 u/kg) Protease[4] (5000 u/kg) | Enviva Pro ($7.5 \times 10^4$ CFU/g) Enviva Pro Enviva Pro |

[1]Phytase from *E. coli*.
[2]Amylase from *Bacillus licheniformis*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Axtra XAP ® provided by Danisco A/S.

Bird weights by pen were recorded at study initiation, 23 d, 35 d, and termination (42 d). The pen was the unit of measure. Broiler diets were fed as crumbles (starter) or pellets (grower and finisher). Diets met or exceeded NRC standards (Table 2). The mixer was flushed to prevent cross contamination of diets. All treatment feeds were mixed using a Davis S-20 mixer and pelleted using a California Pellet Mill (cold pellet temperature 65-70 C). Samples were collected from each treatment diet from the beginning, middle, and end of each batch and blended together to confirm enzyme activities and Enviva Pro presence in feed.

TABLE 2

Experimental diet composition of Example 1.

| Ingredient (%) | Starter | Grower | Finisher |
|---|---|---|---|
| Maize | 53.62 | 57.87 | 59.82 |
| Maize DDGS | 10.00 | 10.00 | 10.00 |
| Soybean Meal 49% CP | 26.93 | 23.97 | 21.36 |
| Ampro 55 | 5.00 | 5.00 | 5.00 |
| Soy oil | 2.07 | 0.91 | 1.74 |
| Lysine | 0.24 | 0.24 | 0.24 |
| DL-methionine | 0.21 | 0.19 | 0.18 |
| L-threonine | 0.01 | 0.01 | 0.01 |
| Salt | 0.30 | 0.34 | 0.35 |
| Limestone | 1.04 | 1.07 | 0.94 |
| Dicalcium phosphate | 0.26 | 0.11 | 0.02 |
| Vitamin and trace mineral premix | 0.33 | 0.33 | 0.33 |

TABLE 2-continued

Experimental diet composition of Example 1.

| Ingredient (%) | Starter | Grower | Finisher |
|---|---|---|---|
| Calculated Nutrient Composition (%) | | | |
| CP | 22.60 | 21.50 | 20.39 |
| Energy, kcal/kg | 3060 | 3025 | 3100 |
| Digestible lysine | 1.36 | 1.26 | 1.21 |
| Digestible methionine | 0.58 | 0.61 | 0.53 |
| Digestible threonine | 0.83 | 0.83 | 0.80 |

Birds received feed ad-libitum appropriate to the treatment from day 0 to 42. Enzymes and Enviva Pro were provided by Danisco in the appropriate mixtures and levels for all experimental treatments. All diets contained 500 FTU of *E. coli* phytase in the background. The pens were arranged within the facility to prevent direct contact in order to avoid contamination. A change from starter to grower occurred on day 23. Grower diet was replaced with the finisher diet on day 35. At each feed change, feeders were removed from pens by block, weighed back, emptied, and refilled with the appropriate treatment diet. On the final day of the study feed was weighed. Pens were checked daily for mortality. When a bird was culled or found dead, the date and removal weight (kg) were recorded. A gross necropsy was performed on all dead or culled birds to determine the sex and probable cause of death. Signs of Necrotic Enteritis were noted.

All pens had approximately 4 inches of built up litter with a coating of fresh pine shavings. All birds were spray vaccinated prior to placement into pens with a commercial coccidiosis vaccine (Coccivac-B). On days 20, 21, and 22 all birds, except Treatment 1, were dosed with a broth culture of *C. perfringens*. A field isolate of *C. perfringens* known to cause NE and originating from a commercial broiler operation was utilized as the challenge organism. Fresh inoculum was used each day. The titration levels were approximately $1.0 \times 10^{8-9}$. Each pen received the same amount of inoculum. The inoculum was administered by mixing into the feed found in the base of the tube feeder. On day 23, five birds from each pen were selected, euthanized, group weighed, and examined for the degree of presence of Necrotic Enteritis lesions. The scoring was based on a 0 to 3 score, with 0 being normal and 3 being the most severe (0=none, 1=mild, 2=moderate, 3=marked/severe; Hofacre et al., 2003 J. Appl. Poult. Res. 12:60-64). No concomitant drug therapy was used during the study.

Means were separated using pair wise t-tests. Significant differences were considered at $P<0.05$. Pens were used as the experimental unit.

Results

Figure 1:
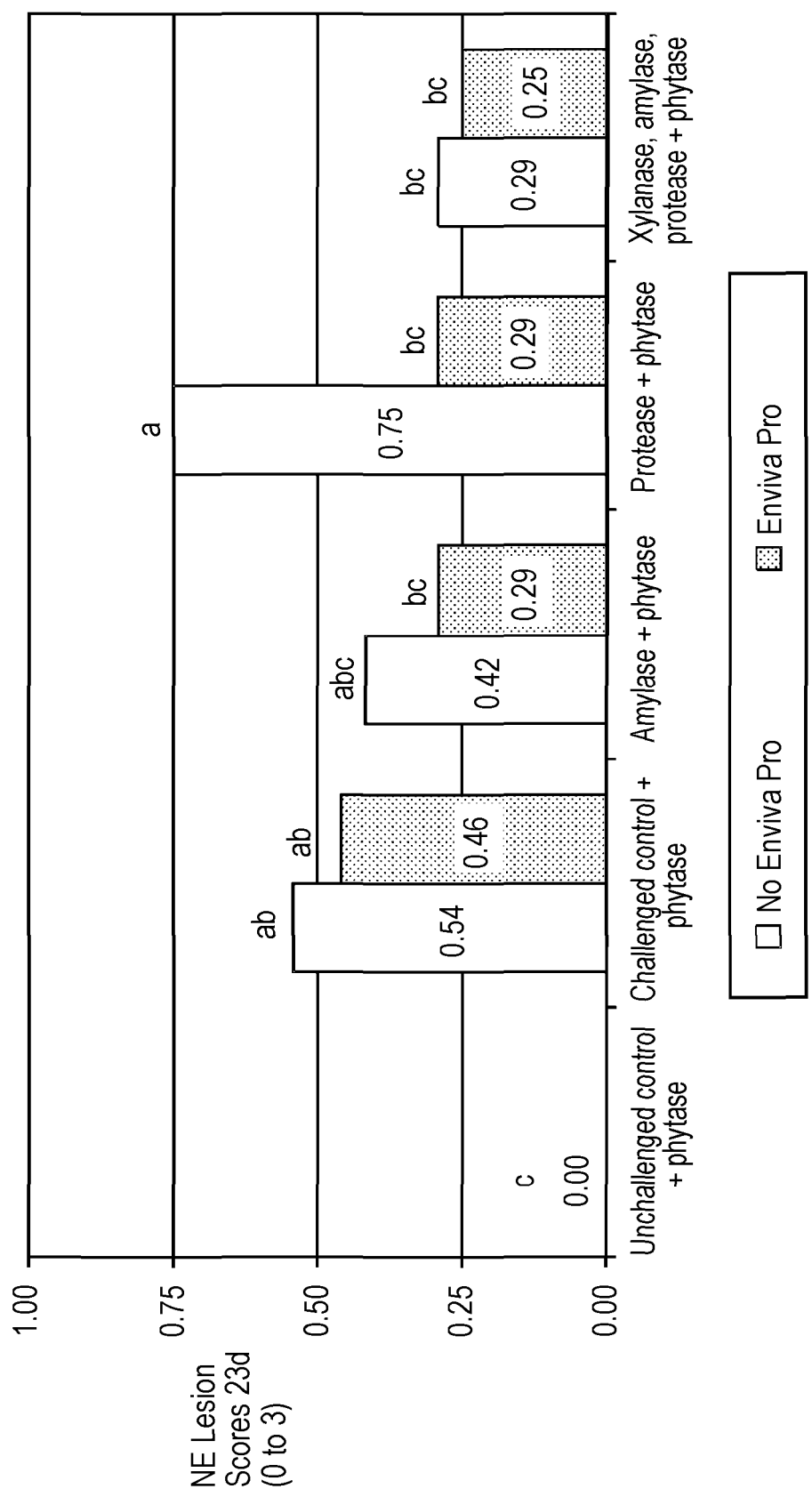
FIG. 1 shows that a combination of DFM (Enviva Pro® available from Danisco A/S) with a combination of a xylanase (e.g. an endo-xylanase from *Trichoderma* xylanase), an amylase (e.g. a *Bacillus licheniformis* alpha-amylase), a protease (e.g. *Bacillus subtilis* protease) and a phytase (e.g. 500 FTU/kg of Phyzyme XP (an *E. coli* phytase) available from Danisco A/S) significantly improved (reduced) necrotic enteritis lesion scores in the gut of the animals compared with the challenged control. In some embodiments the xylanase, amylase and protease may formulated together in AxtraXAP® [containing 2000 XU/kg feed of xylanase; 200 AU/kg feed of amylase and 4000 PU/kg feed of protease] also available from Danisco A/S).

FIG. 1 shows the necrotic enteritis lesion scores of broiler chickens in a necrotic enteritis challenge model, based on a 0 to 3 score system. Pooled SEM=0.15

The challenged control treatment increased lesion scores compared to the unchallenged control treatment. Addition of DFMs with a combination of a xylanase, amylase, protease and phytase reduced lesion scores compared to all other treatments. Addition of DFMs in combination with the enzymes reduced lesion scores compared DFMs alone or enzymes by themselves.

Figure 2:
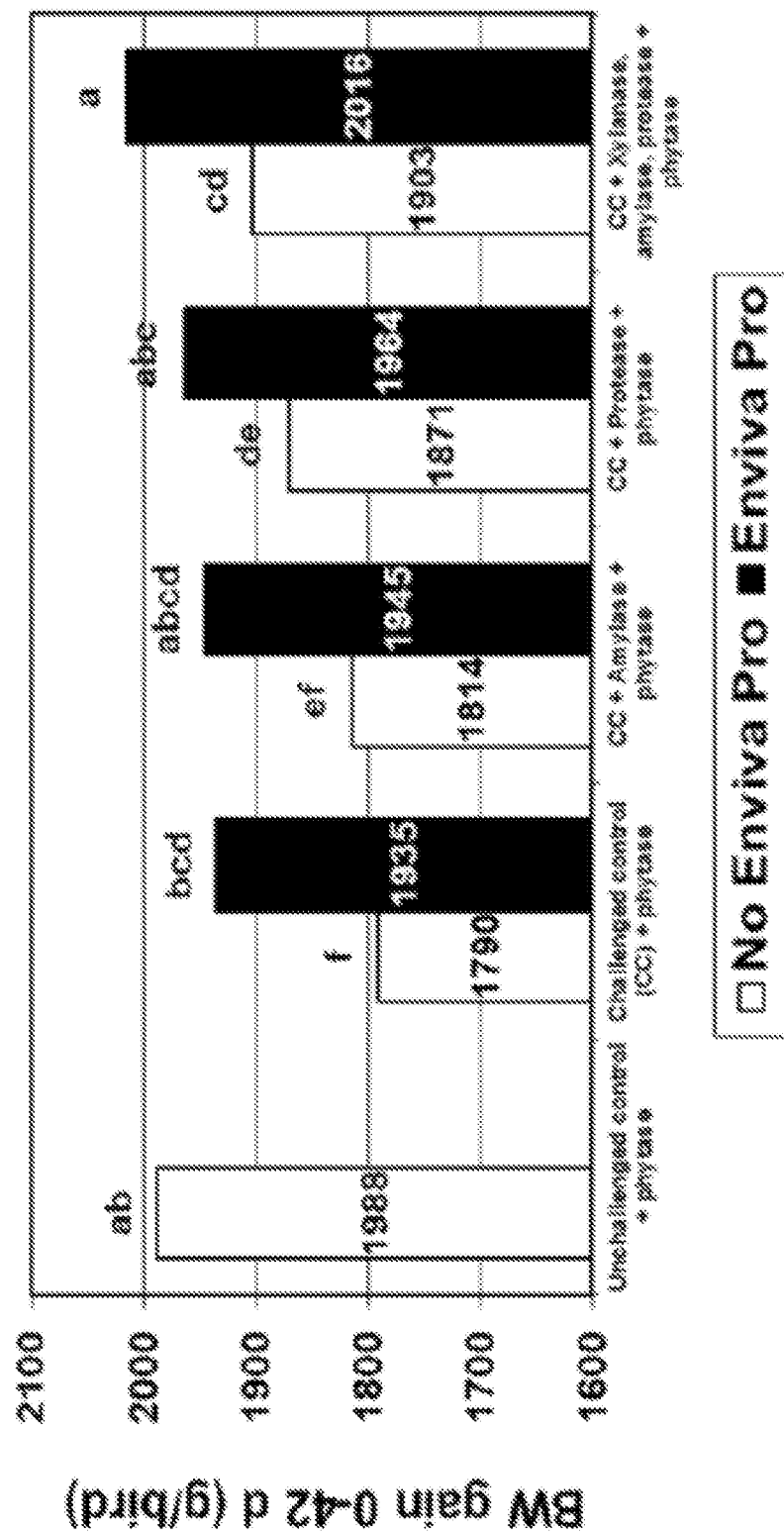
FIG. 2 shows that a combination of (Enviva Pro® available from Danisco A/S) with a combination of a xylanase (e.g. an endo-xylanase from *Trichoderma* xylanase), an amylase (e.g. a *Bacillus licheniformis* alpha-amylase), a protease (e.g. *Bacillus subtilis* protease) and a phytase (e.g. 500 FTU/kg of Phyzyme XP (an *E. coli* phytase) available from Danisco A/S) significantly improved Body weight gain (BW gain) in broiler chickens challenged with *Clostridium perfringens* compared with the challenged control—even resulting in a BW gain which was improved over a negative control (i.e. an unchallenged control). This was significantly better than any other combinations of enzymes such as either amylase and phytase or protease and phytase, and significantly better than DFM applied on the challenged control. In some embodiments the xylanase, amylase and protease may formulated together in AxtraXAP® [containing 2000 XU/kg feed of xylanase; 200 AU/kg feed of amylase and 4000 PU/kg feed of protease] also available from Danisco A/S). Pooled SEM=28.6

FIG. 2 shows the body weight gain of broiler chickens in a necrotic enteritis challenge model. Pooled SEM=28.6

FIG. 2 shows that a combination of the DFM (Enviva Pro®) with a combination of a xylanase, an amylase, a protease and a phytase significantly improved body weight gain (BW gain) in broiler chickens challenged with *Clostridium perfringens* compared with the challenged control—even resulting in BW gain which was improved over a negative control (i.e. an unchallenged control). This was significantly better than any other treatments.

Figure 3:
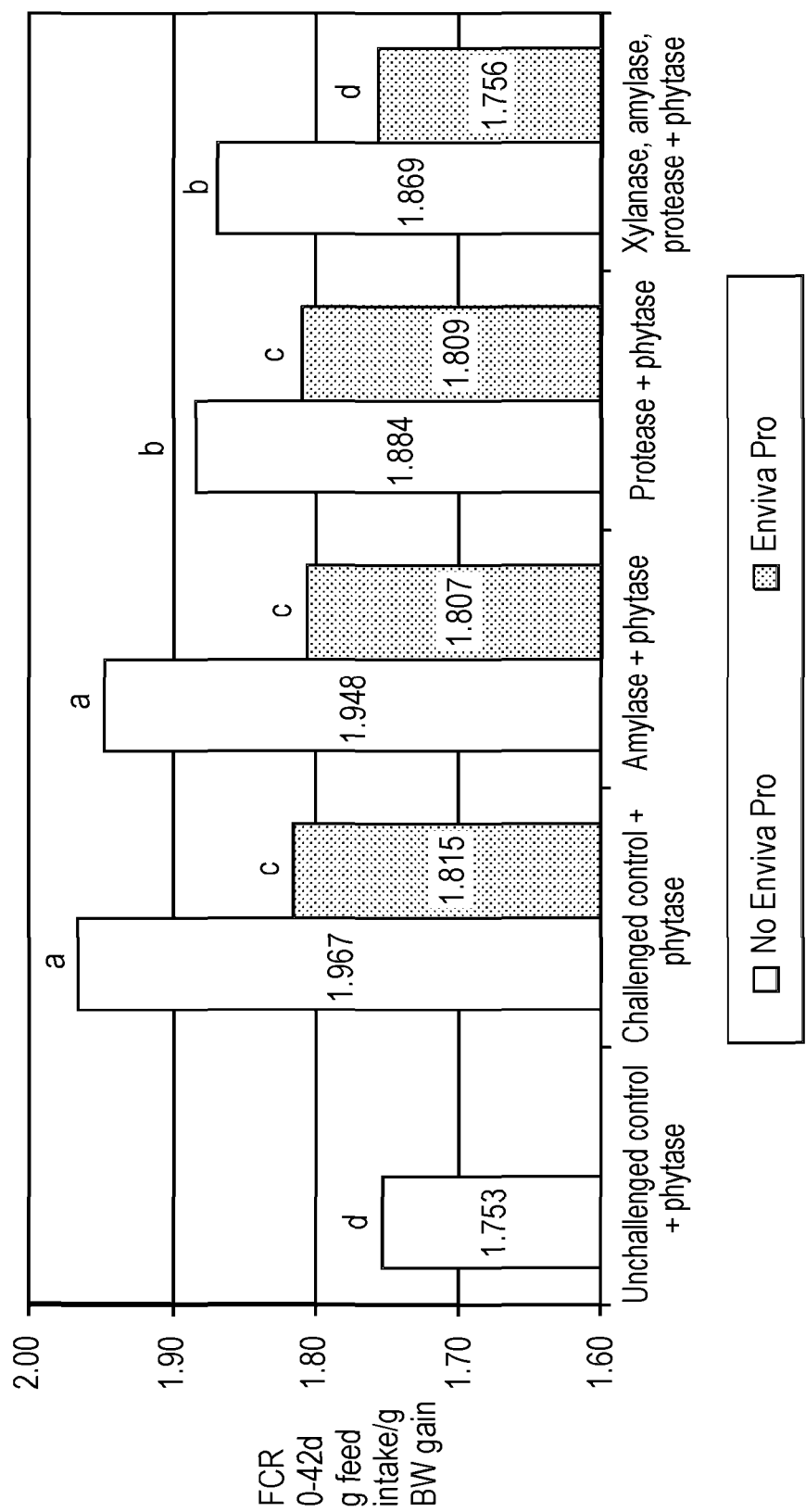
FIG. 3 shows a combination of (Enviva Pro® available from Danisco A/S) with a combination of a xylanase (e.g. an endo-xylanase from *Trichoderma* xylanase), an amylase (e.g. a *Bacillus licheniformis* alpha-amylase), a protease (e.g. *Bacillus subtilis* protease) and a phytase (e.g. 500 FTU/kg of Phyzyme XP (an *E. coli* phytase) available from Danisco A/S) significantly improved feed conversion ratio (FCR) (g feed intake/g BW gain) in broiler chickens challenged with *Clostridium perfringens* to the level of unchallenged birds. This was significantly better than other combinations of enzymes with the DFM such as either amylase and phytase or protease and phytase. In some embodiments the xylanase, amylase and protease may formulated together in AxtraXAP® [containing 2000 XU/kg feed of xylanase; 200 AU/kg feed of amylase and 4000 PU/kg feed of protease] also available from Danisco A/S).

FIG. 3 shows the feed conversion ratio of broiler chickens in a necrotic enteritis challenge model. Pooled SEM=0.016

The combination of Enviva Pro (DFM) with a xylanase, amylase, protease and phytase significantly improved (reduced) FCR (g BW gain/g feed intake) of broilers from hatch to 42 d compared to the challenged control, and enzymes by themselves and the other treatments.

Example 2

Materials and Methods

Cobb 500 male broiler chicks were obtained from a commercial hatchery. A total of 26 chicks were randomly assigned to one of 8 replicate pens per treatment. Floor pens (16 ft$^2$/pen) were located in a curtain-sided house containing controlled heating, circulating fans, heat lamps and fresh wood shavings. Birds were exposed to fluorescent lighting in a 24 h light cycle for the first four days and then 16 light:8 hour dark cycle for the remainder of the experiment. Feed was provided in bell feeders and water supplied via nipple drinkers ad libitum. A 5× dose of Coccivac-B (Intervet) was administered manually with a syringe into the oral cavity of chicks at one day of age.

TABLE 3

Experimental design of Example 2.

| Treatment | Coccidiosis vaccine | Phytase[1] | Additional enzyme[2] | DFM[3] |
|---|---|---|---|---|
| 1 | 5X | 500 FTU/kg | None | None |
| 2 | 5X | 500 FTU/kg | None | Enviva Pro (7.5 × 10$^4$ CFU/g) |
| 3 | 5X | 500 FTU/kg | Xylanase[4] (1000 u/kg) Amylase[4] (1800 u/kg) Protease[4] (5000 u/kg) | None |
| 4 | 5X | 500 FTU/kg | Xylanase[4] (1000 u/kg) Amylase[4] (1800 u/kg) Protease[4] (5000 u/kg) | Enviva Pro (7.5 × 10$^4$ CFU/g) |

[1]Phytase from *E. coli*.
[2]Amylase from *Bacillus amyloliquefaciens*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Avizyme 1505 ® provided by Danisco A/S.

Chicks were fed diets with or without either Enviva Pro or xylanase, amylase, and protease (Avizyme 1502; Table 3). Enzymes and Enviva Pro were provided by Danisco in the appropriate mixtures and levels for all experimental treatments. All diets contained 500 FTU of *E. coli* phytase. The pens were arranged within the facility to prevent direct contact in order to avoid contamination.

All diets were corn-soybean meal-DDGS based diets. Starter diets were provided during the study (dl-20). Diets were pelleted (65-70° C.) and crumbled. Samples were collected from each treatment diet from the beginning, middle, and end of each batch and blended together to confirm enzyme activities and Enviva Pro presence in feed.

TABLE 4

Experimental diet composition of Example 2.

| Ingredient (%) | Starter (0-20 d) | Grower (20-38 d) | Finisher (38-48 d) |
|---|---|---|---|
| Maize | 50.60 | 52.3 | 57.40 |
| Wheat Middlings | 1.33 | 1.03 | 1.32 |
| Maize DDGS | 7.00 | 7.00 | 7.00 |
| Soybean Meal | 34.60 | 33.50 | 28.60 |
| Vegetable fat | 2.50 | 2.50 | 2.50 |
| Limestone | 1.41 | 1.38 | 1.09 |
| MD-Phosphate | 1.20 | 1.00 | 0.84 |
| DL-methionine | 0.31 | 0.27 | 0.27 |
| Salt | 0.46 | 0.46 | 0.46 |
| L-Lysine | 0.29 | 0.23 | 0.28 |
| Vitamin and Trace Mineral Premix | 1.50 | 1.50 | 1.50 |
| Calculated Nutrient Composition (%) | | | |
| ME poultry, kcal/kg | 2950 | 3000 | 3040 |
| CP | 23.0 | 22.5 | 20.4 |
| Calcium | 0.85 | 0.81 | 0.75 |
| Av. Phosphorus | 0.38 | 0.35 | 0.32 |
| TSAA | 0.98 | 0.94 | 0.89 |
| Lysine | 1.36 | 1.29 | 1.20 |
| Methionine | 0.62 | 0.59 | 0.56 |

Body weights and feeder weights were recorded on day 1, 11, 20, 38 and 48 for calculation of feed intake, body weight gain and feed conversion. Mortality and culls were monitored on a daily basis and used to adjust for feed consumption and gain. One bird from six replicate pens was euthanized by cervical dislocation for collection of mucosal scrapings on days 11 and 20. Mucosal scrapings were collected from the ileum (Meckel's diverticulum to the ileo-cecal junction). The ileum was excised and cut along its length to expose the lumen and then flushed quickly and gently with PBS to remove digesta. The edge of a microscope slide was used to remove the mucosal layer by scraping along the length of the excised tissue section. The mucosal layer was immediately freeze clamped between aluminium plates in liquid N to preserve RNA integrity and stored in individual whirl-pack bags. Frozen tissue samples were stored in liquid N during sampling and at −80 C prior to analysis. Total RNA from mucosal scraping was isolated using the Trizol reagent (Invitrogen) using a mechanical homogenizer for tissue disruption. Total RNA (0.5 µg) was reverse transcribed to complementary DNA using iScript (Bio-Rad) according to the manufacturer's recommendations. The mRNA abundance of secreted inflammatory cytokine genes (interleukin-10, interferon-γ and interleukin-17) was assessed using chicken-specific primers. Additionally, TATA-BP, HPRT-1 and β-actin mRNA abundance was measured for data normalization using geNorm software. The fold-change in mRNA abundance in gene expression was determined using the modified delta-delta Ct equation as described by Rudrappa and Humphrey (2007) J. Nutr. 137: 427-432 and log transformed for data analysis.

Means were separated using pair wise t-tests. Significant differences were considered at P<0.05. Birds were used as the experimental unit for mRNA data.

Results

Figure 4:
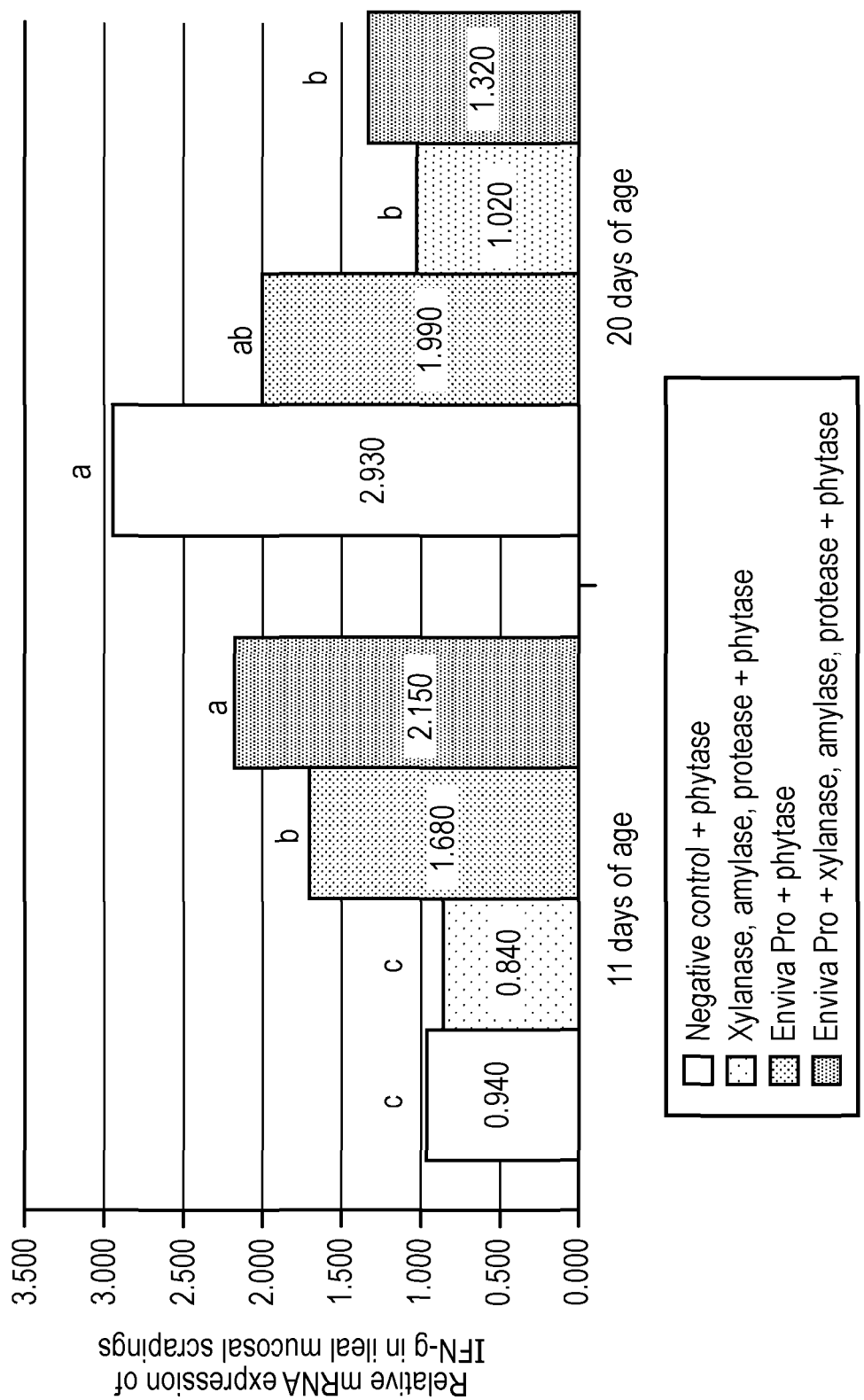
FIG. 4 shows relative mRNA expression of IFN-g used as marker of inflammation in the intestine, and shows that a combination of DFM (Enviva Pro®) with a combination of xylanase, amylase, protease and phytase (Avizyme 1502® available from Danisco A/S+500 FTU/kg of Phyzyme XP (an *E. coli* phytase) increased IFN-g expression at 11 days and reduced it at 20 days.

FIG. 4 shows mRNA abundance of interferon-gamma gene in ileal mucosal scrapings of broiler chickens.
Age 11 d: Pooled SEM=0.1
Age 20 d: Pooled SEM=0.6

The combination of Enviva Pro and xylanase, amylase, protease+phytase upregulated IFR-g expression in the ileum of 11-d-old-broilers that received 5 times a live coccidiosis vaccine at hatch compared to the negative control, Enviva Pro+phytase, and xylanase, amylase, protease+phytase. At 21 d, Enviva Pro+phytase, and the combination of Enviva Pro and xylanase, amylase, protease+phytase down regulated IFR-g expression in the ileum compared to the negative control. These data suggest that modulation of immune response may be one of the mechanisms of improved performance of DFMs in combination with the 4 enzymes in broilers.

Figure 15:
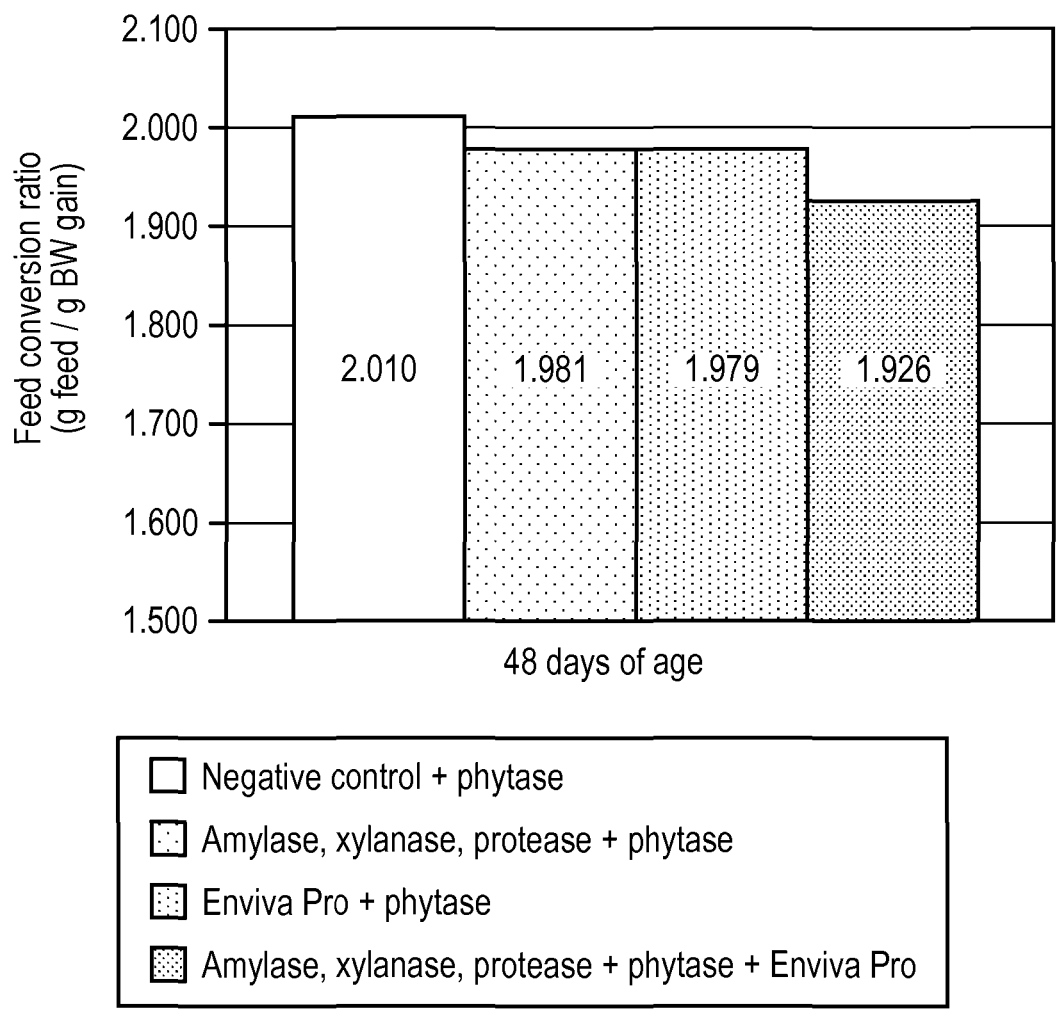
FIG. 15 shows feed conversion ratio of broiler chickens at 48 d of age.

FIG. 15 shows feed conversion ratio of broiler chickens at 48 d of age. Age 48 d: Pooled SEM=0.041

Example 3

Materials and Methods

One digestibility trial with broiler chickens was conducted to determine the effects of dietary enzymes and DFMs treatments on nutrient utilisation. The cages were housed in environmentally controlled rooms. The birds received 20-hour fluorescent illumination and, allowed free access to the diets and water. On day 1, a broiler live coccidiosis vaccine was given to all chicks via drinking water. Paper was provided on cage wire-floor for the first three days to enable recycling of *Eimeria Oocystes*. The study consisted of the following treatments (Table 5).

TABLE 5

Experimental design of Example 3.

| Treatment | Phytase[1] | Additional enzyme[2] | DFM[3] |
|---|---|---|---|
| 1 | 500 FTU/kg | None | None |
| 2 | 500 FTU/kg | Xylanase[4] (1000 u/kg) Amylase 1[4] (1800 u/kg) Protease[4] (5000 u/kg) | None |
| 3 | 500 FTU/kg | Xylanase (2000 u/kg) Amylase 2 (200 u/kg) | None |
| 4 | 500 FTU/kg | Xylanase[5] (2000 u/kg) Amylase 2[5] (200 u/kg) Protease[5] (5000 u/kg) | None |
| 5 | 500 FTU/kg | None | Enviva Pro (7.5 × 10[4] CFU/g) |
| 6 | 500 FTU/kg | Xylanase[4] (1000 u/kg) Amylase 1[4] (1800 u/kg) Protease[4] (5000 u/kg) | Enviva Pro (7.5 × 10[4] CFU/g) |
| 7 | 500 FTU/kg | Xylanase (2000 u/kg) Amylase 2 (200 u/kg) | Enviva Pro (7.5 × 10[4] CFU/g) |
| 8 | 500 FTU/kg | Xylanase[5] (2000 u/kg) Amylase 2[5] (200 u/kg) Protease[5] (5000 u/kg) | Enviva Pro (7.5 × 10[4] CFU/g) |

[1]Phytase from *E. coli*.
[2]Amylase 1 from *Bacillus amyloliquefaciens*, amylase 2 from *Bacillus licheniformis*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Avizyme 1505 ® provided by Danisco A/S.
[5]Axtra XAP ® provided by Danisco A/S.

A total of 192 birds were individually weighed and assigned on the basis of body weight to 48 cages (4 birds/cage). The 8 dietary treatments were then randomly assigned to six cages each. Birds received starter feed ad-libitum appropriate to the treatment from 0 to 21 days. Enzymes and Enviva Pro were provided by Danisco in the appropriate mixtures and levels for all experimental treatments. All diets contained 500 FTU of *E. coli* phytase. The pens were arranged within the facility to prevent direct contact in order to avoid contamination. Birds were fed starter diets (Table 6) in mash form throughout the experiment.

TABLE 6

Experimental diet composition of Example 3.

| Ingredient (%) | Starter |
|---|---|
| Maize | 46.22 |
| Wheat middlings | 6.73 |
| Maize DDGS | 7.00 |
| Soybean Meal 48% CP | 32.81 |
| Maize starch/enzyme/DFM premix | 0.30 |
| Animal/vegetable fat blend (50:50) | 3.00 |
| L-Lysine•HCl | 0.27 |
| DL-methionine | 0.30 |
| L-threonine | 0.11 |
| Titanium dioxide | 0.30 |
| Salt | 0.34 |
| Limestone | 1.12 |
| Dicalcium phosphate | 1.20 |
| Vitamin and trace mineral premix | 0.30 |
| Calculated Nutrient Composition (%) | |
| CP | 23.00 |
| ME, kcal/kg | 2950 |
| Calcium | 0.85 |
| Available phosphorus | 0.38 |
| Sodium | 0.18 |
| Digestible lysine | 1.21 |
| Digestible methionine | 0.62 |
| Digestible TSAA | 0.86 |
| Digestible threonine | 0.76 |

On day 21, four birds per cage were euthanized by intracardial injection of sodium pentobarbitone and contents of the lower ileum were expressed by gentle flushing with distilled water. Digesta from birds within a cage were pooled, resulting in six samples per dietary treatment. The digesta samples were frozen immediately after collection, lyophilised and processed. Digesta samples and diets were analysed for Ti, DM, GE, starch, fat, N and amino acids, excluding tryptophan, as per standard procedures. Calculation of ileal digestibility coefficients was performed as reported by Ravindran et al. (2005), based on the concentration of indigestible Ti. The energy contribution of starch, fat and protein to ileal digestible energy was calculated based on mean gross energy of starch (4.2 kcal/g), fat (9.4 kcal/g), or protein (5.5 kcal/kg). The improvement of digestible amino acids in response to enzymes and DFMs was expressed in relation to the amount of non-digested amino acids at the ileal level; the slope of that linear function was used as an indicator of the effects of the additives on amino acid digestibility.

Means were separated using pair wise t-tests. Significant differences were considered at $P<0.05$. Cages were used as the experimental unit.

Results

Figure 5:
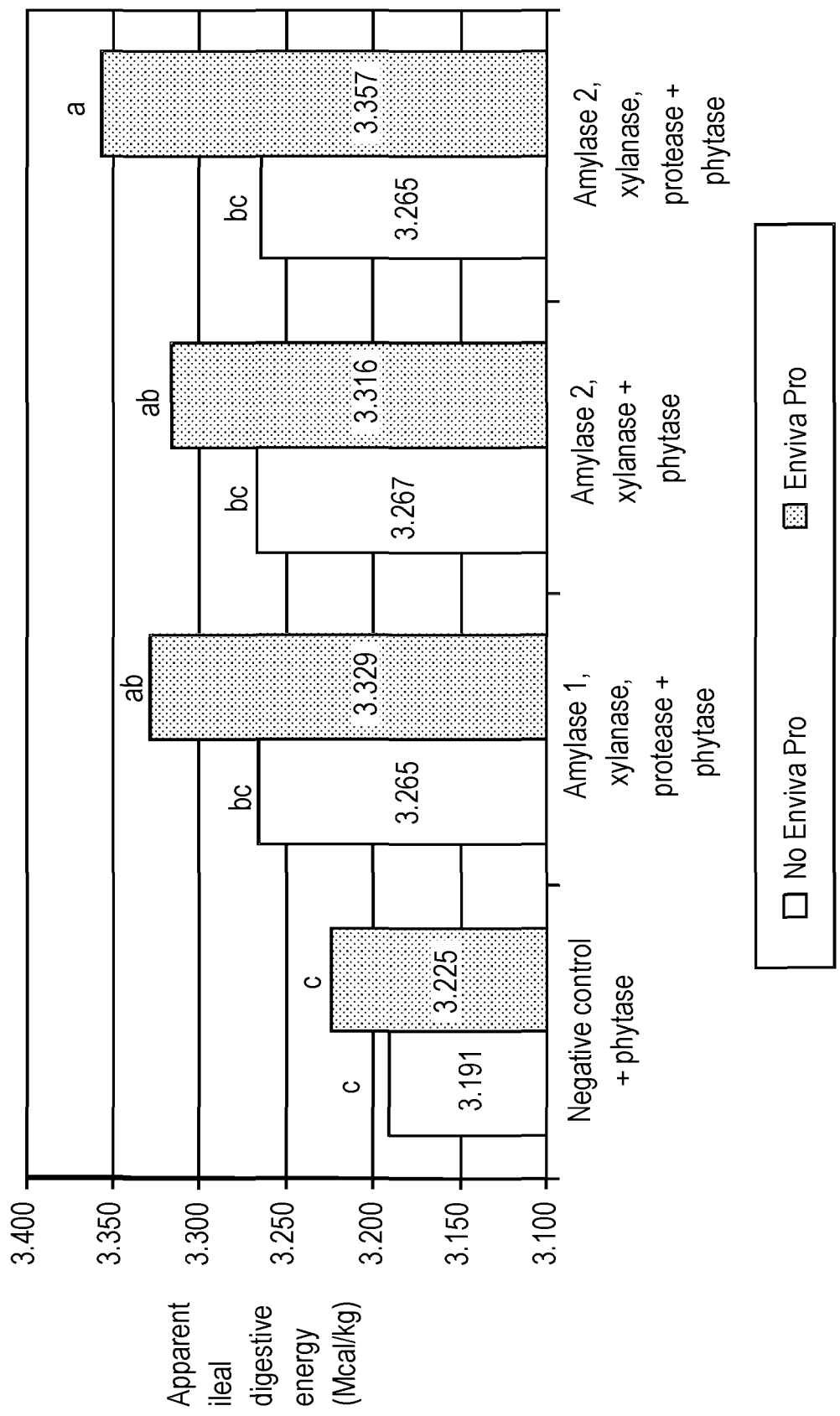
FIG. 5 shows apparent ileal digestible energy (mCal/kg) and shows that a combination of DFM (Enviva Pro®) with a xylanase, amylase, protease and phytase (two different enzyme mixes were used the first was Avizyme 1502® available from Danisco A/S+500 FTU/kg of Phyzyme XP (an *E. coli* phytase); and the second was AxtraXAP [containing 2000 XU/kg feed of xylanase; 200 AU/kg feed of amylase and 4000 PU/kg feed of protease] also available from Danisco A/S+500 FTU/kg of Phyzyme XP (an *E. coli* phytase) significantly improved energy digestibility effects.

FIG. 5 shows apparent ileal digestible energy of broiler chickens at 21 d of age. Pooled SEM=0.027

The addition of Enviva Pro (a DFM) in combination with an amylase, xylanase, protease and phytase exhibited commercially relevant increments of ileal digestible energy compared with the enzymes by themselves and the negative controls. These data indicates that DFMs improved the effects of these exogenous enzymes on the energy digestibility of poultry diets. For the avoidance of doubt Amylase 2 is through use of the amylase in AxtraXAP and Amylase 1 is through use of the amylase in Avizyme 1502.

Figure 6:
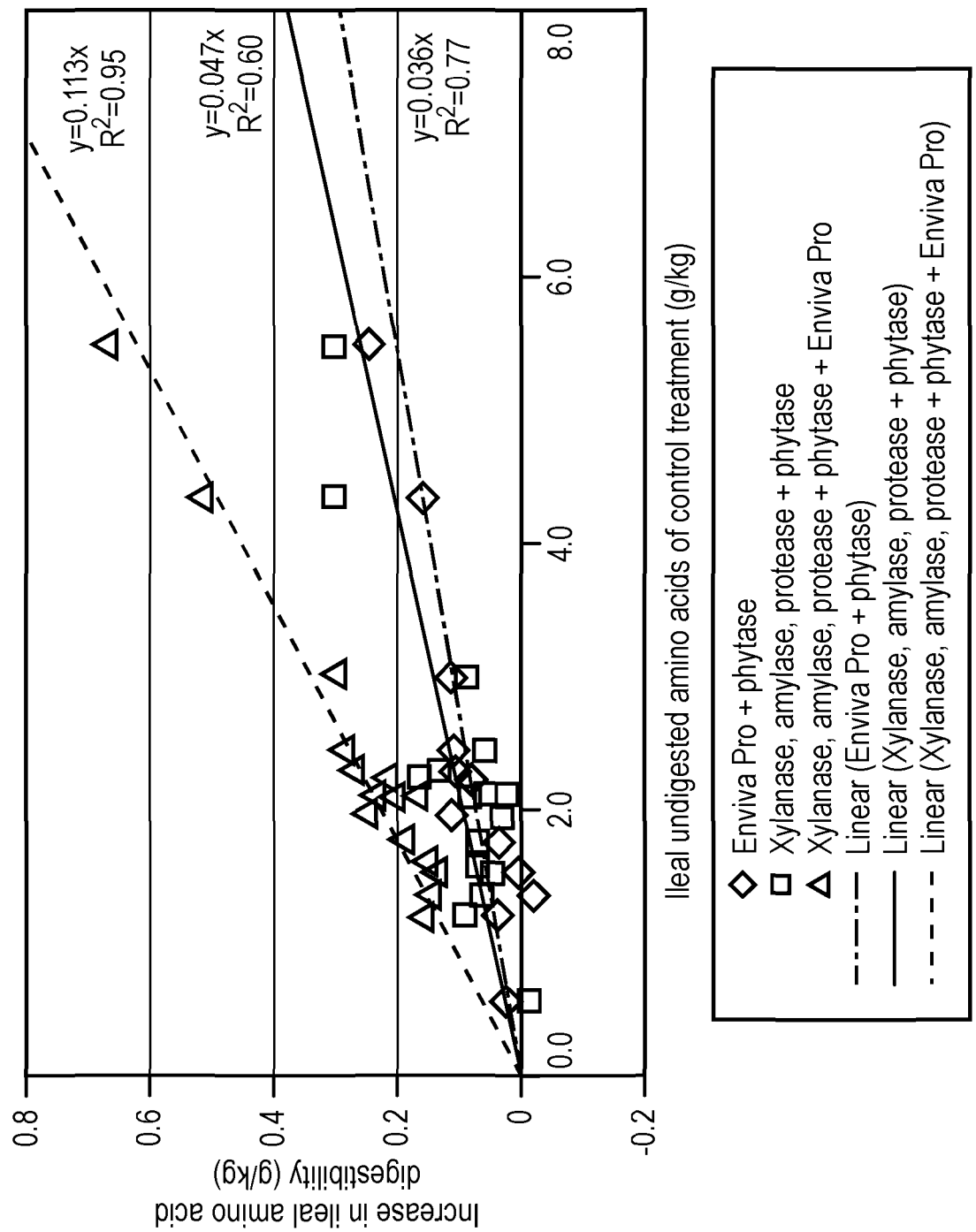
FIG. 6 shows amino acid digestibility significantly improved with a combination of DFM (Enviva Pro®) with a xylanase, amylase, protease and phytase. The improvement of digestibility of the undigested fractions of amino acid at the ileal level with a combination of DMF with xylanase, amylase, protease and phytase was greater than the improvement of DFM alone or the combination of xylanase, amylase, protease and phytase without DFM.

FIG. 6 show increments of ileal amino acid digestibility for three dietary treatments versus the control treatment as function of ileal undigested amino acids in the control treatment using 21-d-old broiler chickens.

The figure presents the improvement on ileal amino acid digestibility of dietary treatments with respect to the undigested fraction of amino acids in the ileum of broilers in the control treatment. Each point within a treatment represents one of the measured amino acids. The addition of Enviva Pro on top of xylanase, amylase 2, protease+phytase increased the ileal digestibility of amino acids (+11.3%) compared to Enviva Pro+Phytase (+3.6%) and xylanase, amylase 2, protease+phytase by themselves (i.e. without DFM) (+4.7%). These data indicates that DFMs improved the efficacy of these exogenous enzymes to increase amino acid digestibility of poultry diets.

Figure 7:
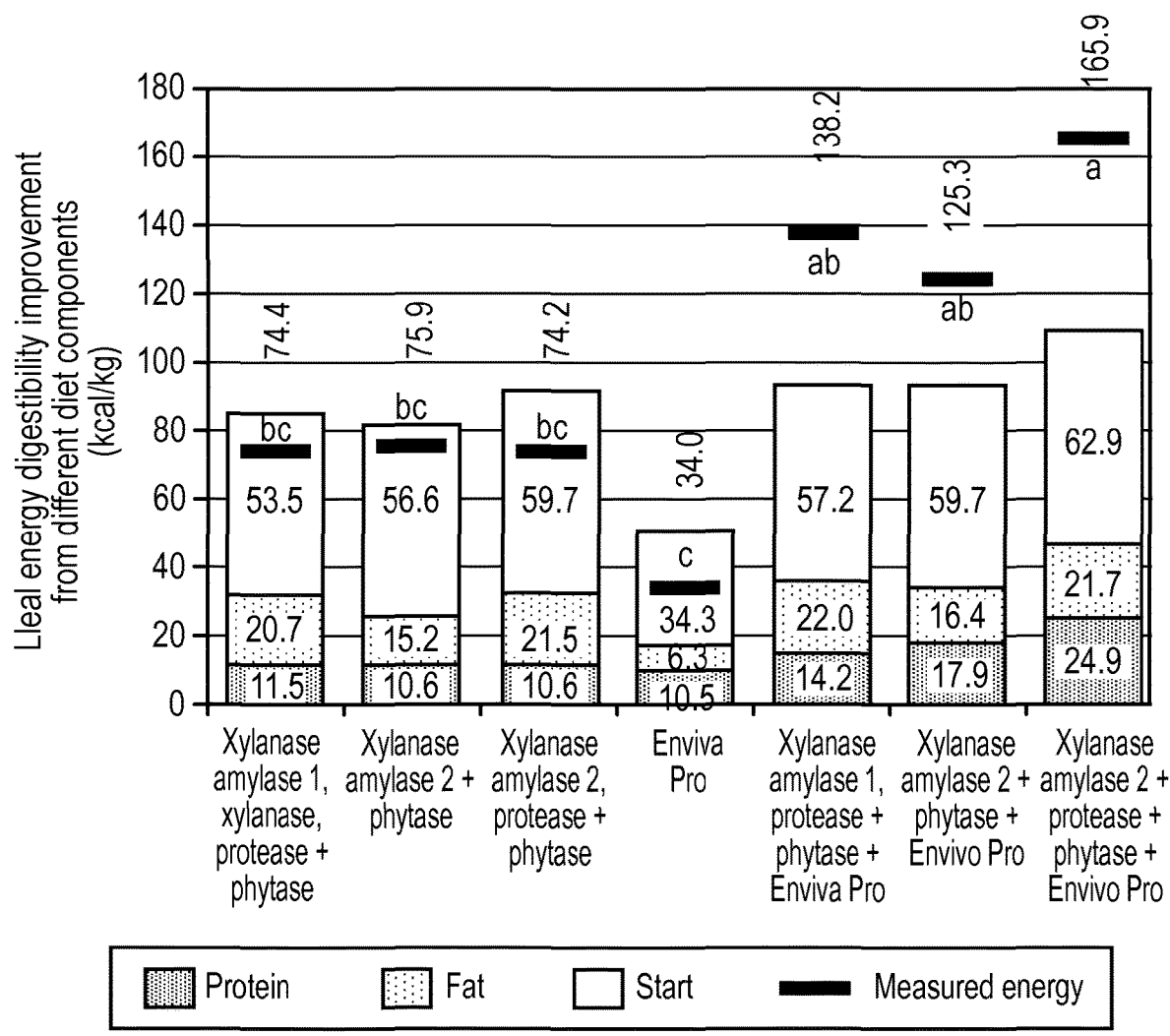
FIG. 7 shows energy digestibility improved with a combination of DFM (Enviva Pro®) with a xylanase, amylase, protease and phytase.

FIG. 7 shows the improvement of ileal digestible energy with respect to the control treatment using 21-d-old broiler chickens.

The figure presents the increment of ileal digestible energy of each dietary treatment compared a negative control treatment with phytase. Additionally, the calculated contributions of energy from starch, fat or protein are presented. Addition of Enviva Pro in combination with xylanase, amylase 2, protease+phytase increased the ileal digestible energy compared to the Enviva Pro+phytase treatment and the xylanase, amylase 2, protease+phytase by themselves treatment. Addition of Enviva Pro in combination with xylanase, amylase 1, protease+phytase produced commercially important increments on ileal digestible energy versus the enzymes by themselves. These data indicate an improved ability of the 4 enzymes to increase the ileal digestible energy of broiler diets in the presence of DFMs.

Example 4

Materials and Methods

One digestibility trial with broiler chickens was conducted to determine the effects of dietary enzymes and DFMs treatments on nutrient utilisation. The cages were housed in environmentally controlled rooms. The birds received 20-hour fluorescent illumination and, allowed free access to the diets and water. On day 1, a broiler live coccidiosis vaccine was given to all chicks via drinking water. Paper was provided on cage wire-floor for the first three days to enable recycling of *Eimeria Oocystes*. The study consisted of the following treatments (Table 7)

TABLE 7

Experimental design of Example 4.

| Treatment | Phytase[1] | Additional enzyme[2] | DFM[3] |
|---|---|---|---|
| 1 | None | None | None |
| 2 | 500 FTU/kg | Xylanase[4] (1000 u/kg) Amylase 1[4] (1800 u/kg) Protease[4] (5000 u/kg) | None |
| 3 | 500 FTU/kg | Xylanase[5] (2000 u/kg) Amylase 2[5] (200 u/kg) Protease[5] (5000 u/kg) | None |
| 4 | None | None | Enviva Pro (7.5 × 10[4] CFU/g) |
| 5 | 500 FTU/kg | Xylanase[4] (1000 u/kg) Amylase 1[4] (1800 u/kg) Protease[4] (5000 u/kg) | Enviva Pro (7.5 × 10[4] CFU/g) |
| 6 | 500 FTU/kg | Xylanase[5] (2000 u/kg) Amylase 2[5] (200 u/kg) Protease[5] (5000 u/kg) | Enviva Pro (7.5 × 10[4] CFU/g) |

[1]Phytase from *E. coli*.
[2]Amylase 1 from *Bacillus amyloliquefaciens*, amylase 2 from *Bacillus licheniformis*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Avizyme 1505 ® provided by Danisco A/S.
[5]Axtra XAP ® provided by Danisco A/S.

A total of 144 birds were individually weighed and assigned on the basis of body weight to 36 cages (4 birds/cage). The 6 dietary treatments were then randomly assigned to six cages each. Birds received starter feed ad-libitum appropriate to the treatment from 0 to 21 days. Enzymes and Enviva Pro were provided by Danisco in the appropriate mixtures and levels for all experimental treatments. The pens were arranged within the facility to prevent direct contact in order to avoid contamination. Birds were fed starter diets (Table 6) in mash form throughout the experiment.

TABLE 8

Experimental diet composition of Example 4.

| Ingredient (%) | Starter |
|---|---|
| Maize | 46.22 |
| Wheat middlings | 6.73 |
| Maize DDGS | 7.00 |
| Soybean Meal 48% CP | 32.81 |
| Maize starch/enzyme/DFM premix | 0.30 |
| Animal/vegetable fat blend (50:50) | 3.00 |
| L-Lysine•HCl | 0.27 |
| DL-methionine | 0.30 |
| L-threonine | 0.11 |
| Titanium dioxide | 0.30 |
| Salt | 0.34 |
| Limestone | 1.12 |
| Dicalcium phosphate | 1.20 |
| Vitamin and trace mineral premix | 0.30 |
| Calculated Nutrient Composition (%) | |
| CP | 23.00 |
| ME, kcal/kg | 2950 |
| Calcium | 0.85 |
| Available phosphorus | 0.38 |
| Sodium | 0.18 |
| Digestible lysine | 1.21 |
| Digestible methionine | 0.62 |
| Digestible TSAA | 0.86 |
| Digestible threonine | 0.76 |

Feed intake and total excreta output were measured quantitatively per cage over four consecutive days (from day 17 to 20) for the determination of nitrogen-corrected apparent metabolizable energy (AMEn) and Nitrogen retention. Daily excreta collections were pooled within a cage, mixed in a blender and sub-sampled. Each sub sample was lyophilized, ground to pass through a 0.5 mm sieve and stored in airtight plastic containers at −4 C pending analysis. Processed samples were analysed for DM, GE and N, using standard procedures.

Means were separated using pair wise t-tests. Significant differences were considered at P<0.05. Cages were used as the experimental unit.

Results

Figure 8:
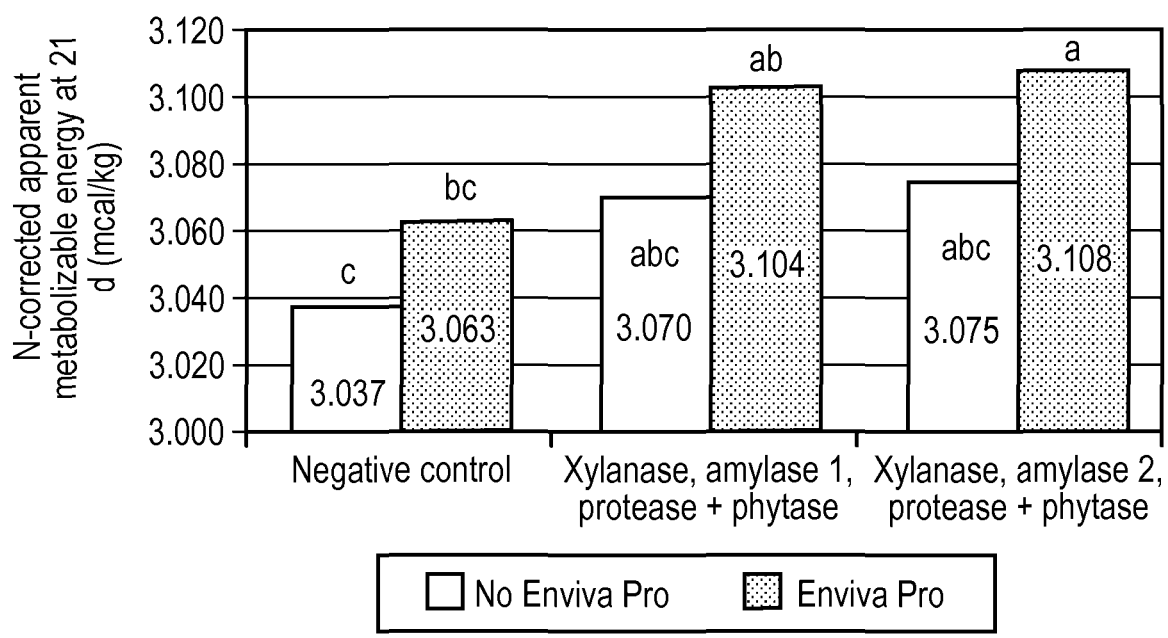
FIG. 8 shows nitrogen-corrected apparent metabolizable energy AMEn of dietary treatments fed to 17 to 21-d-old broiler chickens.

FIG. 8 shows nitrogen-corrected apparent metabolizable energy AMEn of dietary treatments fed to 17 to 21-d-old broiler chickens. Pooled SEM=0.015

Addition of Enviva Pro in combinations with xylanase, amylase, protease+phytase increased the AMEn of diets in response to enzymes compared to the negative control diet. In particular, addition of Enviva Pro in combination with xylanase, amylase 2, protease+phytase increased the AMEn of diets in response to enzymes compared to diets with only Enviva Pro.

Figure 9:
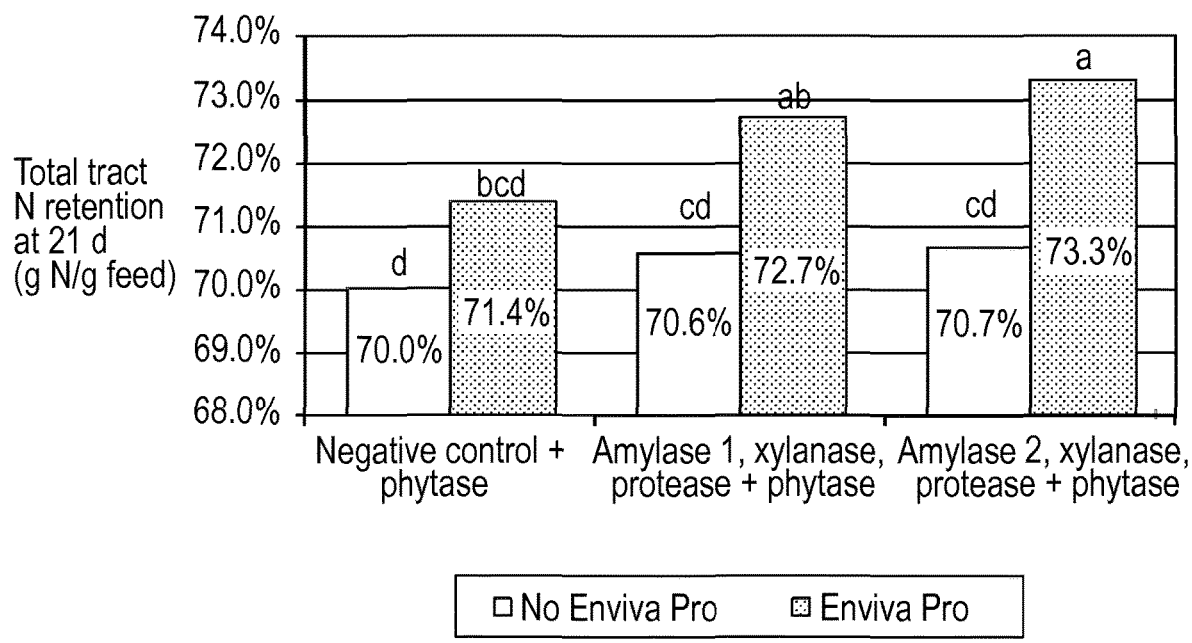
FIG. 9 shows that a combination of DFM (Enviva Pro®) with a xylanase, amylase, protease and phytase (two different enzyme mixes were used the first was Avizyme 1502® available from Danisco A/S+500 FTU/kg of Phyzyme XP (an *E. coli* phytase); and the second was AxtraXAP also available from Danisco A/S+500 FTU/kg of Phyzyme XP (an *E. coli* phytase) significantly improved nitrogen retention.

FIG. 9 shows nitrogen retention of 17 to 21-d-old broiler chickens. Pooled SEM=0.006

Addition of Enviva Pro in combination with xylanase, amylase, protease+phytase increased the nitrogen retention of broiler chickens in response to enzymes compared to the negative control diet. In particular, addition of Enviva Pro on top of xylanase, amylase 2, protease+phytase increased the nitrogen retention of broilers in response to enzymes compared to broilers fed diets with Enviva Pro only.

Example 5

Materials and Methods

Ross 308 male broiler chicks were obtained from a commercial hatchery. A total of 10 chicks were randomly assigned to one of 6 replicate cages per treatment. Birds were exposed to fluorescent lighting in a 24 h light cycle for the first four days and then 16 light:8 hour dark cycle for the remainder of the experiment. Feed and water were supplied ad libitum. The experimental design consisted of the following treatments.

TABLE 9

Experimental design of Example 5.

| Treatment | Coccidiosis vaccine | Coccidio stat | Phytase[1] | Additional enzyme[2] | DFM[3] |
|---|---|---|---|---|---|
| 1 | None | None | 500 FTU/kg | None | None |
| 2 | 5X | None | 500 FTU/kg | None | None |
| 3 | 5X | Salinomycin | 500 FTU/kg | None | None |
| 4 | 5X | None | 500 FTU/kg | None | Enviva Pro (7.5 × 10[4] CFU/g) |
| 5 | 5X | None | 500 FTU/kg | Xylanase[4] (1000 u/kg) Amylase[4] (1800 u/kg) Protease[4] (5000 u/kg) | None |
| 6 | 5X | None | 500 FTU/kg | Xylanase[4] (1000 u/kg) Amylase[4] (1800 u/kg) Protease[4] (5000 u/kg) | Enviva Pro (7.5 × 10[4] CFU/g) |

[1]Phytase from *E. coli*.
2Amylase from *Bacillus amyloliquefaciens*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Avizyme 1505 ® provided by Danisco A/S.

In treatments 2 to 6, an overdosed (recommended dose×5) coccidiosis vaccine (B, Intervet) was administered manually with a syringe into the oral cavity of chicks at one day of age. In treatment 2, Salinomycin (Bio-cox) was used at the approved level (60 g/MT) as a coccidiostat. The pens were arranged within the facility to prevent direct contact in order to avoid cross contamination with *Eimeria oocysts* and DFMs. Enzymes and Enviva Pro were provided by Danisco A/S in the appropriate mixtures and levels for all experimental treatments. All diets contained 500 FTU of *E. coli* phytase in the background.

TABLE 10

Experimental diet composition of Example 5.

| Ingredient (%) | Starter |
|---|---|
| Maize | 53.18 |
| Maize DDGS | 10.00 |
| Soyabean Meal 48% CP | 32.05 |
| Soyabean Oil | 1.07 |
| L-Lysine HCl | 0.31 |
| DL-methionine | 0.31 |
| L-threonine | 0.12 |
| Salt | 0.33 |
| Limestone | 1.14 |
| Dicalcium Phosphate | 1.19 |
| Vitamin and Trace Mineral Premix | 0.30 |
| Calculated Nutrient Composition (%) | |
| CP | 23.00 |
| ME, kcal/kg | 2950 |
| Calcium | 0.85 |
| Available phosphorus | 0.38 |
| Sodium | 0.18 |
| Digestible lysine | 1.21 |
| Digestible methionine | 0.63 |
| Digestible TSAA | 0.86 |
| Digestible threonine | 0.76 |

A total of 2 birds per replicate cage were euthanized at 14 d of age for collection of mucosal scrapings from mid-ileum. Ileums were flushed with distilled water and cut open with a pair of scissors. Opened sections were laid flat on a clean glass plate. Mucosa was carefully scraped from the mid region of ileum with the long edge of a glass slide. Each sample was stored in 2 ml of RNA later (Ambion) and frozen in a −80 C freezer. Samples were thawed on ice. Total RNA was isolated with Trizol reagent according to standard protocols. Integrity of RNA was determined on an agarose gel. RNA was reverse transcribed with the MMLV reverse transcriptase. Expression of mucin (MUC2) was determined by real time PCR on a Biorad real-time MyIQ machine.

Means were separated using pair wise t-tests. Significant differences were considered at $P<0.05$. Birds were used as the experimental unit for mRNA data.

Results

Figure 10:
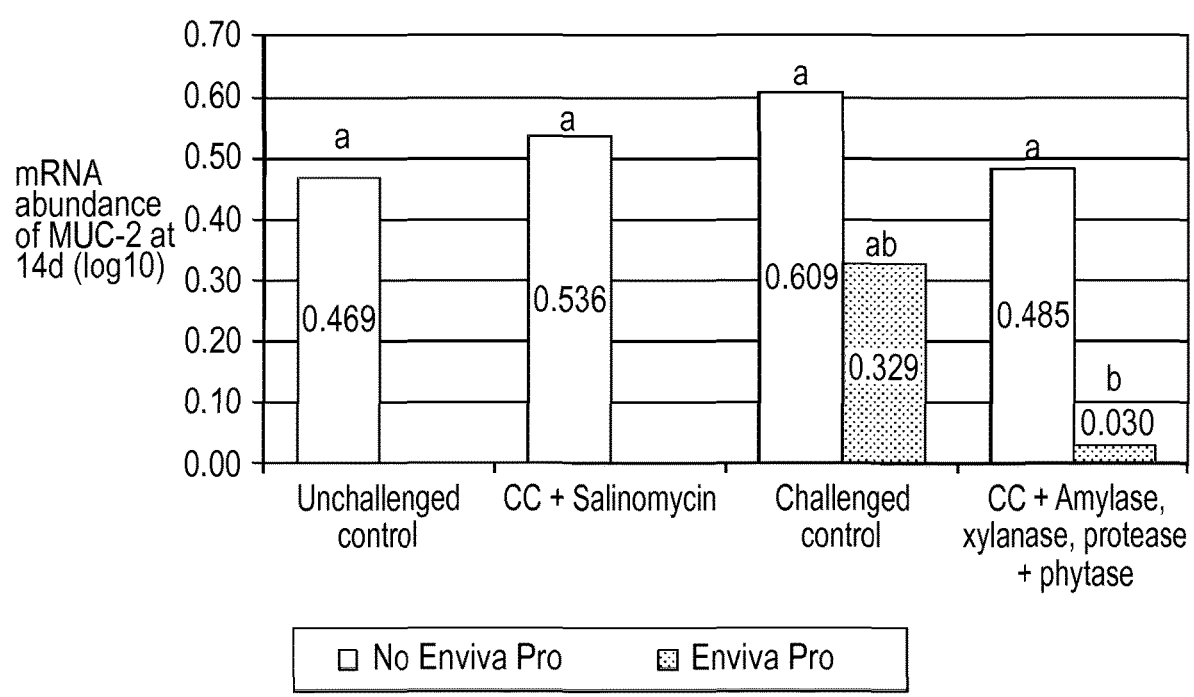
FIG. 10 shows that a combination of DFM (Enviva Pro®) with a xylanase, amylase, protease and phytase (Avizyme 1502® available from Danisco A/S+Phyzyme XP (an *E. coli* phytase)) significantly reduces the mRNA abundance of MUC-2 in the ileal mucosal scrapings at day 14 treated with an overdosed coccidian vaccine at hatch, compared to the challenged and unchallenged control treatments.

FIG. 10 shows mRNA abundance of MUC2 gene in ileal mucosal scrapings of broiler chickens at 14 d of age. Pooled SEM=0.14

Addition of Enviva Pro in combination with xylanase, amylase, protease+phytase down regulated the expression of MUC 2 in the ileum of broilers challenged with a 5×dose of a live coccidiosis vaccine compared to the challenged control. These data suggest that a reduction of endogenous amino acid losses due to reduced mucin secretion may be responsible for improved performance of broilers receiving combinations of DFMs and the 4 enzymes.

Example 6

Materials and Methods

Tissue samples were taken from broiler chicks from the trial presented in Example 1 at 23 days of age. Treatment specifications are presented in Table 1. The jejunum, pancreas and liver were removed from 2 birds from every pen and the mucosa pooled resulting in eight samples per treatment. The samples were rinsed in buffer solution (PBS) immersed in a tissue storage reagent (RNAlater) according to manufacturer's protocol and stored at −80° C. Total RNA was isolated from each tissue sample using a single step phenol-chloroform extraction method as described by Chomczynski and Saachi (1987; Anal. Biochem. 162:156-9). Concentration of the RNA was determined by measuring the absorbance at 260 nm (Nanodrop) and monitored for integrity by gel electrophoresis on 1.2% agarose gels. Only RNA of sufficient purity and having a ratio of absorption at 260 nm vs. 280 nm greater than 1.87 were considered for use.

Microarrays were manufactured using 70 base pair oligonucleotides (Opereon Biotechnologies Inc) according to the protocol described by Druyan et al. (2008; Poult. Sci. 87:2418-29). The experimental design of the array was a complete interwoven loop design as described by Garosi et al. (2005; Br. J. Nutr. 93:425-32) which each sample is compared directly with the others in a multiple pair wise fashion allowing all treatments to be compared. The samples were labelled according to the method described by Druyan et al. (2008; Poult. Sci. 87:2418-29) in that that half the samples would be labelled with Cy3 and half with Cy5 which are fluorescent dyes of cyanine. Hybridisation was carried out using the Pronto Plus! Microarray Hybridisation Kit prior to the addition of Cy3 and Cy5 labelled cDNA probes and covered with a clean glass coverslip (Lifterslip) and left to hybridise for 16 hours. The microarrays were then scanned on a Scan Array Gx PLUS Microarray Scanner set to 65% laser power to acquire images.

Total RNA from individual samples was reversed transcribed to produce cDNA which was then used as a template for the qPCR amplifications as described by Druyan et al. (2008; Poult. Sci. 87:2418-29). Thermocycling parameters were optimised for each gene and each gene was amplified independently in duplicate within a single instrument run.

Data files were generated from the scanned images of the microarrays but extracting the intensity raw data for each slide and dye combination using ScanAlyze Softare. Intensity data files were then analysed using JMP Genomics including and initial log 2 transformation. Data normalisation was performed using locally-weighted regression and smoothing first within array and across all arrays. The resulting normalised log 2 intensities were analysed using a mixed model ANOVA.

Mean intensities were compared using a threshold of significance based on Bongerroni correction of P=0.05. For the complete array, including all replicates, a mean by grid intensity was calculated for each gene using the 3 side by side probes, resulting in a total of four replicated means, one from each grid, per gene. Data for the Ct ratio from the samples in duplicate (sample gene Ct: Sample GAPDH Ct) depending on treatment were subjected to one way ANOVA.

Results

Expression data was collected using the microarray platform and a "heat map" produced to visualise the data for the jejunum (FIG. 16) and pancreas (FIG. 17). Relative expression levels of six genes of interest were converted to visual cues based on the scale seen in FIG. 16. Lowly expressed genes are are marked with a minus sign ("−"), and highly expressed genes are marked with a plus sign ("+"); whereas a greater gray intensity depicts a greater difference from the mean expression level of the treatments. The genes that were measured and their purported functions are seen in Table 11. Real-time PCR was used to validate the gene expression shown in the heat map for sucrase-isomaltase (SI) and amylase 2A (AMY2a) and were highly correlated to the array data.

TABLE 11

Purported function of genes measured.

| Gene | Identity | Function |
| --- | --- | --- |
| PEPT1 | Oligo-peptide transporter 1 | Nutrient transport |
| GCK | Glucokinase | Initial step in glucose metabolism |
| SI | Sucrase isomaltase | Glucose metabolism |
| ZO1 | Tight Junction protein 1 | Tight junction formation, intestinal integrity |
| CD3d | T-cell antigen CD3 | T-cell marker |
| AMY2A | Amylase 2A | Starch and sucrose metabolism |

Figure 16:
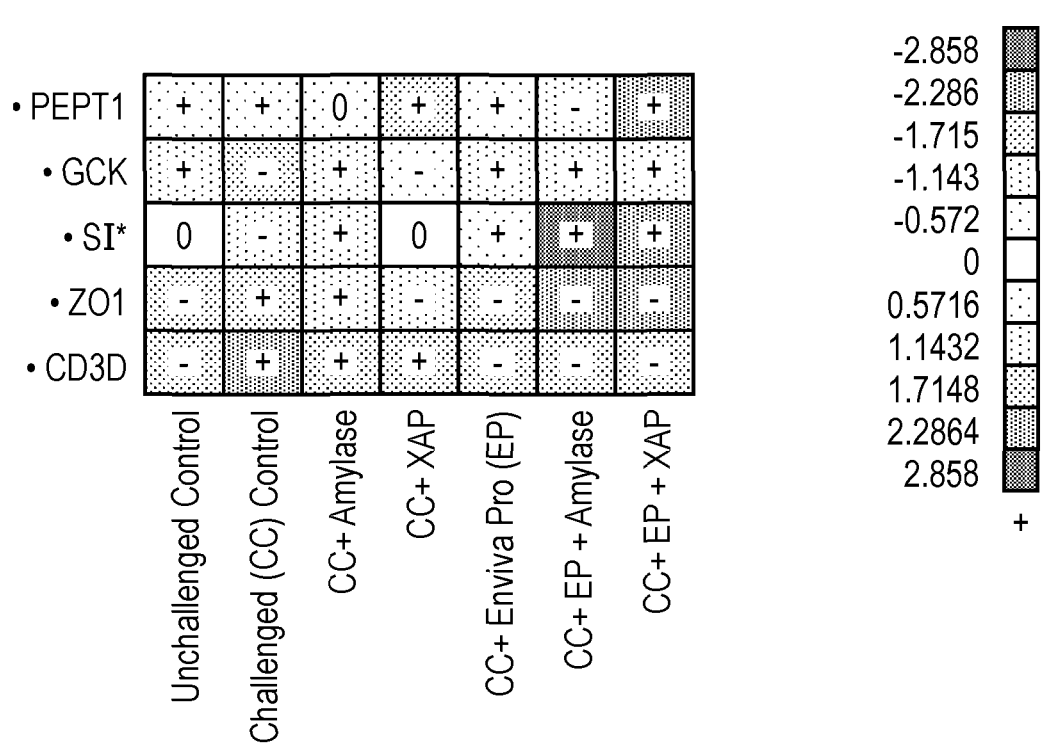
FIG. 16 shows a heat map of expression profiles of genes of interest for all treatments for jejunum at 23 days of age.

FIG. 16 shows a heat map of expression profiles of genes of interest for all treatments for jejunum at 23 days of age.

FIG. 17 shows a heat map of expression profile of chicken alpha amylase for all treatments in pancreas at 23 days of age.

In FIGS. 16 and 17 the key is as follows:
Unchallenged control=Unchallenged Control+phytase
CC=Challenged Control+phytase
CC+Amylase=Challenged Control+phytase+amylase
CC+XAP=Challenged Control+phytase+xylanase+amylase+protease
CC+EP=Challenged Control+phytase+Enviva Pro
CC+EP+Amylase=Challenged Control+phytase+amylase+Enviva Pro
CC+EP+XAP=Challenged Control+phytase+xylanase+amylase+protease+Enviva Pro The expression of oligo-peptide transport 1 (PEPT1) was increased by xylanase+amylase+protease+phytase, and this was increased further when in combination with Enviva Pro. PEPT1 is part of a peptide transport system and is responsible for the uptake of a wide range of di- and tri-peptides.

The expression of Glucokinase (GCK) was down-regulated by the challenged control but the combination of amylase+phytase or xylanase+amylase+protease+phytase with Enviva Pro produced an up-regulation similar to the unchallenged control. The extent of the up-regulation was greater than when xylanase+amylase+protease+phytase were used with Enviva Pro.

A similar pattern was also seen with sucrase iso-maltase (SI) where the combination of Enviva Pro with amylase+phytase or xylanase+amylase+protease+phytase produced a greater up-regulation than both the challenged and unchallenged control. GCK is a key enzyme in glucose metabolism and SI is responsible for hydrolysis of sucrose and isomaltose, and so has an important role in the digestion and absorption of carbohydrates in animals.

Tight Junction protein 1 (ZO1) was most highly expressed in the challenged control. A reduction was seen with the enzyme treatments but a greater down-regulation in expression was seen when Enviva Pro was used and particularly so when in combination with xylanase+amylase+protease+phytase which produced a similar level of down-regulation as the non-challenged control. ZO1 is a protein that is on the cytoplasmic face of tight junctions, there are various roles for this protein ranging from signal transduction for tight junction assembly to stability of the tight junctions themselves.

The T-cell antigen CD3 (CD3D) was highly expressed in the challenged control. The enzyme alone treatments did reduce expression somewhat but it was significantly down-regulated when in combination with Enviva Pro. The combination of xylanase+amylase+protease+phytase produced the largest down-regulation of the enzyme treatments, and, when in combination with Enviva Pro, produced an even larger down-regulation close to that seen for the unchallenged control. CD3D is a surface molecule found on T cells and plays an important role in signal transduction during T-cell receptor engagement and is part of the T-cell receptor/CD3 complex.

The alpha amylase (AMY2A) was highly expressed in the unchallenged and challenged controls but the addition of amylase+phytase or xylanase+amylase+protease+phytase resulted in reduced expression, which was further reduced when Enviva Pro was used in combination, particularly for xylanase+amylase+protease+phytase. Chicken alpha amylase is mainly produced in the pancreas and has a major role in starch digestion.

Discussion

The increase in expression of the peptide transporter oligopeptide transporter 1 (PEPT1) when xylanase+amylase+protease+phytase were given, particularly in combination with Enviva Pro, suggests increased availability of peptides and thus an increased requirement of peptide transporters, which indicates a synergistic effect of enzymes and DFMs to increase the adsorption of peptides for the animal which allows for greater growth. Animal performance results of Example 1 support this conclusion. The increase in expression of glucokinase and sucrase isomerase with the combination of amylase+phytase, or xylanase+amylase+protease+phytase, and Enviva Pro suggests that there was increased absorption of glucose, and increased availability of sucrose and isomaltose in the brush border, which indicates a positive interaction between the enzyme and DFMs to increase carbohydrate absorption in the small intestine and thus increase energy availability from the diet. The decrease of glucokinase expression for the challenged control suggests that the *Clostridium perfringens* challenge caused damage to the mucosa and that addition of Enviva Pro and xylanase+amylase+protease+phytase alleviated this.

The effect of Enviva Pro on reducing the expression of Tight junction protein 1 indicates lower requirement for protein turn over in the intestine, which may be related to a high intestinal integrity. The increased expression in the challenged control, however, suggests that turnover/requirement of the protein was high due to failing intestinal integrity possibly due to the coccidia and *Clostridium perfringens* infections. The enzymes alone did have some effect on ameliorating this but the additive effect seen with Enviva Pro suggests a greater benefit from the combination. This indicates that Enviva Pro acts to increase intestinal integrity and thus benefit the health of the animal. Increased intestinal integrity, and thus absorptive capacity, may be one of the mechanisms by which the effectiveness of exogenous enzymes is increased when a DFM is present.

The increased expression of T cell antigen CD3 d in the challenged control indicates increased cell-mediated immune response due to the challenge. In these conditions, birds will be undergoing sub-optimal performance because the immune response will demand energy that could be used for growth, and because some birds will experience a systemic disease response. The increased expression of this immunological marker was markedly reversed when Enviva Pro was used alone or in combination with enzymes. Down regulation of immune response in the intestine may be one of the mechanisms by which the effectiveness of exogenous enzymes in nutrient absorption and performance is increased when a DFM is present.

The down-regulation of alpha amylase (AMY2A) production that was seen with the combination of amylase+phytase, or xylanase+amylase+protease+phytase suggests that the chicken is reducing its production of endogenous amylase as a response to the exogenous enzymes supplied. The additive effect seen with Enviva Pro and xylanase+amylase+protease+phytase suggest that the DFM is working synergistically with the exogenous enzymes to allow the bird to utilise the energy that it would have spent producing enzymes for digestion of starch in the diet.

The net effect of a down-regulated immune response and higher intestinal integrity, and a better nutrient digestion and absorption with the combination of enzymes and DFMs, clearly determines enhanced production performance of broiler chickens.

Example 7

Materials and Methods

A digestibility trial with broiler chickens was conducted to determine the effects of dietary enzymes and DFM treatments on energy utilisation. A total of 288 day-old, male Ross 308 chicks were obtained from a commercial hatchery and brooded in raised wire battery pens until day 14. Birds were vaccinated with a live coccidia vaccine at hatch (Coccivac-B). Chicks were fed a corn-SBM-DDGS based starter diet. Chicks were provided experimental diets from day 14 until day 21. The feed and water were provided ad-libitum throughout the 21 day period. Six chicks were housed per pen in battery pens located within an environmentally controlled room, where they received supplemental heat starting at 35° C. on day-of-age and decreasing 2° C. weekly. Light was provided at 23 L:1 D. On day 15, chicks were individually weighed, sorted, wing banded and randomly allocated to the experimental units using a completely randomized design. Each treatment consisted of 8 pens per treatment. The study consisted of the following treatments (Table 12).

TABLE 12

Experimental design of Example 7.

| Treatment | Phytase[1] | Additional enzyme[2] | DFM[3,4] |
|---|---|---|---|
| 1 | None | None | None |
| 2 | 500 FTU/kg | Xylanase (2000 u/kg) Amylase (200 u/kg) Protease (5000 u/kg) | None |
| 3 | None | None | Enviva Pro (1.5 ×10$^5$ FTU/g) |
| 4 | 500 FTU/kg | Xylanase (2000 u/kg) Amylase (200 u/kg) Protease (5000 u/kg) | Enviva Pro (1.5 ×10$^5$ FTU/g) |
| 5 | None | None | GalliPro Tect (8 ×10$^5$ FTU/g) |
| 6 | 500 FTU/kg | Xylanase (2000 u/kg) Amylase (200 u/kg) Protease (5000 u/kg) | GalliPro Tect (8 ×10$^5$ FTU/g) |

[1]Phytase from Buttiauxella.
[2]Amylase from *Bacillus licheniformis*, xylanase from *Trichoderma reesei*, protease from *Bacillus subtilis*.
[3]Enviva Pro ® is a combination of *Bacillus subtilis* strains Bs2084, LSSAO1 and 15AP4, provided by Danisco A/S.
[4]GalliPro Tect is a DFM comprised by one strain of *Bacillus licheniformis* (DSM17236).

Enzymes and DFMs were sourced and provided by Danisco in the appropriate mixtures and levels for all experimental treatments. The pens were arranged within the facility to prevent direct contact in order to avoid cross contamination. Birds were fed starter diets (Table 13) in mash form throughout the experimental period.

TABLE 13

Experimental diet composition of Example 7.

| Ingredient (%) | Starter |
|---|---|
| Corn | 52.94 |
| Corn-DDGS | 12.00 |
| Soybean meal 48% | 29.38 |
| Animal/Vegetable Fat Blend | 1.08 |
| Salt | 0.40 |
| DL Methionine | 0.22 |
| Bio-Lys | 0.44 |
| Limestone | 1.30 |
| Dicalcium Phosphate | 1.27 |
| Choline chloride 60 | 0.10 |
| Vit/Min Premix | 0.63 |
| TiO$_2$ | 0.25 |
| Calculated Nutrient Composition (%) | |
| CP | 22.25 |
| ME, kcal/kg | 2925 |
| Calcium | 0.90 |
| Available phosphorus | 0.38 |
| Sodium | 0.18 |
| Digestible lysine | 1.20 |
| Digestible methionine | 0.52 |
| Digestible TSAA | 0.85 |
| Digestible threonine | 0.75 |

Clean excreta trays were put in place for the last 2 days and excreta samples were collected by pen on day 21. The collected excreta samples were frozen at −20° C. before they were oven dried at 65° C. for 3 days to determine the dry matter (AOAC International, 2005; method 934.01). The feed samples were also corrected to the dry matter basis be measuring 5.0 g of each sample and drying them in an oven at 100° C. for 24 hrs. The excreta samples were then ground through a 1-mm screen while the feed samples were ground 0.5-mm screen. Excreta samples and diets were analysed for Ti, DM, GE, and N, as per standard procedures. Apparent metabolizable energy (AME) calculation was based on the concentration of the indigestible marker (Ti) and the gross energy of diets and excreta. Appropriate corrections were made for differences in moisture content. N-corrected AME (AMEn) was determined for zero nitrogen retention by multiplication with 8.22 kcal per gram of nitrogen retained in the body (Hill and Anderson, 1958; J. Nutr. 64:587-603).

Means were separated using pair wise t-tests. Significant differences were considered at P<0.05. Cages were used as the experimental unit.

Results

FIG. 18 shows apparent metabolizable energy corrected by nitrogen retention (AME$_n$) of 21 d old broiler chickens. Effect of DFM; P<0.001; Effect of Enzyme; P<0.001; Effect of DFM×Enzyme; P=0.27; Pooled SEM=32 kcal.

Addition of Xylanase, amylase, protease, and phytase, in combination with Enviva Pro or GalliPro Tect resulted in improvements of AME$_n$ versus the control treatment, that were significantly greater compared to the enzymes or the DFMs by themselves. The AME$_n$ increments due to the combination of xylanase, amylase, protease, phytase, and Enviva Pro (235 kcal/kg) or GalliPro Tect (215 kcal/kg) were greater than the addition of the enzymes and the DFM effects when applied separately (152 kcal/kg for Enviva Pro, or 120 kcal/kg for GalliPro Tect), compared to the negative control treatment.

Example 8

Materials and Methods

One thousand and four hundred one-day-old Cobb male chicks were purchased from a commercial hatchery. At study initiation, fifty males were allocated to one of seven pens per treatment by blocks. The study consisted of the following treatments (Table 1):

TABLE 1

Experimental design of Example 8.

| Treatment | Clostridium perfringens Challenge | Phytase[1] | Additional enzyme[2] | DFM[3] |
|---|---|---|---|---|
| 1 | No | 500 FTU/kg | None | None |
| 2 | Yes | 500 FTU/kg | None | None |
| 3 | Yes | 500 FTU/kg | None | Enviva Pro (7.5 × 10$^4$ FTU/g) |
| 4 | Yes | 500 FTU/kg | Xylanase[4] (2000 u/kg) Amylase[4] (200 u/kg) Protease[4] (5000 u/kg) | Enviva Pro (7.5 × 10$^4$ FTU/g) |

[1]Phytase from *E. coli*.
[2]Amylase from *Bacillus licheniformis*, xylanase from *Trichoderma reesei*, protease from *Bacillus subtilis*.
[3]Enviva Pro ® is combination of *Bacillus subtilis* strains Bs2084, LSSAO1 and 15AP4, provided by Danisco A/S.
[4]Axtra XAP ® provided by Danisco A/S.

Bird weights by pen were recorded at study initiation, 21 d and termination (42 d). The pen was the unit of measure. Broiler diets were fed as crumbles (starter) or pellets (grower and finisher). Diets met or exceeded NRC standards (Table 2). The mixer was flushed to prevent cross contamination of diets. All treatment feeds were mixed using a Davis S-20 mixer and pelleted using a California Pellet Mill (cold pellet temperature 65-70 C). Samples were collected from each treatment diet from the beginning, middle, and end of each batch and blended together to confirm enzyme activities and Enviva Pro presence in feed.

TABLE 2

Experimental diet composition of Example 8.

| Ingredient (%) | Starter | Grower | Finisher |
|---|---|---|---|
| Maize | 50.959 | 59.6156 | 62.7488 |
| Maize DDGS | 12 | 12 | 12 |
| Soybean Meal 49% CP | 30.7176 | 22.5873 | 19.4 |
| Choline Chloride | 0.06 | 0.06 | 0.06 |
| Soy oil | 3.0693 | 2.7035 | 2.84841 |
| Lysine | 0.21 | 0.2426 | 0.244 |
| DL-methionine | 0.1723 | 0.1566 | 0.1341 |
| L-threonine | 0.0387 | 0.0551 | 0.0564 |
| Salt | 0.4668 | 0.4692 | 0.47 |
| Limestone | 1.4467 | 1.4501 | 1.33389 |
| Dicalcium phosphate | 0.7346 | 0.5349 | 0.571 |
| Vitamin and trace mineral premix | 0.125 | 0.125 | 0.125 |
| Calculated Nutrient Composition (%) | | | |
| CP | 22.642 | 19.45 | 19.45 |
| Energy, mcal/kg | 12.761 | 12.012 | 12.012 |
| Digestible lysine | 1.327 | 1.124778 | 1.124778 |
| Digestible methionine | 0.53142 | 0.475425 | 0.475425 |
| Digestible threonine | 0.89401 | 0.78494 | 0.78494 |

Birds received feed ad-libitum appropriate to the treatment from day 0 to 42. Enzymes and Enviva Pro were provided by Danisco in the appropriate mixtures and levels for all experimental treatments. All diets contained 500 FTU of *E. coli* phytase in the background. The pens were arranged within the facility to prevent direct contact in order to avoid contamination.

A change from starter to grower occurred on day 21. Grower diet was replaced with the finisher diet on day 35. At each feed change, feeders were removed from pens by block, weighed back, emptied, and refilled with the appropriate treatment diet. On the final day of the study, feed was weighed. Pens were checked daily for mortality. When a bird was culled or found dead, the date and removal weight (kg) were recorded. A gross necropsy was performed on all dead or culled birds to determine the sex and probable cause of death. Signs of Necrotic Enteritis were noted.

All pens had approximately 4 inches of built up litter with a coating of fresh pine shavings. All birds were spray vaccinated prior to placement into pens with a commercial coccidiosis vaccine (Coccivac-B). On days 18, 19, and 20 all birds, except Treatment 1, were dosed with a broth culture of *C. perfringens*. A field isolate of *C. perfringens* known to cause Necrotic Enteritis and originating from a commercial broiler operation was utilized as the challenge organism. Fresh inoculum was used each day. The titration levels were approximately $1.0 \times 10^{8-9}$. Each pen received the same amount of inoculum. The inoculum was administered by mixing into the feed found in the base of the tube feeder.

Sample Collection

On day 21, a total of 8 birds per treatment (1-2 birds per pen) were euthanised and the total gastrointestinal tract from below the gizzard to the ileal-cecal junction was collected from each bird and sent overnight on ice to the laboratory. The samples were further dissected in the laboratory to obtain a 20 cm portion of the jejunum surrounding the Meckle's diverticulum; the remainder of the intestinal tract was discarded. The sections were rinsed with 0.1% peptone to remove the intestinal contents and opened longitudinally to expose the epithelial lining. The sections were masticated in 99 ml of 0.1% peptone at 7.0 strokes/s for 60 s to release mucosa-associated bacterial cells. Bacteria were harvested from the masticated solution by centrifugation at 12,000×g for 10 minutes. The resultant bacterial pellet was resuspended in 10 ml of MRS broth+10% glycerol, flash-frozen in liquid nitrogen, and stored at −20° C. until further analysis.

DNA Isolation

Genomic DNA was isolated from all samples by phenol chloroform extraction and purified using Roche *Applied Science* High Pure PCR Template Purification Kit (Roche Diagnostics Corp., Indianapolis, Ind.). Samples were randomly pooled in pairs at the DNA level after extraction, for a total of four samples per treatment.

Pyrosequencing

Bacterial tag-encoded FLX amplicon pyrosequencing was performed as described by Dowd (Dowd et al. 2008; BMC Microbiol. 8, 125). An equivalent amount of DNA isolated from the intestinal mucosa from each bird was analyzed in pooled samples containing DNA from two birds. The V1-V3 region of the 16S rRNA gene was amplified in each sample using the primers 28 F (5'-GAGTTTGATCNTGGCTCAG) and 519R (5'-GTNTTACNGCGGCKGCTG). Following sequencing, raw data was screened and trimmed based on quality. Sequences were sorted by individual samples based on barcode sequences. Barcode tags were removed and non-bacteria ribosomal sequences were removed. The bacterial community composition was determined using BlastN comparison to a quality controlled and manually curated database derived from NCBI. The relative abundance of each bacterial ID was determined for each sample. Data was compiled at each taxonomic level using NCBI nomenclature.

Statistical Analysis

For performance data means were separated using pair wise t-tests. Significant differences were considered at P<0.05. Pens were used as the experimental unit.

Genus level identifications were used for the analysis of the pyrosequencing data. The relative abundance of each genus was calculated and used for the analysis. The results were analysed using a categorical model analysis and then a Chi-square probability calculated using JMP 8.0.2 (SAS institute, Cary, N.C.), where each sample representing two birds was considered an experimental unit.

Results:

FIG. 19 shows feed conversion ratio (FCR) of broiler chickens in a necrotic enteritis challenge model (Pooled SEM: 0.015).

The combination of Enviva Pro with xylanase, amylase, protease+phytase reduced FCR (g BW gain/g feed intake) compared to the challenged control treatment and the use of Enviva Pro and phytase alone. Feed conversion ratio was reduced by the combination to the level of the unchallenged control+phytase.

FIG. 20 shows relative abundance of *Lactobacillus* spp. at 21 d in the jejunal mucosa of broiler chickens, ChSq<0.0001.

FIG. 20 shows the relative abundance of *Lactobacillus* spp. in comparison to other species in the jejunal mucosa of broilers at 21 days in a necrotic enteritis challenge model. The proportion of Lactobacilli was reduced in the challenged control in comparison to the unchallenged control. The combination of Enviva Pro, xylanase, amylase, protease+phytase increases the proportion of Lactobacilli more so than Enviva Pro and phytase alone and the challenged control.

Lactobacilli are widely used as probiotics for both human and animal use (Patterson and Burkeholder 2003; *Poult Sci* 82 (4) 627-31) and have been documented to improve gut health to a level that could be comparable to antibiotic growth promoters (Awad et al. 2009 *Poult Sci* 88 (1) 49-56). Thus by increasing the proportion Lactobacilli in the gut microbiota, the combination of Enviva Pro, xylanase, amylase, protease+phytase can improve gut health and positively impact feed efficiency.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A feed additive composition comprising (i) an anti-pathogen direct fed microbial comprising *Bacillus subtilis* strains (a) 15A-P4 (PTA-6507), (b) 2084 (NRRL B-500130), and (c) LSSA01 (NRRL-B-50104) and (ii) a protease, a xylanase, an amylase and a phytase wherein said feed additive composition improves at least one production performance characteristic of an animal compared to the production performance characteristic of animal not fed said feed additive composition.

2. A feed additive composition according to claim 1 wherein the direct fed microbial further comprises a bacterium selected from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium Megasphaera* and combinations thereof.

3. A feed additive composition according to claim 1 wherein the direct fed microbial further comprises a bacterium selected from one or more of the following genera or species: *Bacillus subtilis, Bacillus licheniformis, Bacillus amyloliquefaciens, Enterococcus, Enterococcus* spp, *Pediococcus* spp, *Lactobacillus* spp, *Bifidobacterium* spp, *Lactobacillus acidophilus, Pediocosus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Bacillus cereus, Lactobacillus salivarius* ssp. *salivarius, Megasphaera elsdenii, Propionibacteria* sp and combinations thereof.

4. A feed additive composition according to claim 1 wherein the direct fed microbial is in the form of an endospore.

5. A feed additive composition according to claim 1 wherein the xylanase is an endo-1,4-β-d-xylanase or a 1,4 β-xylosidase.

6. A feed additive composition according claim 1 wherein the xylanase is from one of *Bacillus, Trichoderma, Thermomyces, Aspergillus, Penicillium* or *Humicola*.

7. A feed additive composition according to claim 1 wherein the protease is a subtilisin, a bacillolysin, an alkaline serine protease, a keratinase or a *Nocardiopsis* protease.

8. A feed additive composition according to claim 1 wherein the phytase is a 6-phytase or a 3-phytase.

9. A feed additive composition according to claim 8, wherein the phytase is a 6-phytase.

10. A feed additive composition according to claim 1 wherein the phytase is an *Escherichia coli* (*E. coli*) phytase or a *Buttiauxella* phytase or *Hafnia* phytase or a *Citrobacter* phytase or an *Aspergillus* phytase or a *Penicillium* phytase or a *Trichoderma* phytase or a *Hansenula* phytase.

11. A feed additive composition according to claim 1 wherein the amylase is selected from one or more of the group consisting of: an α-amylase, a G4-forming amylase, a β-amylase and a γ-amylases.

12. A feed additive composition according to claim 11, wherein the amylase is an α-amylase.

13. A feed additive composition according to claim 1 wherein the amylase is from *Bacillus licheniformis, B. amyloliquefaciens, Trichoderma* spp. or *Aspergillus* spp.

14. A feed additive composition according to claim 1 wherein the phytase is present at a dosage of between 200 FTU/g feed additive composition and 40,000 FTU/g feed additive composition.

15. A feed additive composition according to claim 1 wherein the amylase is present at a dosage of between 50 AU/g feed additive composition and 20000 AU/g feed additive composition.

16. A feed additive composition according to claim 1 wherein the xylanase is present at a dosage of between 500 XU/g feed additive composition and 40000 XU/g feed additive composition.

17. A feed additive composition according to claim 1 wherein the protease is present at a dosage of 1000 PU/g feed additive composition and 60000 PU/g feed additive composition.

18. A feed additive composition according to claim 1 wherein the direct fed microbial is present at a dosage of $3.75 \times 10^7$ CFU/g feed additive composition or $1 \times 10^{11}$ CFU/g feed additive composition.

19. The feed additive composition of claim 1 wherein the direct fed microbial consists of *Bacillus subtilis* strains: (a) 15A-P4 (PTA-6507), (b) 2084 (NRRB-500130), and (c) LSSA01 (NRRL-B-50104).

20. The feed additive composition of claim 1 wherein the at least one production performance characteristic comprises (i) weight gain; and/or (ii) improved feed conversion ratio (FCR) in poultry challenged with infection with *Clostridium perfringens*.

* * * * *